United States Patent
Sednev et al.

(10) Patent No.: US 10,174,202 B2
(45) Date of Patent: Jan. 8, 2019

(54) DYES WITH PHOSPHINIC ACID, PHOSPHINATE, PHOSPHONATE AND PHOSPHONAMIDATE SUBSTITUENTS AS AUXOCHROMIC GROUPS AND METHODS FOR PREPARING THE SAME

(71) Applicant: Max-Planck-Gesellschaft zur Foerderung der Wissenschaften e. V., Munich (DE)

(72) Inventors: Maksim Sednev, Wuerzburg (DE); Alexey Butkevich, Goettingen (DE); Heydar Shojaei, Goettingen (DE); Vladimir Belov, Goettingen (DE); Stefan Hell, Goettingen (DE); Christian Wurm, Goettingen (DE); Dirk Kamin, Goettingen (DE)

(73) Assignee: MAX-PLANCK-GESELLSCHAFT ZUR FOERDERUNG DER WISSENSCHAFTEN E. V., Munich (DE)

( * ) Notice: Subject to any disclaimer, the term of this patent is extended or adjusted under 35 U.S.C. 154(b) by 0 days.

(21) Appl. No.: 15/886,494

(22) Filed: Feb. 1, 2018

(65) Prior Publication Data
US 2018/0223102 A1 Aug. 9, 2018

(30) Foreign Application Priority Data
Feb. 3, 2017 (EP) ..................... 17000173

(51) Int. Cl.
| | | |
|---|---|---|
| C07F 9/28 | (2006.01) | |
| C07F 9/64 | (2006.01) | |
| C07F 9/655 | (2006.01) | |
| C09B 15/00 | (2006.01) | |
| C09B 1/16 | (2006.01) | |
| C07F 9/6553 | (2006.01) | |
| C07F 9/6558 | (2006.01) | |

(Continued)

(52) U.S. Cl.
CPC .............. *C09B 1/16* (2013.01); *C07F 9/4021* (2013.01); *C07F 9/4419* (2013.01); *C07F 9/6561* (2013.01); *C07F 9/65522* (2013.01); *C07F 9/65586* (2013.01); *C07F 9/655372* (2013.01); *C09B 5/2436* (2013.01); *C09B 57/00* (2013.01)

(58) Field of Classification Search
CPC .... C07F 9/64; C07F 9/28; C07F 9/655; C07F 9/6553; C09B 15/00; C09B 57/02
USPC .................. 546/21, 23; 549/5, 216
See application file for complete search history.

(56) References Cited

U.S. PATENT DOCUMENTS

| | | |
|---|---|---|
| 8,361,993 B2 | 1/2013 | Egorov et al. |
| 8,658,665 B2 | 2/2014 | Clunas et al. |

(Continued)

FOREIGN PATENT DOCUMENTS

| | | |
|---|---|---|
| WO | 2009083614 A1 | 7/2009 |
| WO | 2010067078 A2 | 6/2010 |
| WO | 2012052435 A1 | 4/2012 |

OTHER PUBLICATIONS

Gabbutt, C. D. et al.: Synthesis and reactivity of some 4-bromo-2H-chromenes and 2H-thiochromenes. Tetrahedron, vol. 50, pp. 2507-2522, 1994.*
Bhattacharya et al. (1981). Michaelis-arbuzov rearrangement. Chemical reviews, 81(4), 415-430.
Bottanelli et al. (2016). Two-colour live-cell nanoscale imaging of intracellular targets. Nature communications, 7, 10778: 1-5.
Butkevich et al. (2016). Fluorescent Rhodamines and Fluorogenic Carbopyronines for Super-Resolution STED Microscopy in Living Cells. Angewandte Chemie International Edition, 55(10), 3290-3294.
Engel, R. (1988). Phosphorus addition at sp2 carbon. Organic Reactions. p. 175-248.
Epstein et al. (2013). Enhanced sensitivity employing zwitterionic and pI balancing dyes (Z-CyDyes) optimized for 2D-gel electrophoresis based on side chain modifications of CyDye fluorophores. New tools for use in proteomics and diagnostics. Bioconjugate chemistry, 24(9), 1552-1561.

(Continued)

Primary Examiner — Charanjit Aulakh
(74) Attorney, Agent, or Firm — Caesar Rivise, PC

(57) ABSTRACT

Compounds of formula I are disclosed:

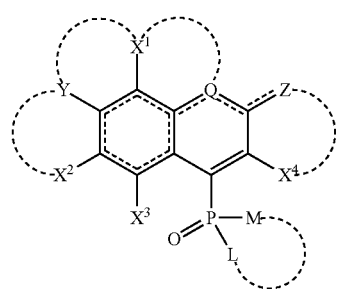

wherein $X^1$, $X^2$, $X^3$, $X^4$ are independently H, F, Cl, Br, I, CN, $NO_2$, $OR^1$, $SR^1$, $NR^1R^2$, $COR^1$, $COOR^1$, $CONR^1R^2$, $PO_3R^1R^2$, $SO_2R^1$, $SO_3R^1$ or $R^3$; $R^1$ and $R^2$ are, e.g., H, alkyl or aryl or optionally a ring; $R^3$ is, e.g., alkyl, alkenyl, alkynyl, aryl or cycloalkyl; Y is $OR^1$, $NR^1R^2$, or $NR^1R^3$; Q is O, S, $SO_2$, NR, $C(R^3)_2$, $Si(R^3)_2$, $Ge(R^3)_2$, $P(=O)R^3$ or $P(=O)OR^3$; Q and $X^1$ can optionally form part of a ring; L and M are independently $OR^1$, $SR^1$, $NR^1R^2$ and $R^3$; L and M can optionally form part of a ring; Z is O, S, $NR^1$, $CR^1R^3$ or aryl; and Z and $X^4$ can optionally form part of a ring.

21 Claims, 4 Drawing Sheets

(51) Int. Cl.
  *C07F 9/6561* (2006.01)
  *C07F 9/40* (2006.01)
  *C07F 9/44* (2006.01)
  *C09B 5/24* (2006.01)
  *C09B 57/00* (2006.01)

(56) References Cited

U.S. PATENT DOCUMENTS

| | | | |
|---|---|---|---|
| 9,549,933 | B2 | 1/2017 | Clunas et al. |
| 9,651,490 | B2 | 5/2017 | Zilles et al. |
| 2006/0199955 | A1 | 9/2006 | Lukhtanov et al. |
| 2017/0088534 | A1 | 3/2017 | Clunas et al. |

OTHER PUBLICATIONS

Gast et al. (1993). Das 2-Halogen-5,6-benzo-1,3,2-dioxaphosphorinan-4-on-Ringsystem/The 2-Halogeno-5, 6-benzo-1, 3, 2-dioxaphosphorinan-4-one Ring System. Zeitschrift für Naturforschung B, 48(7), 867-874.

Hardouin et al. (2007). Structure-activity relationships of α-ketooxazole inhibitors of fatty acid amide hydrolase. Journal of medicinal chemistry, 50(14), 3359-3368.

Hein et al. (2010). Stimulated emission depletion nanoscopy of living cells using SNAP-tag fusion proteins. Biophysical journal, 98(1), 158-163.

Koide et al. (2011). Evolution of group 14 rhodamines as platforms for near-infrared fluorescence probes utilizing photoinduced electron transfer. ACS chemical biology, 6(6), 600-608.

Kushida et al. (2015). Silicon-substituted xanthene dyes and their applications in bioimaging. Analyst, 140(3), 685-695.

Lukinavičius et al. (2013). A near-infrared fluorophore for live-cell super-resolution microscopy of cellular proteins. Nature chemistry, 5(2), 132-139.

Lukinavičius et al. (2014). Fluorogenic probes for live-cell imaging of the cytoskeleton. Nature methods, 11(7), 731-733.

Lukinavičius et al. (2016). Fluorogenic probes for multicolor imaging in living cells. Journal of the American Chemical Society, 138(30), 9365-9368.

Meyer et al. (1984). N2-(4-Substituted-2, 6-dichlorophenyl)-N1, N1-dimethylformamidines as antihypertensive and diuretic agents. Journal of medicinal chemistry, 27(12), 1705-1710.

Nealey et al. (1966). Synthesis of 3, 6-bis (dimethylamino) thio- and selenoxanthene. Journal of Heterocyclic chemistry, 3(2), 228-229.

Niu et al. (2016). Deep-Red and Near-Infrared Xanthene Dyes for Rapid Live Cell Imaging. The Journal of organic chemistry, 81(17), 7393-7399.

Pearson et al. (1968). Nucleophilic reactivity constants toward methyl iodide and trans-[Pt(py)2CI2]. Journal of the American Chemical Society, 90(2), 319-326.

Qian et al. (2016). Discovery and mechanism of highly efficient cyclic cell-penetrating peptides. Biochemistry, 55(18), 2601-2612.

Richard et al. (2003). Cell-penetrating peptides: A reevaluation of the mechanism of cellular uptake. Journal of Biological Chemistry, 278(1), 585-590.

Rodriguez et al. (2008). Targeting of mitochondria by 10-N-alkyl acridine orange analogues: role of alkyl chain length in determining cellular uptake and localization. Mitochondrion, 8(3), 237-246.

Sidenstein et al. (2016). Multicolour multilevel STED nanoscopy of actin/spectrin organization at synapses. Scientific reports, 6, 26725: 1-8.

Silhol et al. (2002). Different mechanisms for cellular internalization of the HIV-1 Tat-derived cell penetrating peptide and recombinant proteins fused to Tat. The FEBS Journal, 269(2), 494-501.

Singh et al. (2013). Genetically encoded multispectral labeling of proteins with polyfluorophores on a DNA backbone. Journal of the American Chemical Society, 135(16), 6184-6191.

Teng et al. (2016). Labeling proteins inside living cells using external fluorophores for microscopy. Elife, 5, p. 1-13.

Nest et al. (1925). Notes. Journal of the Chemical Society, Transactions, 127, 494-498.

Zanetti-Domingues et al. (2013). Hydrophobic fluorescent probes introduce artifacts into single molecule tracking experiments due to non-specific binding. PloS one, 8(9), e74200: 1-11.

Zheng et al. (2003). A convenient method for the synthesis of electron-rich phosphonates. Tetrahedron letters, 44(43), 7989-7992.

\* cited by examiner (C7-p = 0.29)

(X = H; C7-p = 0.29)

(C7-p = 0.27)

(C7-p = 0.28)

(C7-p = 0.27)

(C7-p = 0.18, C1-p = 0.15, C3-p = 0.13)

(C7-p = 0.23, C5-p = 0.21)

(C3-p = 0.25, C11-p = 0.12, C12-p = 0.12, C9-p = 0.12, C14-p = 0.12)

(C7-p = 0.29)

DYES WITH PHOSPHINIC ACID, PHOSPHINATE, PHOSPHONATE AND PHOSPHONAMIDATE SUBSTITUENTS AS AUXOCHROMIC GROUPS AND METHODS FOR PREPARING THE SAME

BACKGROUND OF THE INVENTION

Fluorescent dyes are widely used as indispensable markers in biology, optical microscopy, and analytical chemistry. In particular, the sensitive and stable imaging of cellular components depends on the favorable combination of chemical, biological and physical factors. The availability and proper choice of fluorescent dyes is a key factor to success of the entire labeling and imaging procedure. Due to their superior brightness and photostability, synthetic dyes represent an attractive alternative to fluorescent proteins.

Notwithstanding the large number of fluorescent dyes which are known and used for various labeling and imaging applications there is still a need for the new dyes possessing compact structures, increased Stokes shifts (separation between the absorption and emission maxima) and reactive groups. Dyes with compact structures and a zero net charge (neutral molecules or zwitterionic species with a short charge separation distance) are known to penetrate the outer plasma membrane of living cells and may be used as fluorescent labels in biology, optical microscopy and life sciences, when the imaging of living specimen is required. For example, among the multitude of fluorescent dyes reported hitherto, only triarylmethane dyes of rhodamine (see a) A. N. Butkevich, G. Y. Mitronova, S. C. Sidenstein, J. L. Klocke, D. Kamin, D. N. Meineke, E. D'Este, P. T. Kraemer, J. G. Danzl, V. N. Belov, S. W. Hell, *Angew. Chem. Int. Ed.* 2016, 55, 3290-3294; b) F. Bottanelli, E. B. Kromann, E. S. Allgeyer, R. S. Erdmann, S. Wood Baguley, G. Sirinakis, A. Schepartz, D. Baddeley, D. K. Toomre, J. E. Rothman, J. Bewersdorf, *Nat. Commun.* 2016, 7, 10778; c) B. Hein, K. I. Willig, C. A. Wurm, V. Westphal, S. Jakobs, S. W. Hell, *Biophys. J.* 2010, 98, 158-163; d) S. C. Sidenstein, E. D'Este, M. J. Bohm, J. G. Danzl, V. N. Belov, S. W. Hell, *Sci. Rep.* 2016, 6, 26725), carborhodamine (A. N. Butkevich, G. Y. Mitronova, S. C. Sidenstein, J. L. Klocke, D. Kamin, D. N. Meineke, E. D'Este, P. T. Kraemer, J. G. Danzl, V. N. Belov, S. W. Hell, *Angew. Chem. Int. Ed.* 2016, 55, 3290-3294; and silicon-rhodamine (SiR) (see a) G. Lukinavicius, K. Umezawa, N. Olivier, A. Honigmann, G. Yang, T. Plass, V. Mueller, L. Reymond, I. R. Correa, Jr., Z. G. Luo, C. Schultz, E. A. Lemke, P. Heppenstall, C. Eggeling, S. Manley, K. Johnsson, *Nat. Chem.* 2013, 5, 132-139; b) G. Lukinavicius, L. Reymond, E. D'Este, A. Masharina, F. Gottfert, H. Ta, A. Guther, M. Fournier, S. Rizzo, H. Waldmann, C. Blaukopf, C. Sommer, D. W. Gerlich, H. D. Arndt, S. W. Hell, K. Johnsson, *Nat. Methods* 2014, 11, 731-733; c) G. Lukinavicius, L. Reymond, K. Umezawa, O. Sallin, E. D'Este, F. Gottfert, H. Ta, S. W. Hell, Y. Urano, K. Johnsson, *J. Am. Chem. Soc.* 2016, 138, 9365-9368; d) Y. Kushida, T. Nagano, K. Hanaoka, Analyst 2015, 140, 685-695) classes bearing a carboxyl in the ortho-position of the pendant aromatic ring have been shown to provide specific vital labeling and perform well in superresolution fluorescence microscopy. Importantly, all these dyes feature small Stokes shifts of 20-40 nm. However, fluorescent dyes with increased Stokes shifts offer an advantage of using more flexible imaging schemes (when combined with small Stokes shift dyes). In this case two fluorescent labels (with small and large Stokes shifts) can be combined in one experiment and imaged separately; either by using two excitation sources and one detection channel, or by applying one excitation wavelength and two detection windows. Therefore, the discovery of new low molecular weight (MW) labels with increased Stokes shifts and sufficient emission efficiencies (because the very large Stokes shift (>100 nm) dyes typically demonstrate low fluorescence quantum yields, especially in aqueous media) is a vital task in modern biology-related natural science.

Another drawback persistent in bioconjugation techniques is that many widely used and bright lipophilic triarylmethanes are cationic dyes and bind non-specifically and stain membrane structures (L. C. Zanetti-Domingues, C. J. Tynan, D. J. Rolfe, D. T. Clarke, M. Martin-Fernandez, *PLoS One* 2013, 8, e74200).

On the other hand, numerous anionic fluorescent dyes, commercially available as sulfonates or phosphates, are hydrophilic and highly water-soluble but do not penetrate the intact plasma membrane. These labels are used nearly exclusively in immunostaining of fixed cells, and delivery of cell-impermeant labels into living cells requires the use of sophisticated techniques such as conjugation with membrane-permeant peptides (see a) Z. Qian, A. Martyna, R. L. Hard, J. Wang, G. Appiah-Kubi, C. Coss, M. A. Phelps, J. S. Rossman, D. Pei, *Biochemistry* 2016, 55, 2601-2612; b) J. P. Richard, K. Melikov, E. Vives, C. Ramos, B. Verbeure, M. J. Gait, L. V. Chernomordik, B. Lebleu, *J. Biol. Chem.* 2003, 278, 585-590; c) M. Silhol, M. Tyagi, M. Giacca, B. Lebleu, E. Vives, *Eur. J. Biochem.* 2002, 269, 494-501) or reversible membrane permeabilization (K. W. Teng, Y. Ishitsuka, P. Ren, Y. Youn, X. Deng, P. Ge, A. S. Belmont, P. R. Selvin, *eLife* 2016, 5, e20378).

In view of the drawbacks of fluorescent dyes of the prior art and the alternative strategies to obviate the limitations of their delivery to living cells and tissues, the main object of the present invention is to provide a novel general approach to dyes, in particular fluorescent dyes with superior properties such as:

1. neutral (with a zero net charge) or zwitterionic with a very short charge separation distance;
2. limited molecular mass (preferably with MW <500-700) and a compact structure;
3. bathochromic and bathofluoric shifts of absorption and emission bands, with the emission of light preferably in the red spectral region (>600 nm);
4. easy introduction of additional functional groups (e.g., carboxylate groups for further conjugation);
5. increased Stokes shifts (with sufficient emission efficiency).

This objective has been achieved by providing novel compounds and fluorescent dyes according to claims 1-9, a method for preparing the same according to claim 11, conjugates comprising said compounds and dyes according to claim 11, as well as the applications of the disclosed novel compounds according to claims 15 to 18. The newly introduced labels satisfy all of the above-stated requirements. Further aspects and more specific embodiments of the invention are the subject of further claims.

DESCRIPTION OF THE INVENTION

The novel compounds of the invention are compounds containing a phosphine oxide: —P(=O)(—R)—R', phosphinic acid: —(=O)(—OH)—R', phosphinate: —P(=O)(—OR)—R', phosphonic acid: —P(=O)(—OH)$_2$; phosphonic acid mono-ester (mono-phosphonate): —P(=O)(—OH)—OR', phosphonic acid di-ester (di-phosphonate): —P(=O)(—OR)OR' or phosphonamidate: —P(=O)

(—NR$_2$)—OR' group, directly connected via a C—P bond to a fluorophore, and are selected from the group consisting of compounds of the following general formula I (fluorescent dyes) and may be prepared from leuco dyes (such as that of formula IIa,b below), which are capable of being oxidized into fluorescent dyes of general formula I.

The novel compounds, in particular fluorescent dyes, of the invention have the general structural formula I below:

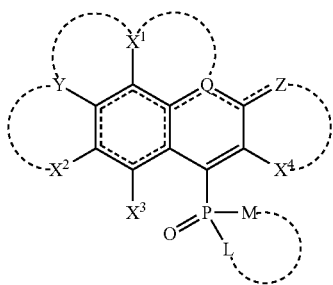

I wherein:

each $X^1$, $X^2$, $X^3$, $X^4$ is independently selected from H, halogen (F, Cl, Br, I), CN, NO$_2$, OR$^1$, SR$^1$, NR$^1$R$^2$, COR$^1$, COOR$^1$, CONR$^1$R$^2$, PO$_3$R$^1$R$^2$, SO$_2$R$^1$, SO$_3$R$^1$ and R$^3$, where:

R$^1$ and R$^2$ may represent H, unsubstituted or substituted alkyl (including cycloalkyl), unsubstituted or substituted aryl or unsubstituted or substituted heteroaryl, and wherein R$^1$ and R$^2$ can form together a substituted or unsubstituted 4-7 membered ring;

R$^3$ is alkyl, alkenyl, alkynyl, aryl or cycloalkyl, optionally substituted with one or more heteroatoms independently selected from N, O, S, halogen (F, Cl, Br, I), N$_3$, amine, OH, OR$^1$, OCOR$^1$, aryl, COOR$^1$, CONR$^1$R$^2$, PO$_3$H$_2$ and SO$_3$H, where R$^1$ and R$^2$ are defined as above;

Y is selected from OR$^1$, NR$^1$R$^2$, or NR$^1$R$^3$, where R$^1$, R$^2$ and R$^3$ are defined as above;

Q is selected from O, S, SO$_2$, NR, C(R$^3$)$_2$, Si(R$^3$)$_2$, Ge(R$^3$)$_2$, P(=O)R$^3$, P(=O)OR$^3$, where R$^3$ is defined as above, and wherein Q and X$^1$, taken together with the atoms to which they are bonded, can form a substituted or unsubstituted 5-7 membered ring;

L and M are independently selected from OR$^1$, SR$^1$, NR$^1$R$^2$ and R$^3$, where R$^1$, R$^2$ and R$^3$ are defined as above, and wherein L and M, taken together with the atoms to which they are bonded, can form a substituted or unsubstituted 5-7 membered ring;

Z is selected from O, S, NR$^1$, CR$^1$R$^3$ or aryl, where R$^1$ and R$^3$ are defined as above, and wherein Z and X$^4$, taken with the atoms to which they are bonded, can form a substituted or unsubstituted 5-7 membered ring.

Representative examples of compounds of the general structural formula I above are phosphorylated coumarin dyes (Q=O, Z=O), iminocoumarin dyes (Q=O, Z=NR$^3$), benzopyrylium dyes (Q=O$^+$; Z=OR$^1$, NR$^1$R$^2$ or substituted aryl), xanthylium dyes (Q=O, Z—X$^4$—fused benzene ring), anthrylium dyes (Q=CR$_2$, Z—X$^4$—fused benzene ring), benzanthrylium dyes (Q—X$^1$, Z—X$^4$—fused benzene rings), acridine dyes (Q=NR, Z—X$^4$—fused benzene ring), thioxanthylium dyes (Q=S, Z—X$^4$—fused benzene ring). However, the subject matter of the present invention is not limited to these classes of dyes.

In one specific embodiment of the compounds having the formula I, amine represents a group selected from NH$_2$, NH(alkyl), NH(aryl), N(alkyl)(aryl) and N(alkyl)$_2$.

In another specific embodiment of the compounds having the formula I, Z and X$^4$, taken with the atoms to which they are bonded, form a substituted or unsubstituted 5-7 membered ring, substituted with one or more additional heteroatoms selected from N, O and S or/and one or more substituents selected from halogen (F, Cl, Br, I), CN, N$_3$, B(OR$^1$)(OR$^2$), OR$^1$, SR$^1$, NR$^1$R$^2$, COR$^1$, COOR$^1$, CONR$^1$R$^2$, PO$_3$R$^1$R$^2$, SO$_2$R$^1$, SO$_3$R$^1$ and R$^3$, where R$^1$, R$^2$, R$^3$ are defined as above.

Further, more specific embodiments of the compounds having the formula I are represented by one of the following formulae Ia-Is:

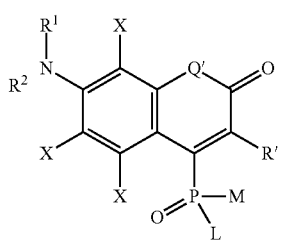

Ia wherein:

each substituent X is independently selected from: H, halogen (F, Cl, Br, I), CN, NO$_2$, OR$^1$, SR$^1$, NR$^1$R$^2$, COR$^1$, COOR$^1$, CONR$^1$R$^2$, PO$_3$R$^1$R$^2$, SO$_2$R$^1$, SO$_3$R$^1$ and R$^3$, where R$^1$, R$^2$, R$^3$ are defined as above;

the substituent R' is selected from H and R$^3$, where R$^3$ is defined as above; in particular R' may be unsubstituted 2-pyridyl, 4-pyridyl, 2-benzoxazolyl, 2-benzothiazolyl or a quarternary pyridinium or azolium derivative prepared therefrom and connected either directly, or through a polymethyne linker —(CH=CH)$_n$—.

Q' is selected from O, S, $SO_2$, NR, $C(R^3)_2$, $Si(R^3)_2$, $Ge(R^3)_2$, $P(=O)R^3$, $P(=O)OR^3$, where $R^3$ is defined as above, L, M, $R^1$, $R^2$ are defined as above;

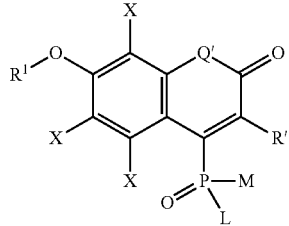

Ib wherein the substituents L, M, and $R^1$ are defined as above, the substituents Q', R' and X are defined as for formula Ia above;

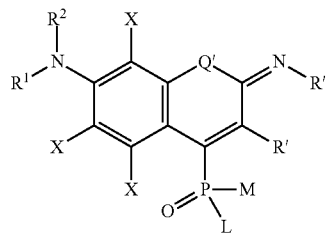

Ic wherein the substituents L, M, $R^1$ and $R^2$ are defined as above, the substituents Q', R' and X are defined as for formula Ia above;

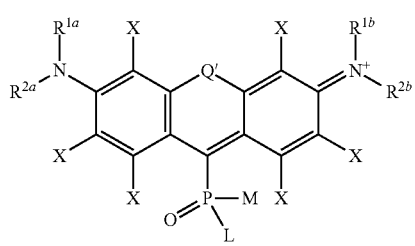

Id wherein:

$R^{1a}$ and $R^{2a}$ can represent H, alkyl, aryl or heteroaryl, and wherein $R^{1a}$ and $R^{2a}$ can form together a substituted or unsubstituted 4-7 membered ring;

$R^{1b}$ and $R^{2b}$ can represent H, alkyl, aryl or heteroaryl, and wherein $R^{1b}$ and $R^{2b}$ can form together a substituted or unsubstituted 4-7 membered ring;

L and M are defined as above,

Q' and X are defined as for formula Ia above, and the positive charge is delocalized among the atoms of the conjugated system in alternating positions (only one mesomeric structure Id is shown);

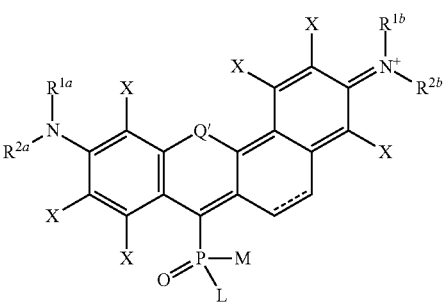

Ie wherein:

$R^{1a}$ and $R^{2a}$ can represent H, alkyl, aryl or heteroaryl, and wherein $R^{1a}$ and $R^{2a}$ can form together a substituted or unsubstituted 4-7 membered ring;

$R^{1b}$ and $R^{2b}$ can represent H, alkyl, aryl or heteroaryl, and wherein $R^{1b}$ and $R^{2b}$ can form together a substituted or unsubstituted 4-7 membered ring;

L and M are defined as above,

Q' and X are defined as for formula Ia above, and the positive charge is delocalized among the atoms of the conjugated system in alternating positions (only one mesomeric structure Ie is shown);

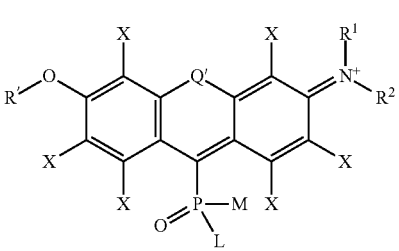

If wherein the substituents L, M, $R^1$ and $R^2$ are defined as above,

Q', R' and X are defined as for formula Ia above, and the positive charge is delocalized among the atoms of the conjugated system in alternating positions (only one mesomeric structure If is shown), in particular

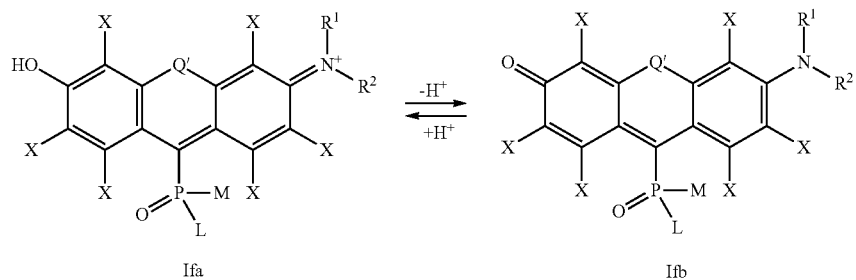

wherein L, M, R¹ and R², Q' and X are defined as above, and the positive charge in structure Ifa is delocalized among the atoms of the conjugated system in alternating positions (only one mesomeric structure Ifa is shown);

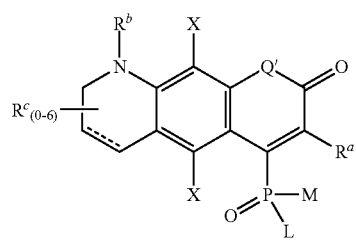

wherein the substituents L and M are defined as above,
Q' and X are defined as for formula Ia above,
$R^1$, $R^b$ and $R^c$ are independently selected from H and $R^3$, where $R^3$ is defined as above;

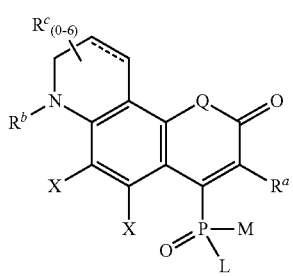

wherein the substituents L and M are defined as above,
Q' and X are defined as for formula Ia above,
$R^a$, $R^b$ and $R^c$ are independently selected from H and $R^3$, where $R^3$ is defined as above;

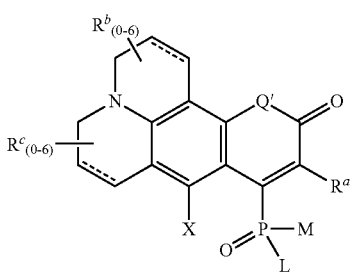

wherein the substituents L and M are defined as above,
Q' and X are defined as for formula Ia above,
$R^a$, $R^b$ and $R^c$ are independently selected from H and $R^3$, where $R^3$ is defined as above;

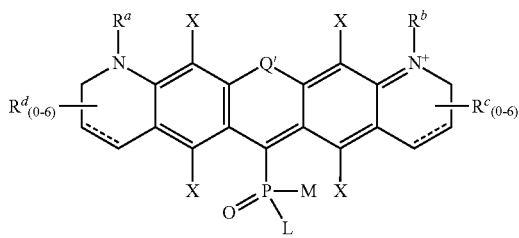

wherein the substituents L and M are defined as above,
Q' and X are defined as for formula Ia above,
$R^a$, $R^b$, $R^c$ and $R^d$ are independently selected from H and $R^3$, where $R^3$ is defined as above,
and the positive charge is delocalized among the atoms of the conjugated system in alternating positions (only one mesomeric structure Ij is shown);

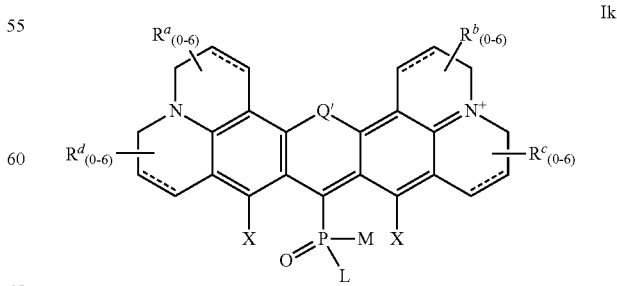

wherein the substituents L and M are defined as above,
Q' and X are defined as for formula Ia above, $R^a$, $R^b$, $R^c$ and $R^d$ are independently selected from H and $R^3$, where $R^3$ is defined as above, and the positive charge is delocalized among the atoms of the conjugated system in alternating positions (only one mesomeric structure Ik is shown);

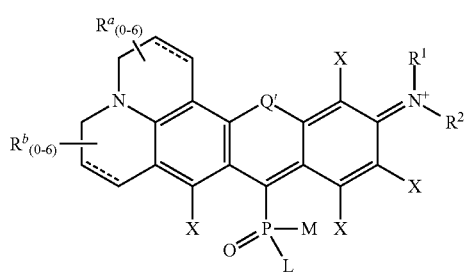

Il wherein the substituents L, M, $R^1$ and $R^2$ are defined as above,

Q' and X are defined as for formula Ia above, $R^a$ and $R^b$ are independently selected from H and $R^3$, where $R^3$ is defined as above, and the positive charge is delocalized among the atoms of the conjugated system in alternating positions (only one mesomeric structure Il is shown);

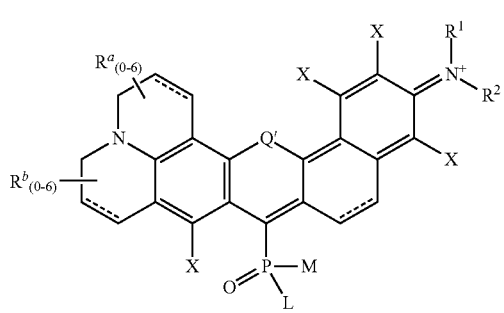

Im wherein the substituents L, M, $R^1$ and $R^2$ are defined as above,

Q' and X are defined as for formula Ia above, $R^a$ and $R^b$ are independently selected from H and $R^3$, where $R^3$ is defined as above, and the positive charge is delocalized among the atoms of the conjugated system in alternating positions (only one mesomeric structure Im is shown);

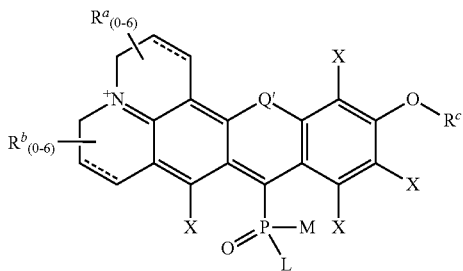

In wherein the substituents L and M are defined as above,

Q' and X are defined as for formula Ia above, $R^a$, $R^b$ and $R^c$ are independently selected from H and $R^3$, where $R^3$ is defined as above, and the positive charge is delocalized among the atoms of the conjugated system in alternating positions (only one mesomeric structure In is shown);

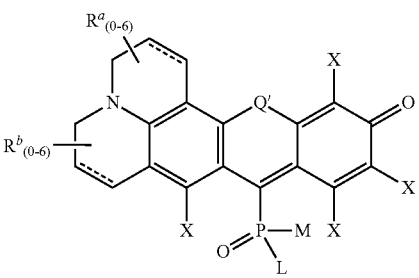

Io wherein the substituents L and M are defined as above,

Q' and X are defined as for formula Ia above, $R^a$ and $R^b$ are independently selected from H and $R^3$, where $R^3$ is defined as above;

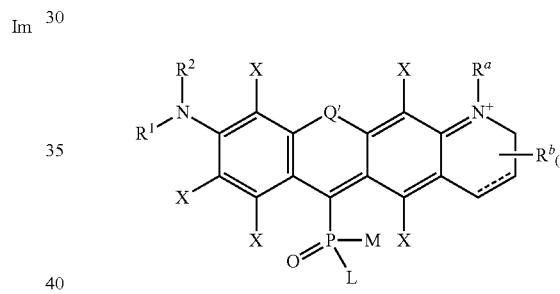

Ip wherein the substituents L and M are defined as above,

Q' and X are defined as for formula Ia above, $R^a$ and $R^b$ are independently selected from H and $R^3$, where $R^3$ is defined as above, and the positive charge is delocalized among the atoms of the conjugated system in alternating positions (only one mesomeric structure Io is shown);

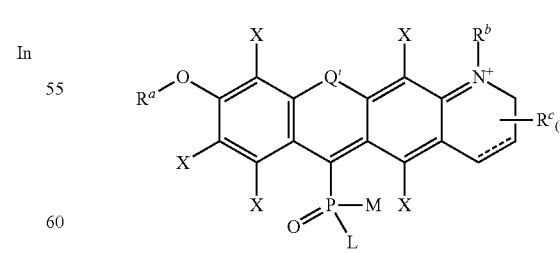

Iq wherein the substituents L and M are defined as above,

Q' and X are defined as for formula Ia above, $R^a$, $R^b$ and $R^c$ are independently selected from H and $R^3$, where $R^3$ is defined as above, in particular

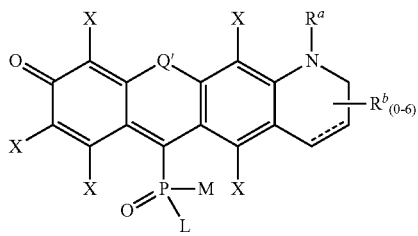

wherein the substituents L and M, Q' and X are defined as above,

R$^a$ and R$^b$ are independently selected from H and R$^3$, where R$^3$ is defined as above, and the positive charge is delocalized among the atoms of the conjugated system in alternating positions (only one mesomeric structure Iqa is shown);

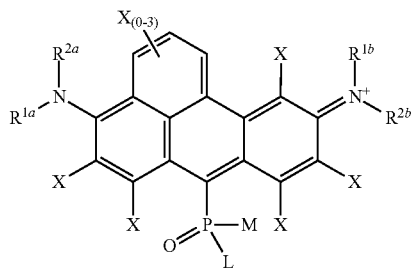

wherein the substituents L and M are defined as above,

X are defined as for formula Ia above,

R$^{1a}$ and R$^{2a}$ can represent H, alkyl, aryl or heteroaryl, and wherein R$^{1a}$ and R$^{2a}$ can form together a substituted or unsubstituted 4-7 membered ring, R$^{1b}$ and R$^{2b}$ can represent H, alkyl, aryl or heteroaryl, and wherein R$^{1b}$ and R$^{2b}$ can form together a substituted or unsubstituted 4-7 membered ring, and the positive charge is delocalized among the atoms of the conjugated system in alternating positions (only one mesomeric structure Ir is shown);

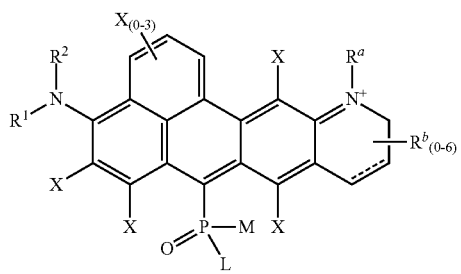

wherein the substituents L and M are defined as above,

X are defined as for formula Ia above,

R$^a$ and R$^b$ are independently selected from H and R$^3$, where R$^3$ is defined as above, R$^1$ and R$^2$ can represent H, alkyl, aryl or heteroaryl, and wherein R$^1$ and R$^2$ can form together a substituted or unsubstituted 4-7 membered ring, and the positive charge is delocalized among the atoms of the conjugated system in alternating positions (only one mesomeric structure Is is shown).

In some specific embodiments of the compounds represented by formula I, in particular represented by any one of formulae Ia-s, a COOR$^1$ group is present in form of an active ester COOR$^4$, in particular with R$^4$=N-succinimidyl, N-phthalimidyl, N-tetrachlorphthalimidyl, pentachlorophenyl, pentafluorophenyl, 2,3,5,6-tetrafluorophenyl, 4-(hydroxysulfonyl)-2,3,5,6-tetrafluorophenyl [p-(HOSO$_2$)C$_6$F$_4$], 1-benzotriazolyl, cyanomethyl.

In some specific embodiments of the compounds represented by formula I, in particular represented by any one of formulae Ia-s, a OR$^1$ group represents an active carbonate ester OCOOR$^4$, in particular with R$^4$=N-succinimidyl, N-phthalimidyl, N-tetrachlorphthalimidyl, pentachlorophenyl, pentafluorophenyl, 2,3,5,6-tetrafluorophenyl, 4-(hydroxysulfonyl)-2,3,5,6-tetrafluorophenyl [p-(HOSO$_2$)C$_6$F$_4$], 1-benzotriazolyl, cyanomethyl.

Still more specific embodiments of the compounds represented by formula I, in particular represented by any one of formulae Ia-s, have a structural formula selected from:

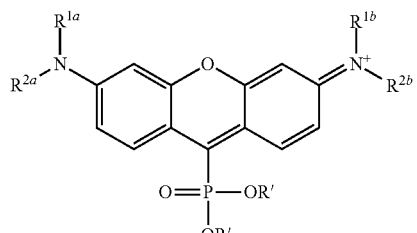

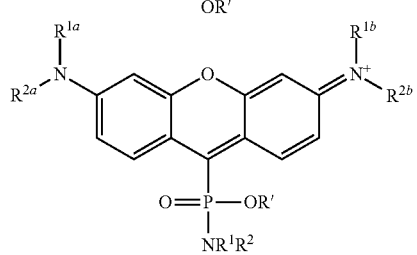

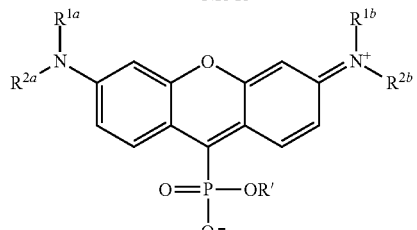

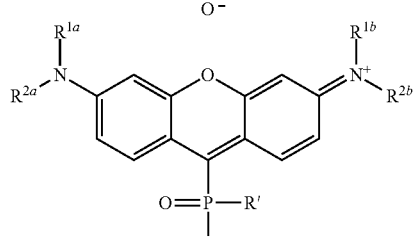

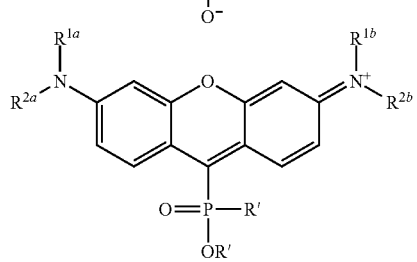

-continued
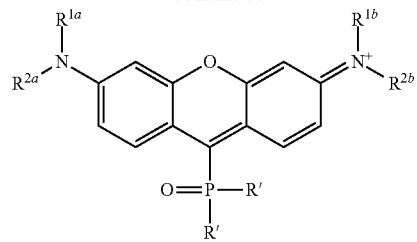
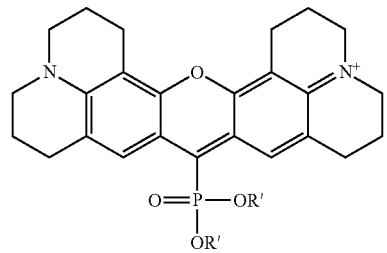
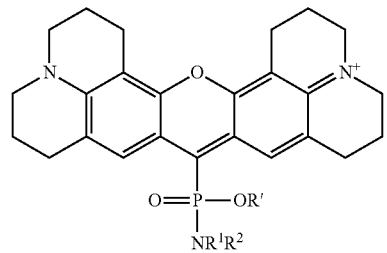
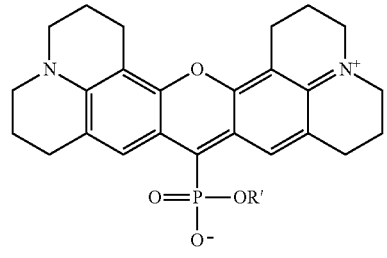
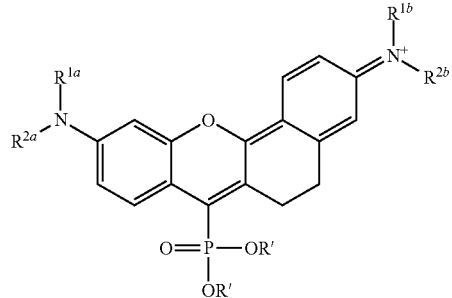
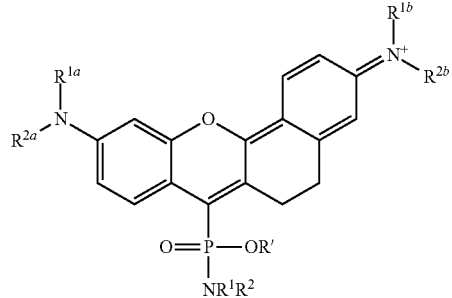
-continued
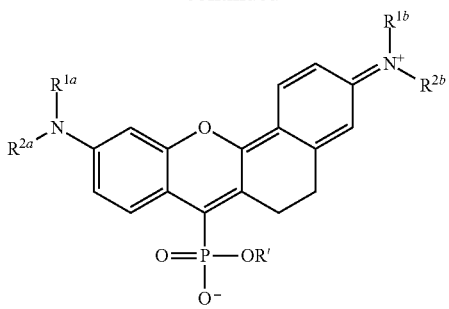
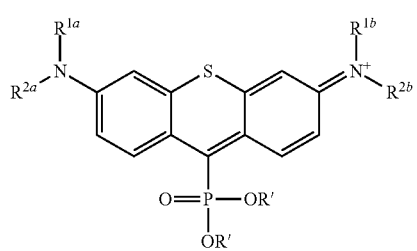
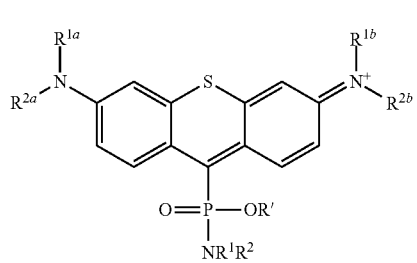
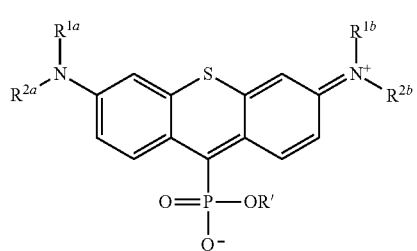
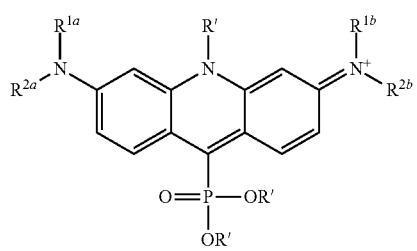
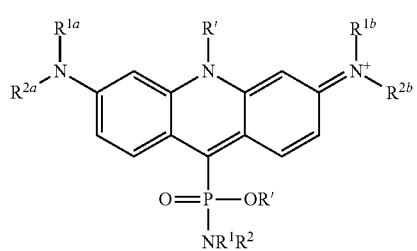

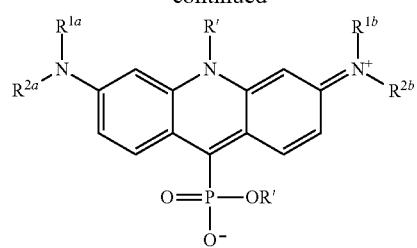
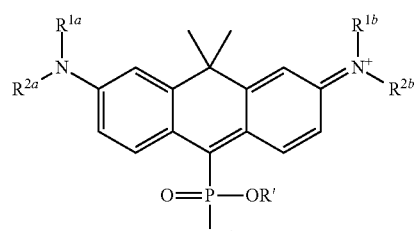
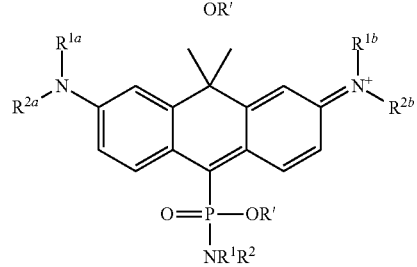
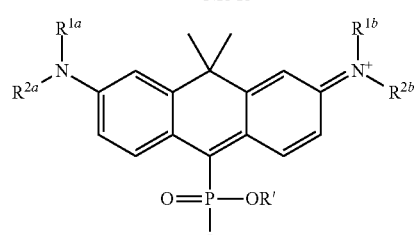
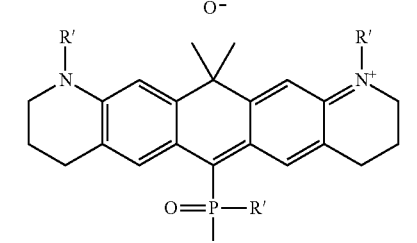
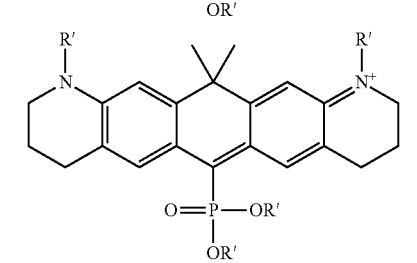
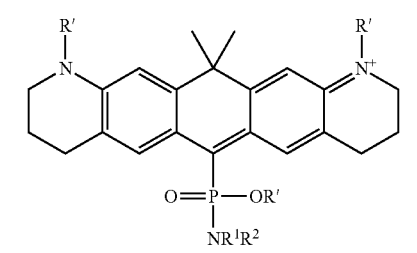
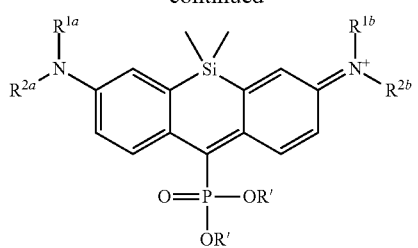
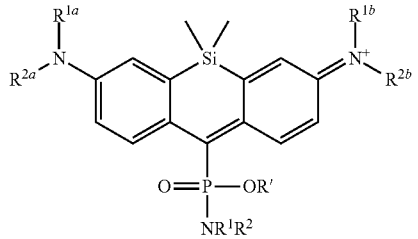
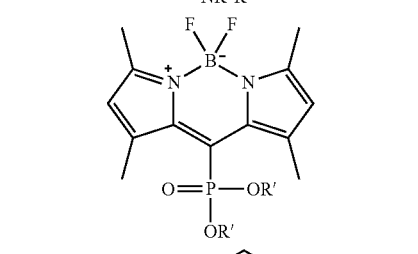
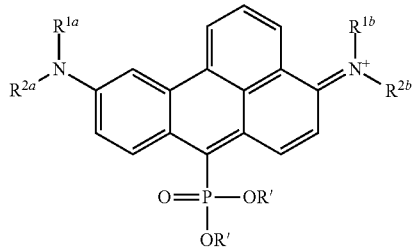
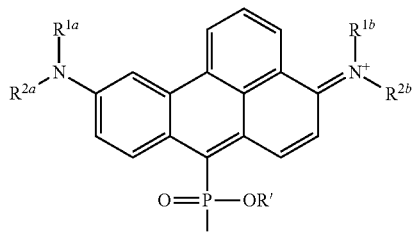
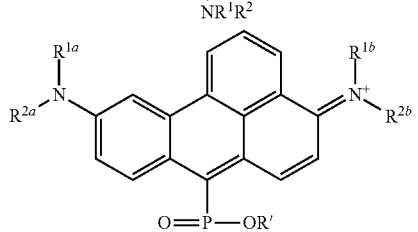
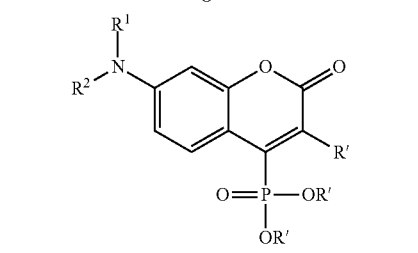

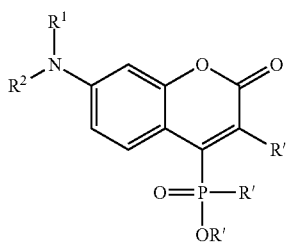
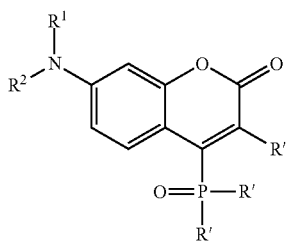
wherein the substituents R¹, R², $R^{1a}$, $R^{2a}$, $R^{1b}$, $R^{2b}$, R' are defined as above.
Further more specific embodiments of the compounds represented by formula I, in particular represented by any one of formulae Ia-s, have a structural formula selected from:
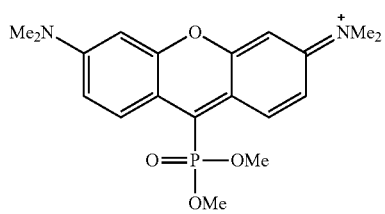
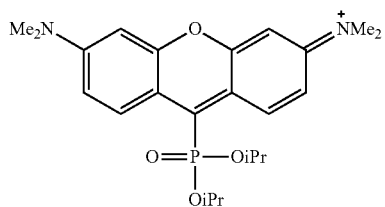
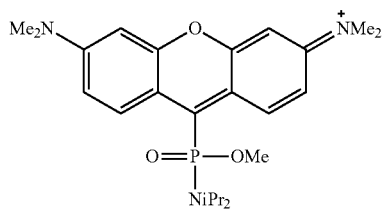
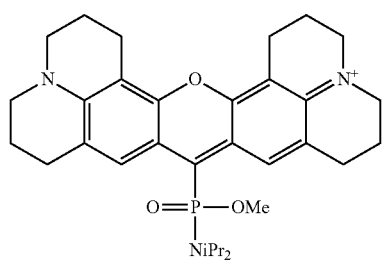
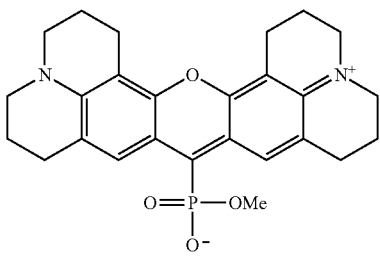
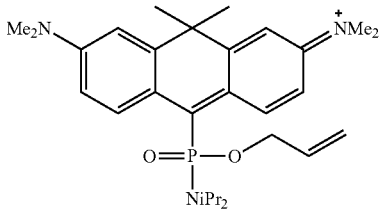
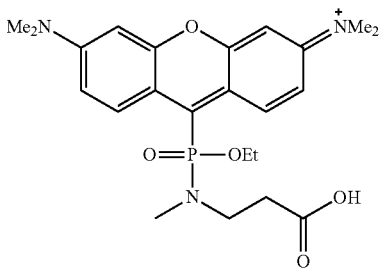

-continued
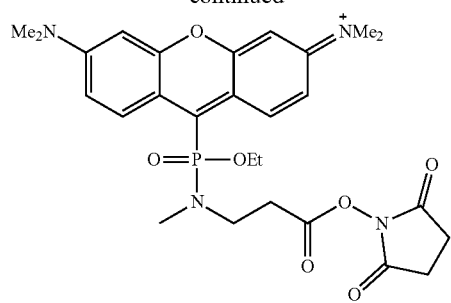
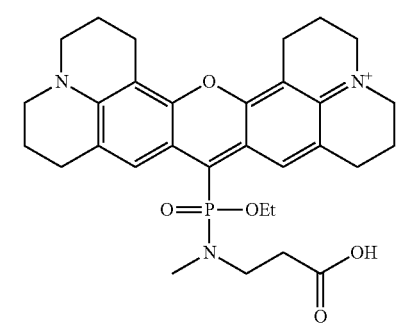
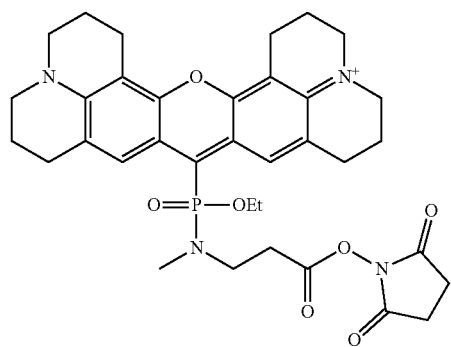
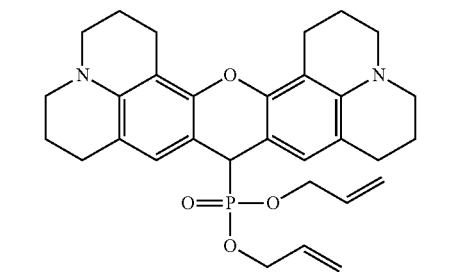
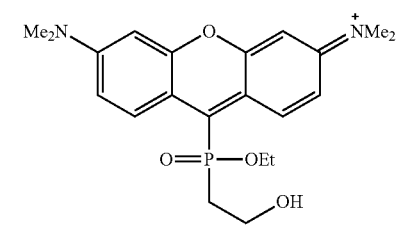
-continued
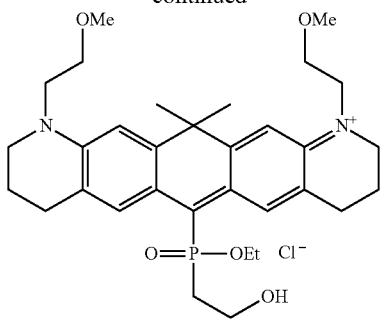
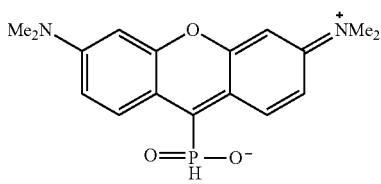
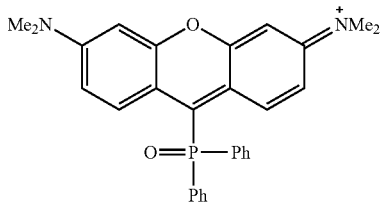
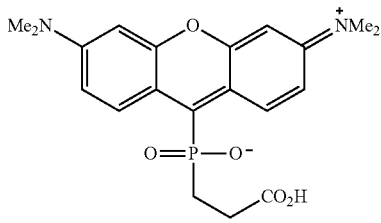
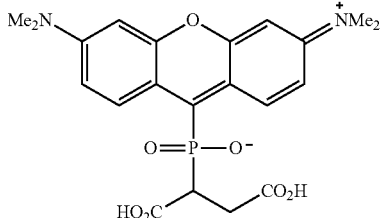
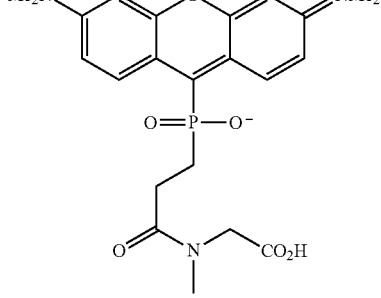

21
-continued
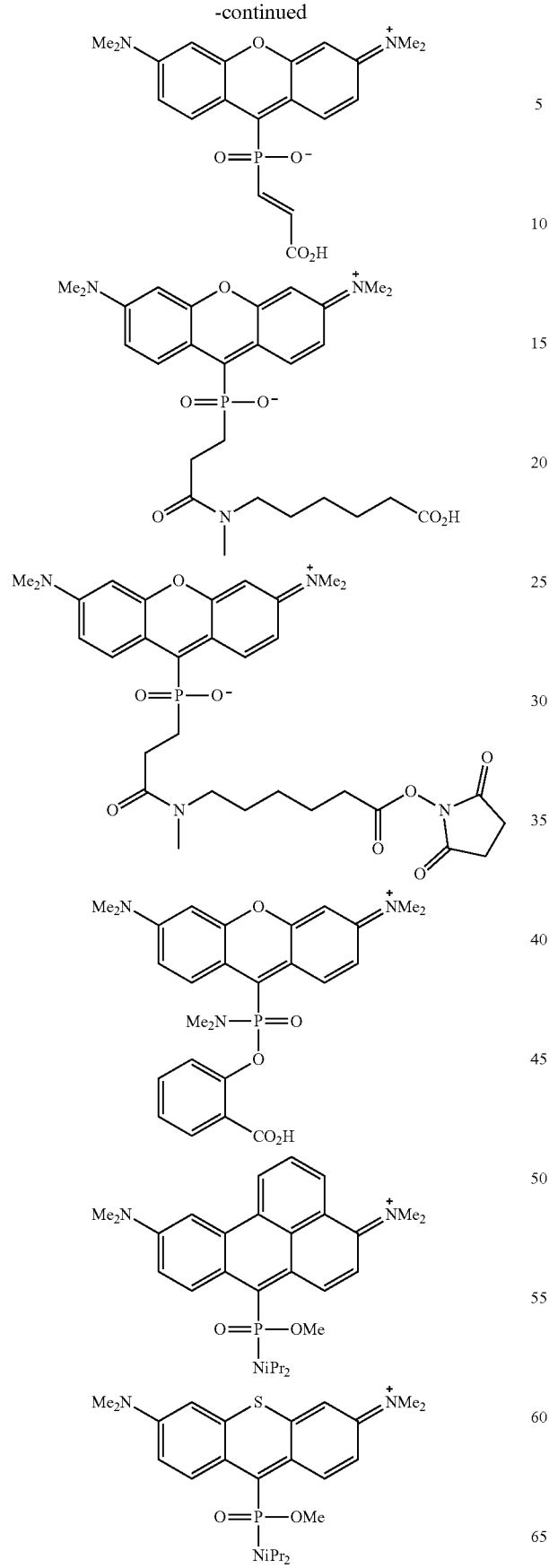
22
-continued
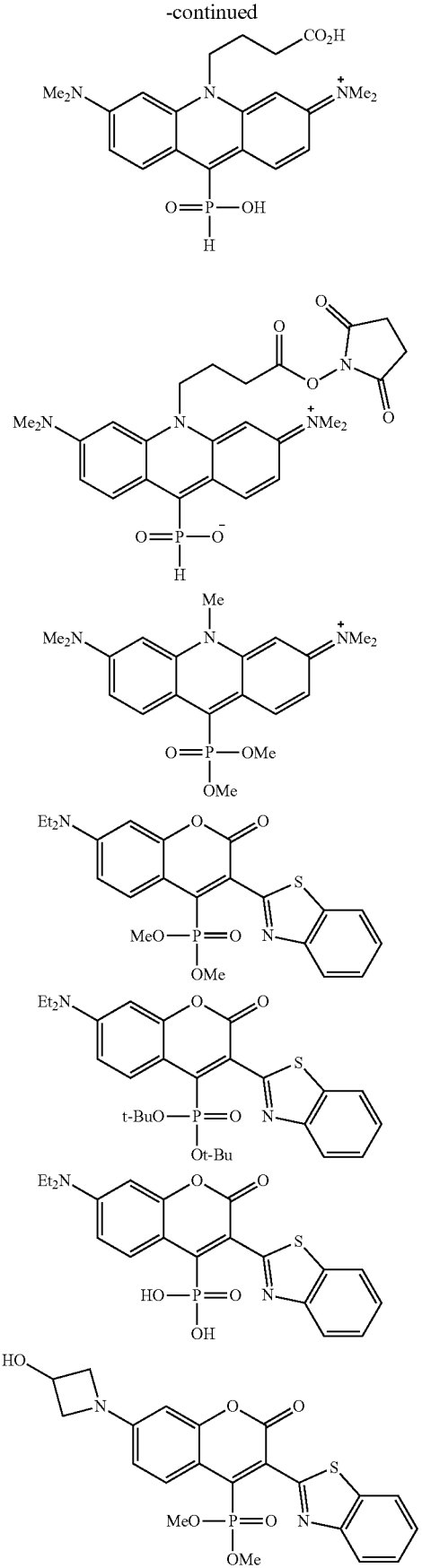

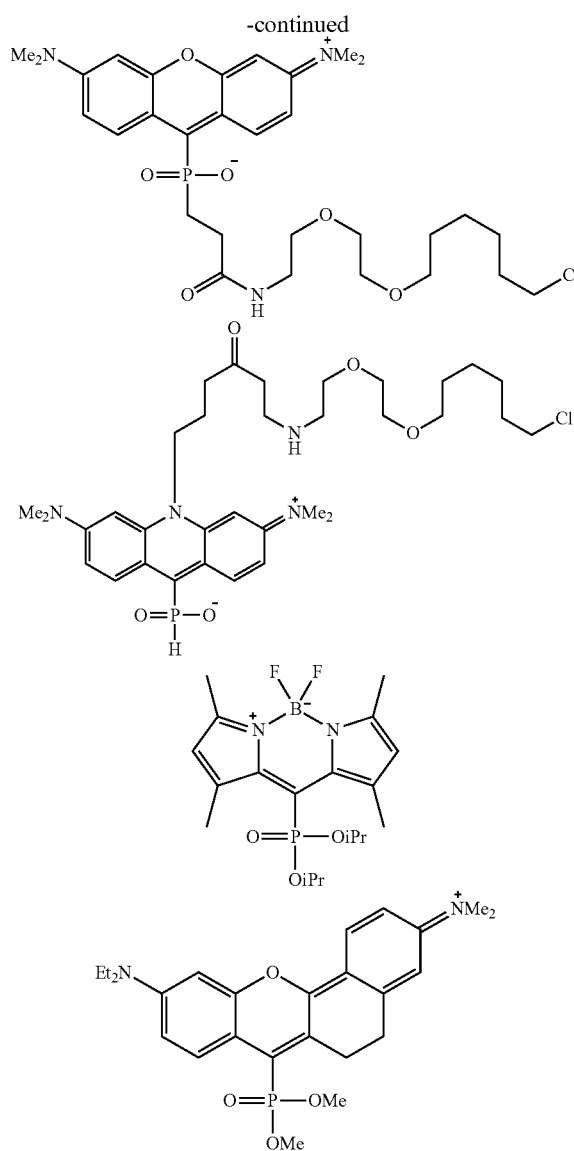

Definitions

The term "substituted" as used herein is understood to include all permissible substituents of organic compounds, provided a) that such substitution is in accordance with permitted valence of the substituted atom and the substituent and b) that the substitution results in a compound sufficiently stable to perform under the conditions practical for the disclosed method, that is that a compound does not spontaneously undergo transformation such as by rearrangement, fragmentation, elimination, hydrolysis etc. long enough to practically perform as disclosed herein. In a broad aspect, the permissible substituents include acyclic and cyclic, branched and unbranched, carbocyclic and heterocyclic, aromatic and nonaromatic, neutral, positively and negatively charged substituents of organic compounds and combinations thereof. Unless stated otherwise, all chemical groups described herein include both unsubstituted and substituted varieties.

It should be understood that the bond types and locations in the chemical structures provided herein may adapt depending on the substituents in the compound, even if not specifically recited. For instance, —Z— where Z can be $CR_{(2)}$ or N(R) can be understood as —CR═, —CHR—, —CR$_2$—, —N═, —NH— or —NR—. Thus, even if not specifically illustrated, the chemical compounds described herein include any hydrogen atoms, lone pair of electrons and charges necessary for completing a chemical structure according to valence rules. This may include charges appearing in drawn mesomeric forms (e.g., —CR$^+$— instead of —CR═, —N$^-$— instead of —N═ etc.) or tautomeric forms of the same chemical entity.

A sesquialteral bond (i.e. a bond drawn as having an order between one and two) is to be understood as a single or double bond as necessary to complete a chemical structure, or either of two if both options are possible considering the implied hydrogens, lone pairs and charges as described above. Six sesquialteral bonds in a six-membered ring denote a planar carbocycle or heterocycle, wherein a combination of alternating single and double is conventionally used to depict aromaticity or conjugation of double bonds in non-aromatic fragments. It is understood that the structures that are alternative drawings of the same chemical entities (mesomeric or tautomeric forms with different charge localizations or charge separations) as well as having hydrogen atoms added or subtracted to form protonated or deprotonated forms of the claimed structures are also expressly claimed.

A dashed arc in a general structure is meant to describe an optional fused cycle (i.e. a cycle connected to the drawn core structure via two separate bonds), where the said cycle can be saturated or unsaturated, carbocyclic and heterocyclic, aromatic and nonaromatic, neutral, positively or negatively charged and can be substituted as described above in the most general sense. The most typical sizes of such fused cycles in the claimed structures are 5-, 6- and 7-membered, but the size of a fused cycle is not intended to be limited in any manner.

The term "heteroaryl" as used herein refers to an unsubstituted or substituted cyclic aromatic radical having from 5 to 10 ring atoms of which at least one ring atom is selected from S, O and N; the radical being joined to the rest of the molecule via any of the ring atoms. Representative, but not limiting examples are pyridinyl, pyrazinyl, pyrimidinyl, pyrrolyl, imidazolyl, thiazolyl, benzothiazolyl, oxazolyl, benzoxazolyl, isooxazolyl, thiadiazolyl, thienyl, furyl, quinolinyl and isoquinolinyl.

The term "halogen" as used herein is referred to fluorine, chlorine, bromine or iodine.

The term "alkenyl" as used herein is a hydrocarbon group of from 2 to 20 carbon atoms with a structural formula containing at least one carbon-carbon double bond. The term is inclusive of linear and cycle-containing (i.e., cycloalkenyl) groups. Asymmetric structures, such as $(A^1A^2)C$═$C(A^3A^4)$, where at least one of the substituents $A^1,A^2$ is not H and at least one of the substituents $A^3,A^4$ is not H, are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, optionally substituted alkyl, cycloalkyl, alkoxy, alkenyl, cycloalkenyl, alkynyl, cycloalkynyl, ester, ether, halide, cyano, hydroxy, ketone, azide, silyl, sulfonyl, sulfide or thiol, in the broadest sense applicable.

The term "aryl" as used herein is a group that contains any carbon-based aromatic group including, but not limited to, benzene, naphthalene, phenyl, biphenyl, phenoxybenzene, and the like. The term "aryl" also includes "heteroaryl", which is defined as a group that contains an aromatic group that has at least one heteroatom incorporated within the ring of the aromatic group. Examples of heteroatoms include, but are not limited to, nitrogen, oxygen, sulfur and phosphorus. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, ester, ether, nitro, halide, cyano, hydroxy, ketone, azide, silyl, sulfonyl, sulfide or thiol, in the most broad sense applicable. The term "biaryl" is a specific type of aryl group and is included in the definition of "aryl". Biaryl refers to two aryl groups that are bonded together via a fused ring structure, as in naphthalene, or are attached via one or more carbon-carbon bonds, as in biphenyl.

The term "alkynyl" as used herein is a hydrocarbon group of from 2 to 20 carbon atoms with a structural formula containing at least one carbon-carbon triple bond. The term is inclusive of linear and cycle-containing (i.e., cycloalkynyl) groups. The alkynyl group can be substituted with one or more groups including, but not limited to, optionally substituted alkyl, cycloalkyl, alkoxy, alkenyl, cycloalkenyl, alkynyl, cycloalkynyl, ester, ether, halide, cyano, hydroxy, ketone, azide, silyl, sulfonyl, sulfide or thiol, in the broadest sense applicable.

The terms "amine" or "amino" as used herein are represented by a formula $NA^1A^2A^3$ or a substituent $NA^1A^2$, where $A^1$, $A^2$ and $A^3$ can be, independently, hydrogen or optionally substituted alkyl, cycloalkyl, alkenyl, cycloalkenyl, alkynyl, cycloalkynyl, aryl or heteroaryl group as described herein. In specific embodiments amine refers to any of $NH_2$, NH(alkyl), NH(aryl), N(alkyl)$_2$, N(aryl)$_2$ or N(alkyl)(aryl).

Unless defined otherwise, all technical and scientific terms used herein have the same meaning as commonly understood by a person skilled in the art to which the subject matter disclosed herein belongs. The procedures and methods disclosed herein are purely representative, and any methods, devices or materials similar or alternative to those described in preparation, testing or application of the presently-disclosed subject matter may be employed in practice.

All numbers expressing quantities of ingredients and properties such as reaction conditions (reaction time, temperature etc.) are to be understood as being modified in all instances by the term "about", and the numerical parameters set forth in the specification and claims are approximations that can vary according to the desired properties sought to be obtained by the presently-disclosed subject matter. As used herein, the term "about", referring to a value or to an amount such as mass, weight, volume, time, concentration or percentage (e.g., catalyst loading), is meant to encompass variations of in some embodiments ±20%, in some embodiments ±10%, in some embodiments ±5%, in some embodiments ±1%, in some embodiments ±0.5% and in some embodiments ±0.1% from the specified amount, whenever such variations are appropriate to perform the disclosed method.

All ranges expressed as from one particular value to another particular value are to be understood as meant from "about" one particular value to "about" another particular value. Each value is disclosed as "about" that particular value in addition to the value itself, and each unit between two particular disclosed units is also to be considered disclosed.

General Approach for Synthesizing the Novel Compounds, in Particular Fluorescent Dyes, of the Invention The present inventors have found that many organic dyes with cationic conjugated systems react with nucleophilic phosphorus reagents—phosphinic (hypophosphorous) acid ($H_3PO_2$), phosphinites [ROPR'$_2$], phosphonites [(RO)$_2$PR'], phosphites [(RO)$_3$P] or phosphoramidites [(RO)$_2$PNR'$_2$]. Delocalization of a positive charge across the conjugated system (and adjacent heteroatoms) is not uniform and such an extended delocalization makes both the cationic and the neutral electrophilic dyes in Scheme 1 below behave as soft electrophiles. According to the Pearson acid/base concept, trimethyl phosphite [(MeO)$_3$P], a typical nucleophilic phosphorus reagent, acts as a soft nucleophile. [R. G. Pearson, H. Sobel, J. Songstad, *J. Am. Chem. Soc.* 1968, 90, 319-326]. This quite general concept of "soft" (with high polarizability, delocalized charges, small frontier orbital gap) and "hard" (with low polarizability, condensed charges and large frontier orbital gap) reagents predicts that soft electrophilic species preferably react with soft, but not with hard, nucleophiles. This preference can be explained by invoking the concept of orbital control in the reactions between soft nucleophiles and electrophiles, as opposed to charge-controlled reactions between hard reaction partners. Indeed, the inventors observed that soft phosphorus nucleophiles attacked the dyes of classes listed in Table 1 exclusively at the carbon atom with the highest contribution of atomic p-orbital to the LUMO of the dye. However, it must be noted that the Pearson concept only indicates the principal possibility of the reaction between soft electrophiles (cationic or neutral electrophilic dyes) and soft nucleophiles (nucleophilic trivalent phosphorus reagents), but it does not predict the structures, properties and usefulness of the products.

Scheme 1.
Nucleophilic addition of phosphinic acid (H$_3$PO$_2$), phosphinites [ROPR'$_2$], phosphonites [(RO)$_2$PR'],
phosphites [(RO)$_3$P] or phosphoramidites [(RO)$_2$PNR'$_2$] to cationic dyes (Dye 1) followed by fragmentation of the phosphonium
intermediate (Michaelis-Arbuzov reaction) and oxidation results in new red-shifted dyes (Dye 2) decorated with phosphinate, phosphonate or
phosphonamide groups (with a proposed abbreviation "PONy dyes").

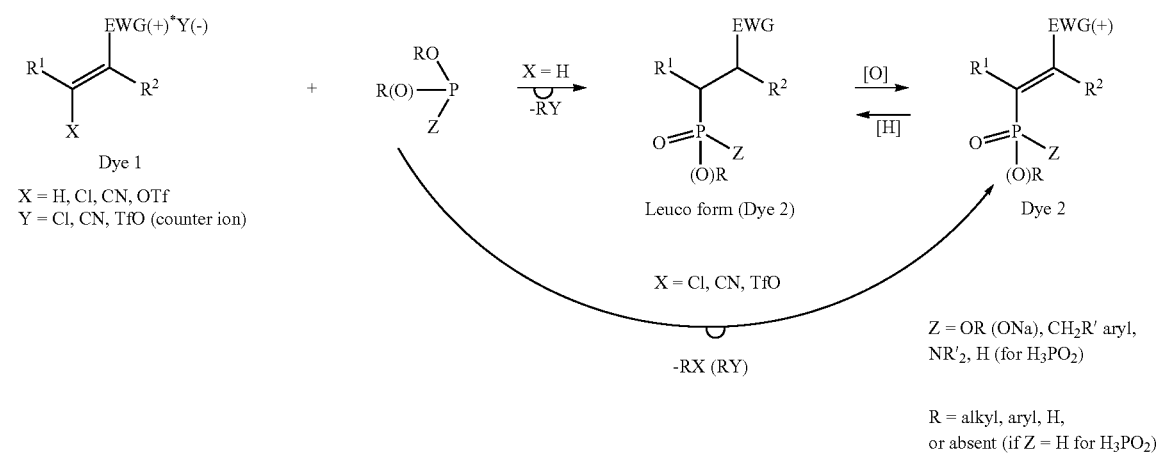

EWG = electron-withdrawing group

TABLE 1

| Dye | LUMO 3D isosurface (highest atomic contributions to LUMO) |
|---|---|
| 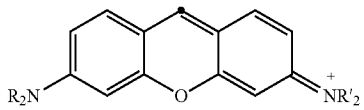 pyronine | See FIG. 3A |
| 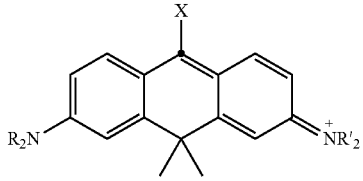 carbopyronine (X = H, CF$_3$SO$_3$) | See FIG. 3B |
|  Si-pyronine | See FIG. 3C |
| 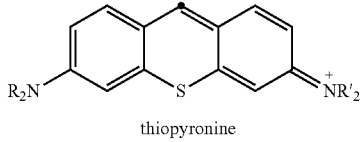 thiopyronine | See FIG. 3D |

TABLE 1-continued

| Dye | LUMO 3D isosurface (highest atomic contributions to LUMO) |
|---|---|
| 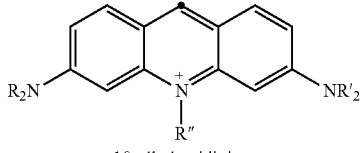 10-alkylacridinium | See FIG. 3E |
| 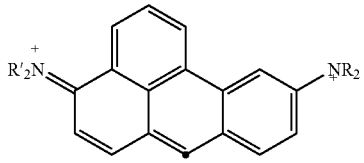 4,10-bis(dimethylamino)-7H-benzo[de]anthracen-7-ylium | See FIG. 3F |
| 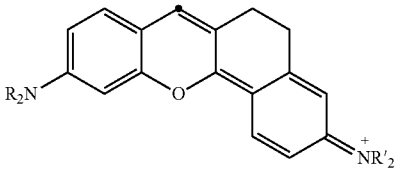 benzopyrylium | See FIG. 3G |
| 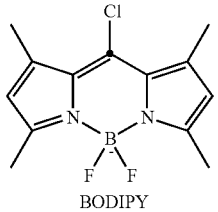 BODIPY | See FIG. 3H |
| 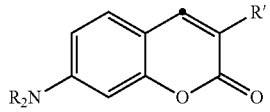 coumarin (reacts with $(R''O)_2PO^-Na^+$) e.g., $R' = $ 2-benzothiazolyl: 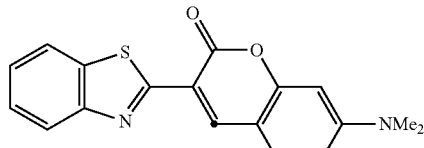 | See FIG. 3I |

Sample electrophilic dyes capable of reacting with phosphinic acid ($H_3PO_2$), phosphinites [$ROPR'_2$], phosphonites [$(RO)_2PR'$], phosphites [$(RO)_3P$] or phosphoramidites [$(RO)_2PNR'_2$] according to Scheme 1. These nucleophilic phosphorus reagents attack selectively at the carbon atoms marked with black dots. Calculated with Gaussian 09 (revision E.01) at the B2LYP/6-31G* level of theory [M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burrant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford CT, 2013].

Scheme 2.

Examples of phosphorus reagents capable of reacting with electrophilic fluorophores according to Scheme 1: phosphinic acid ($H_3PO_2$), phosphinites [$ROPR'_2$], phosphonites [$(RO)_2PR'$], phosphites [$(RO)_3P$], or phosphoramidites [$(RO)_2PNR'_2$].

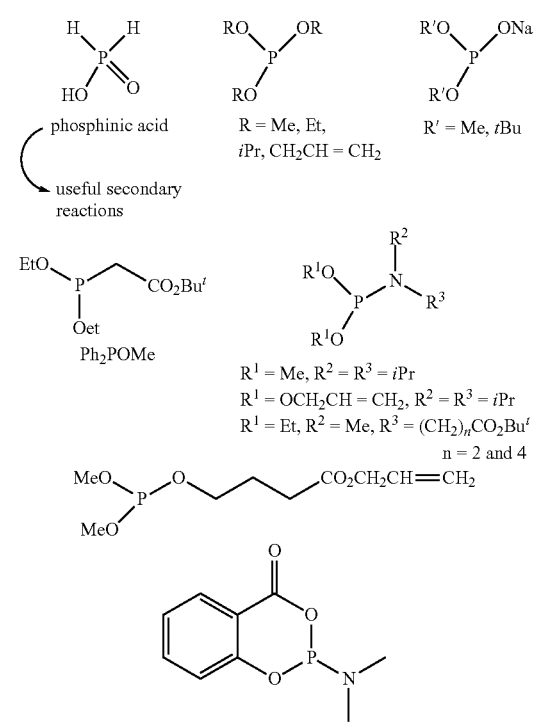

The present inventors successfully introduced the Michaelis-Arbuzov reaction of the electron deficient cationic dyes (and neutral coumarins, behaving as Michael acceptors in Michaelis-Becker modification of the Michaelis-Arbuzov reaction) with trivalent phosphorus nucleophiles (Scheme 1) towards the synthesis of new fluorescent dyes. Various classes of cationic dyes were shown to participate in this new transformation. Dye 1 in Scheme 1 may represent a pyronine, a benzopyrylium dye, a carbopyronine, its silicon-analogue (Si-pyronine), a thiopyronine, an N-alkylacridinium dye, a benzanthrylium dye {4,10-bis(dimethylamino)-7H-benzo[de]anthracen-7-ylium}, chlorinated BODIPY or even coumarin (for examples, see Table 1). The trivalent phosphorus nucleophiles include phosphinic acid ($H_3PO_2$), phosphinites [$ROPR'_2$], phosphonites [$(RO)_2PR'$], phosphites [$(RO)_3P$] and phosphoramidites [$(RO)_2PNR'_2$] (Scheme 2). This set includes synthetically useful phosphinylation and phosphonylation reagents with intention to illustrate the scope and limitations of the new synthetic method and to obtain practically useful fluorescent dye derivatives.

In most embodiments, the reactive form of a cationic dye (Dye 1) in Scheme 1 contains an electrophilic methine (=CH—) carbon atom and is termed henceforth a "CH compound" (Scheme 1, X=H). As a rule, the reactivity of "CH compounds" is sufficient. They readily react with phosphinic acid ($H_3PO_2$), phosphinites [$ROPR'_2$], phosphonites [$(RO)_2PR'$], phosphites [$(RO)_3P$] or phosphoramidites [$(RO)_2PNR'_2$] in organic solvents (or without solvent) at ambient or elevated temperatures (40-150° C.) providing leuco (colorless, reduced) forms of the new dyes (containing —CH($P^V$)— fragment, where $P^V$ is a substituted pentacovalent phosphorus) in the course of a nucleophilic addition to the electron-deficient C=C-bond followed by fragmentation of the tetracovalent phosphonium intermediate. [For reviews, see: a) R. Engel, "Phosphorus addition at $sp^2$ carbon", *Org. React.* 2004, 36, 175-248; b) A. K. Bhattacharya, G. Thyagarajan, "Michaelis-Arbuzov rearrangement", *Chem. Rev.* 1981, 81, 415-430.]

The rate of the reaction is significantly increased in the presence of a stoichiometric amount of an external nucleophile (preferably iodide), which increases the rate of the fragmentation by $S_N2$ substitution (Scheme 3). Oxidation of the leuco product, preferably with chloranil (tetrachloro-p-benzoquinone) or DDQ (2,3-dichloro-5,6-dicyanobenzoquinone), leads to the target red-shifted Dye 2:

Scheme 3. An example of the Michaelis-Arbuzov reaction of a cationic dye with an electrophilic methine group ("CH compound").

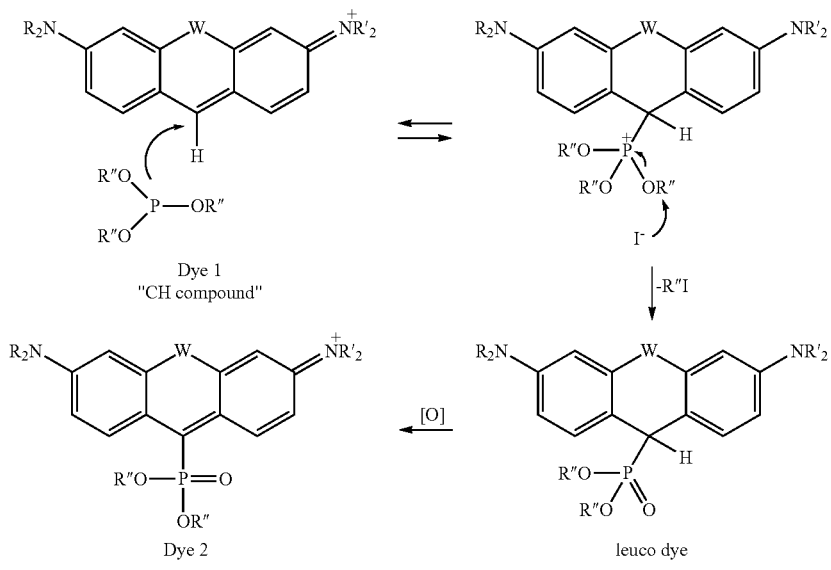

W — arbitrary bridging group (e.g., W = O, $CR_2$, $SiR_2$ etc.)

In some embodiments (e.g., for carbopyronine dyes), when the stronger activation of the dye component is preferred, a more reactive electrophilic halide of preferably triflate, termed henceforth a "CX compound" (e.g., X=CF$_3$SO$_3$; see carbopyronine dye in Table 1) prepared from the corresponding ketone may be advantageously employed instead of a "CH compound". In this case, the initial Dye 1 is present in a higher oxidation state, and, formally, the reaction (Dye 1→Dye 2) may be represented as a direct nucleophilic substitution (addition—elimination) at an sp$^2$ carbon with the triflate anion (CF$_3$SO$_3$(—)) acting as a very good leaving group (followed by the fragmentation). If, however, in the presence of an excess of phosphine reagent, Dye 2 is prone to reduction to its leuco form, an oxidation step is also required. It can be performed after isolation of the leuco form of Dye 2 or in situ by addition of a strong oxidizing agent (organic or inorganic); preferably chloranil (tetrachloro-p-benzoquinone) or DDQ (2,3-dichloro-5,6-dicyanobenzoquinone):

shifts). Thus, the transformation Dye 1→Dye 2 is accompanied by creation of unique novel structures possessing the following desirable properties:

1. a cationic (neutral in the case of a coumarin) Dye 1 is transformed into a zwitterionic (neutral or negatively charged coumarin) Dye 2 with a very short charge separation distance;
2. small molecular mass (not including counterions, molecular masses MW<500 are common) and compact structure;
3. bathochromic and bathofluoric shifts of absorption and emission bands;
4. additional functional groups (e.g., carboxylate groups for further conjugation) as a result of secondary reactions of phosphinic acid residue or substituents in phosphinites [ROPR'$_2$], phosphonites [(RO)$_2$PR'], phosphites [(RO)$_3$P] or phosphoramidites [(RO)$_2$PNR'$_2$];

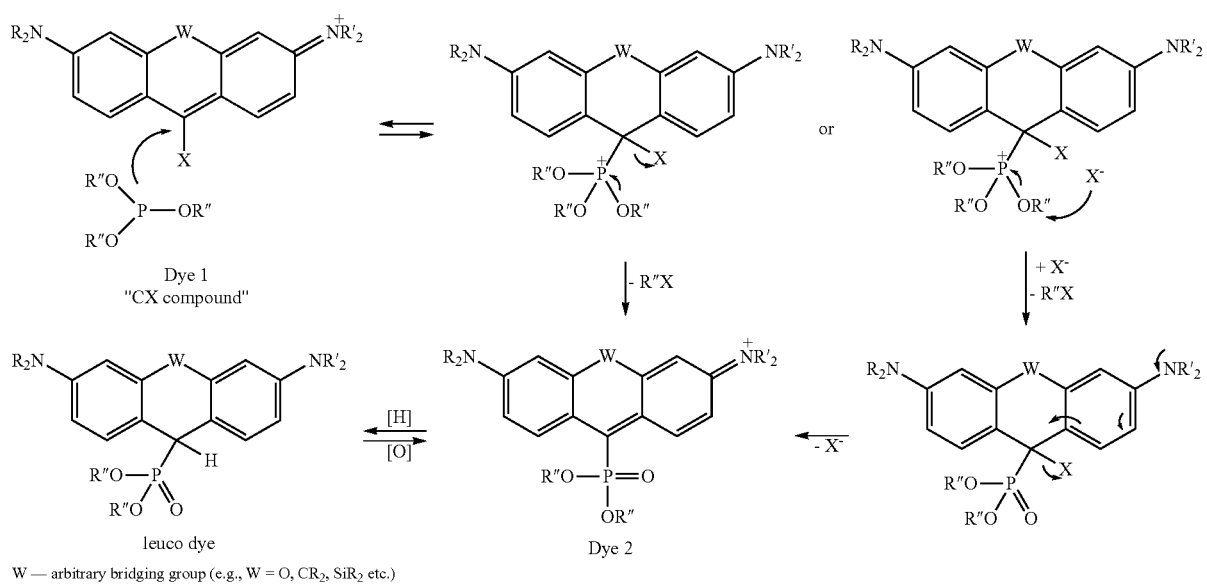

Scheme 4. An example of the Michaelis-Arbuzov reaction of a cationic dye with a reactive halide or triflate group ("CX compound").

General Characteristics of the Novel Compounds, in Particular Fluorescent Dyes, of the Invention The structures of initial dyes (Dye 1) and trivalent nucleophilic phosphorus species may be varied with a high degree of freedom (for examples, see Table 1 and Scheme 2). Two variables and the possibility of useful secondary reactions in the case of phosphinic acid and functionally substituted phosphites and phosphoramidites (see Scheme 2 and Examples) highlight the versatility of the claimed transformation, which always results in a new dye decorated with a phosphinate, phosphonate or phosphonamidate group (Dye 2) and demonstrating bathochromic and bathofluoric shifts as compared to the starting dye. In other words, the absorption and emission maxima of Dye 2 are shifted to longer wavelengths compared with the absorption and emission bands of Dye 1. Moreover, the Stokes shift (separation between the maxima of the emission and absorption bands) of Dye 2 is larger than the Stokes shift of Dye 1 (even in the case of coumarin dyes, which initially have long Stokes 5. increased Stokes shifts (with sufficient emission efficiency).

The changes in properties mentioned above are consequential for the applicability and performance of the new fluorescent markers in biology-related optical microscopy. Generally, the cationic dyes may be used as staining reagents for cell organelles. However, electroneutral, zwitterionic and sometimes negatively charged markers are advantageous. The positively charged (cationic) fluorophores may provide highly unspecific staining and increase the undesired background emission in living and fixed cells (i.e. dead cells with preserved morphology). In live cells, some cationic dyes demonstrate toxicity due to off-target binding (e.g, with nuclear DNA). Cell membrane-impermeant anionic dyes find their use in labeling the targets of interest on the outer plasma membrane. For intracellular labelling, neutral or zwitterionic dyes with short charge separation distance are preferred, especially if penetration of intact (non-permeabilized) cell membrane of live cells is required. As an empirical rule, cell-permeant probes are preferably neutral (or zwitterionic with a short charge separation distance and a zero net charge), possess a compact structure, limited molecular mass (M<800 Da), and several heteroatoms as hydrogen bond donors and acceptors. [Butkevich, A. N.; Mitronova, G. Y.; Sidenstein, S. C.; Klocke, J. L.; Kamin, D.; Meineke, D. N. H., D'Este, E.; Kraemer, P. T.; Danzl, J. G.; Belov, V. N.; Hell, S. W. *Angew. Chem. Int. Ed.* 2016, 55, 3290-3294] In this respect, Dyes 2 in Scheme 1 (see also structures of individual dyes in Examples) offer the unique advantage of creating a negative charge on the oxygen atom attached to phosphorus (in phosphinates, phosphonates and phosphonamidates, Z=O(—)). As the positively charged aromatic system is directly attached to the same phosphorus atom, the densely packed structure features the shortest possible charge separation distance (with one atom of phosphorus between charged residues). Indeed, the dyes belonging to this new class of fluorophores were shown to be cell-permeant and to selectively stain intracellular structures.

The bathofluoric shift in Dyes 2 provides emission maxima in the red to near IR spectral region, which is of particular value for biology-related microscopy due to lower autofluorescence and deeper light penetration, especially in an intact specimen. The red and near IR light is less phototoxic for live cells, as it induces less photochemical damage to the biomolecular constituents of cell components and tissues. Therefore, the red-emitting dyes of the present invention represent promising fluorescent markers for life sciences, in particular for multicolor applications. All reported live cell-compatible rhodamines, carborhodamines or Si-rhodamines have demonstrated small Stokes shifts (≤30 nm) [A. Butkevich et al.; see ref. above, and references cited therein]. However, for satisfactory color separation in fluorescent microscopy available multicolor imaging schemes require the combination of fluorescent dyes with small and large Stokes shifts. For example, three-color STED imaging has been demonstrated by combining two dyes with small Stokes shifts and one dye with a large Stokes shift in fixed samples using immunolabeling. [Sidenstein, S. C.; D'Este, E.; Böhm, M.; Danzl, J. G.; Belov, V. N.; Hell, S. W. *Sci. Rep.* 2016, 6, 26725] For three-color live super-resolution microscopy, cell-permeant large Stokes shift dyes suitable for living cells (with Stokes shifts in the range of 80-200 nm) are required. These dyes were unavailable prior to the present invention.

Methods of Synthesis

A further aspect of the present invention relates to methods for preparing the compounds of the invention as described above.

In particular, one method for preparing the compounds or conjugates according to the present invention comprises the following steps:

a) Reacting of a precursor compound, wherein a group P(=O)LM as defined in the above claims is replaced with either a hydrogen atom or a reacting group selected from the following: CN, Cl, Br, I, triflate (OTf), nonaflate (ONf) or other sulfonyloxy (OSO$_2$R) group (preferably triflate) with phosphinic (hypophosphorous) acid H$_3$PO$_2$ or its esters H$_2$P(O)OR, phosphinites [R$^a$OPR$^b$R$^c$], phosphonites [(R$^a$O)(R$^b$O)PR$^c$], phosphites R$^c$OP(OR$^a$)(OR$^b$), phosphoramidites R$^c$R$^d$NP(OR$^a$)(OR$^b$), where R$^{a-d}$ are H, alkyl or aryl (preferably alkyl), or salts of the corresponding esters, where at least one of R$^{a-d}$ is a metal, preferably alkali metal (Li, Na, K, Rb, Cs), more preferably Na; the said reaction providing either directly a compound of claims 1-8, or an intermediate compound, such as a leuco form of a compound of claims 1-8, which can be isolated or used as crude material for the following step;

b) Optional alkylation of an intermediate phosphinic ester leuco derivative with an alkyl halide, alkyl sulfonate or a Michael acceptor, if step a) was performed with phosphinic (hypophosphorous) acid or its esters;

c) Oxidizing of the leuco intermediate into a dye of any of the formulae of claims 1-8 by oxidation with an organic or inorganic oxidant, or with an inorganic oxidant in the presence of catalytic amounts of an organic oxidant(s), or electrochemically, with or without subsequent acidic or basic hydrolysis;

d) Optionally performing post-synthetic modifications, in particular conjugation to protein ligands, introduction of reactive alkene or alkyne groups for (in situ) click reaction, preparation of active esters, in particular as defined in the Description of the Invention above.

In a more specific embodiment of said method, step a) is catalyzed by a nucleophilic catalyst, preferably with iodide of an organic or inorganic cation, more preferably tetrabutylammonium iodide.

The organic oxidant may be, e.g., selected from 2,3-dichloro-5,6-dicyano-1,4-benzoquinone (DDQ), 2,3,5,6-tetrachloro-1,4-benzoquinone (p-chloranil), 3,4,5,6-tetrachloro-1,2-benzoquinone (o-chloranil), or other quinones, preferably is DDQ, and/or the inorganic oxidant is selected from oxygen, ozone, hydrogen peroxide, iodine, periodate salts, Mn(OAc)$_3$, Pb(OAc)$_4$, PbO$_2$, K$_3$[Fe(CN)$_6$], preferably is sodium or tetrabutylammonium periodate.

In another specific embodiment of said method, step c) is performed in vitro or in vivo resulting in a detectable response, such as fluorescence intensity change, appearance or quenching of the fluorescence signal, for imaging, sensing or kinetic studies.

The presently-disclosed subject matter further includes general methods of producing compounds of type I or of structurally related compounds of type II below. Methods for synthesizing embodiments of the presently-disclosed compounds generally include one or more well-known synthesis steps. While certain embodiments of methods for synthesizing the present compounds are described herein, methods of synthesis should not be limited to the methods described herein, as methods for synthesis can include any methods that would be readily apparent to those skilled in the art.

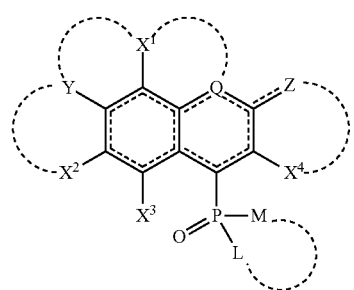

I

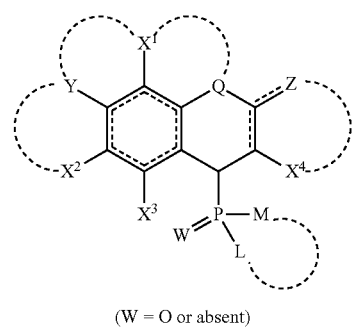

(W = O or absent)

In some embodiments, the compounds of type II can be prepared by nucleophilic addition of phosphinites, phosphonites, phosphites or phosphorimidates to appropriately substituted xanthylium, thioxanthylium, pyrylium, benzopyrylium, anthrylium, benzanthrylium or silaxanthylium salts, as shown in Scheme 5. In some embodiments, this reaction is catalyzed by addition of catalytic or stoichiometric amounts of inorganic or organic iodide salts, preferably tetrabutylammonium iodide. In some embodiments, the resulting leuco dyes II can be further oxidized to fluorescent dyes of type I in vivo or in vitro, for example by addition of a suitable oxidant (preferably DDQ).

Scheme 5

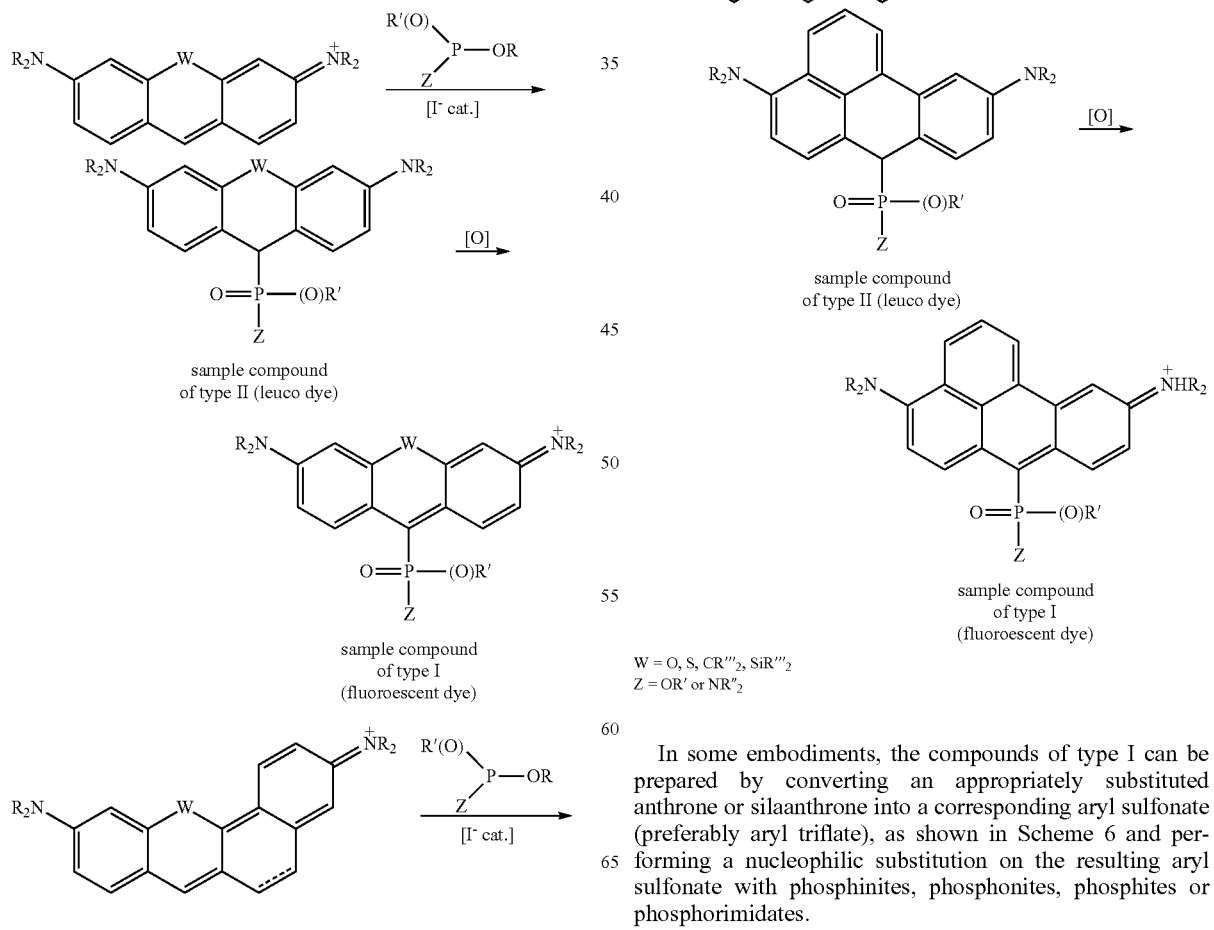

W = O, S, CR'''$_2$, SiR'''$_2$
Z = OR' or NR''$_2$

In some embodiments, the compounds of type I can be prepared by converting an appropriately substituted anthrone or silaanthrone into a corresponding aryl sulfonate (preferably aryl triflate), as shown in Scheme 6 and performing a nucleophilic substitution on the resulting aryl sulfonate with phosphinites, phosphonites, phosphites or phosphorimidates.

Scheme 6

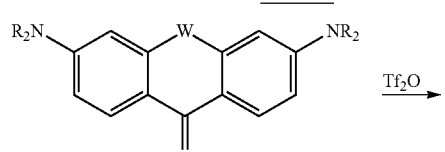

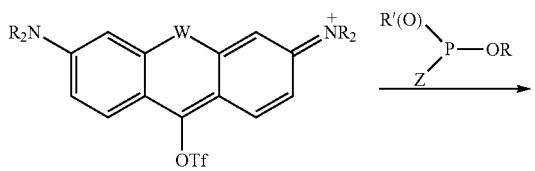

sample compound
of type I
(fluoroescent dye)

W = CR'''$_2$, SiR'''$_2$
Z = OR' or NR'$_2$

In some embodiments, the compounds of type II can be prepared by nucleophilic addition of phosphinic (hypophosphorous) acid $H_3PO_2$ to appropriately substituted acridinium or xanthylium salts, as shown in Scheme 7. In some embodiments, the resulting leuco dyes II can be further oxidized to fluorescent dyes of type I in vivo or in vitro, for example by addition of a suitable oxidant (preferably DDQ).

Scheme 7

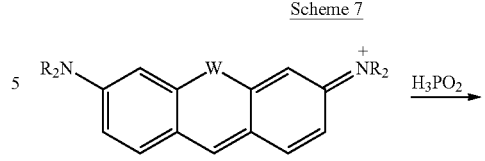

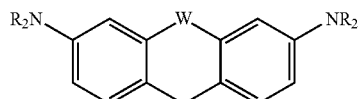

sample compound
of type II (leuco dye)

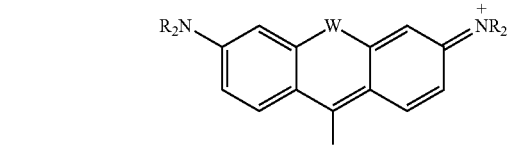

sample compound
of type I
(fluoroescent dye)

W = NR'$_2$, O

In some embodiments, the compounds of type II can be prepared by nucleophilic addition of phosphinic (hypophosphorous) acid $H_3PO_2$ to appropriately substituted acridinium or xanthylium salts, as shown in Scheme 8. In some embodiments, the resulting leuco dyes II can be converted to bis-silyl ethers followed by alkylation with an electrophilic alkyl halide or sulfonate or a Michael acceptor to yield leuco dyes II with a different substitution. In some embodiments, the resulting leuco dyes II can be further oxidized to fluorescent dyes of type I in vivo or in vitro, for example by addition of a suitable oxidant (preferably DDQ).

Scheme 9

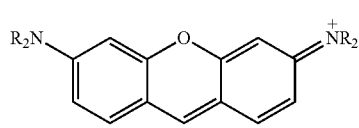

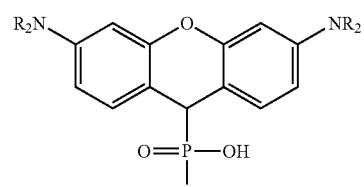

sample compound
of type II (leuco dye)

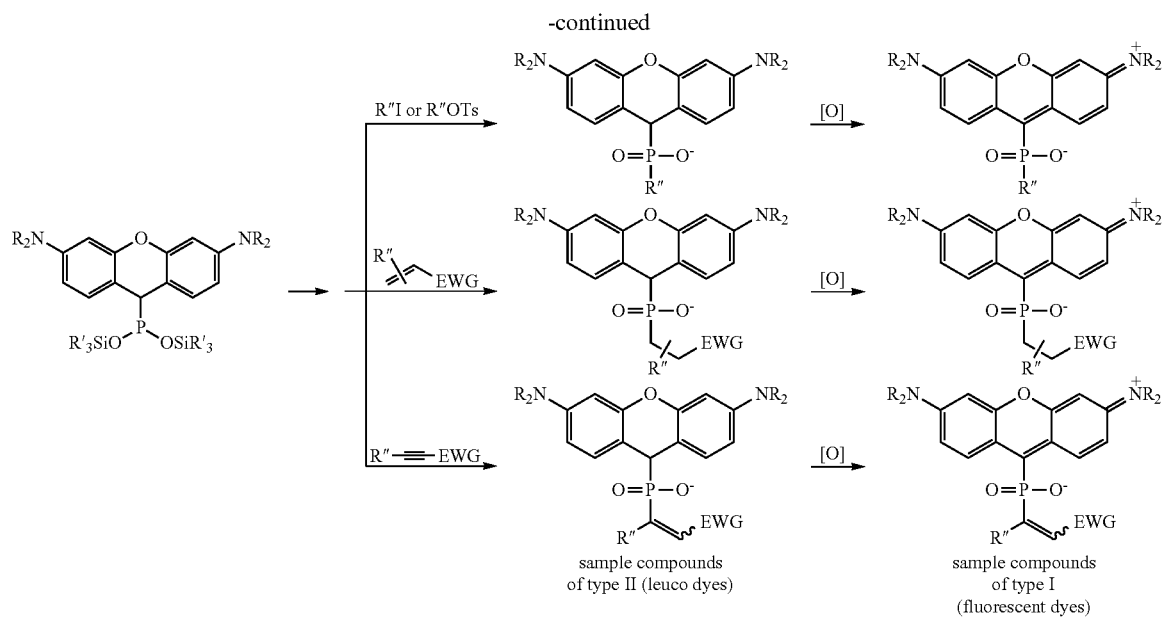

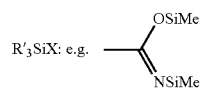

(R' = Me, X = N=C(OTMS)Me)

EWG = electron-withdrawing group (CN, CO$_2$R''', CONR'''$_2$ etc.)

In some embodiments, the compounds of type II can be prepared by nucleophilic addition of phosphite salts (for example, prepared in situ from dialkyl phosphites and NaH) to appropriately substituted acridinium salts or coumarins, as shown in Scheme 10. In some embodiments, the resulting leuco dyes II can be further oxidized to fluorescent dyes of type I in vivo or in vitro, for example by addition of a suitable oxidant (preferably DDQ).

Scheme 10

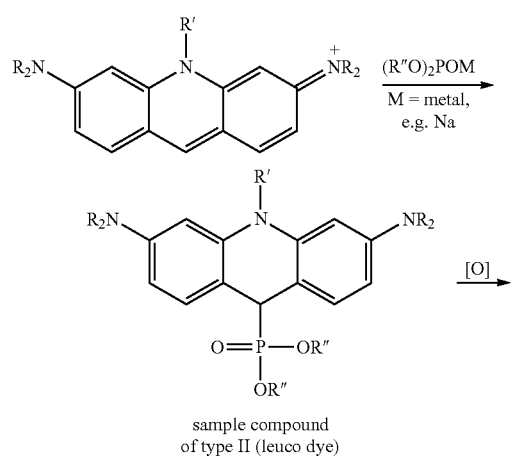

sample compound of type II (leuco dye)

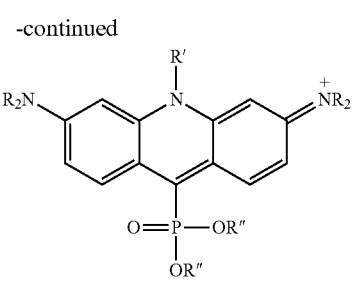

sample compound of type I (fluoroescent dye)

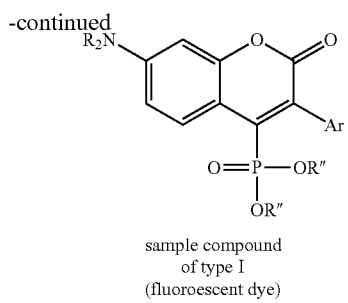

sample compound
of type I
(fluoroescent dye)

Those of ordinary skill will recognize that the methods and schemes described herein are provided for illustrative purposes only and are not intended to limit the scope of the reactions or reaction sequences useful for synthesizing embodiments of the presently-disclosed compounds.

The compounds described herein may contain one or more double bonds and may therefore potentially give rise to E/Z (cis-/trans-)isomers, as well as other conformational isomers. Unless stated to the contrary, the invention includes all such possible isomers, as well as mixtures of such isomers. Unless stated to the contrary, a formula with chemical bonds shown only as solid lines and not as wedges or dashed lines contemplates each possible isomer, e.g. each enantiomer and diastereoisomer, and a mixture of isomers, such as a racemic or scalemic mixture.

Also, the compounds described herein can contain one or more stereogenic centers or axes of chirality and can therefore potentially give rise to diastereoisomers and optical isomers. Unless stated to the contrary, the present invention includes all such possible diastereoisomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

The subject matter of the present invention also includes derivatives of and compositions with any of the compounds described herein.

For example, the compounds of the invention may be present in the form of a salt with organic or inorganic counterion(s), or as a cocrystal with another organic or inorganic compound(s).

The claimed subject matter in particular includes a conjugate or bioconjugate comprising a novel compound according to the present invention.

More specifically, such a conjugate or bioconjugate comprises a compound according to any one of claims 1-8 coupled via at least one covalent chemical bond or at least one molecular complex to a chemical entity or substance, such as amine, thiol, carboxylic acid, aldehyde, alcohol, aromatic compound, heterocycle, e.g. tetrazine, alkyne, alkene including strained and bicyclic alkenes, e. g. trans-cyclooctene, cyclopropene and norbornene derivatives, organic azide, dye, amino acid, amino acid residue coupled to any chemical entity, peptide, protein, in particular enzymes and immunoglobulins, antibody, single-domain antibody, carbohydrate including a carbohydrate residue attached to a protein, nucleic acid, toxin, lipid, virus, virus-like particle, biotin and its derivatives, a chemical tag, a recognition unit, etc.

Applications

As already mentioned above, the compounds and fluorescent dyes of the invention have a number of favorable characteristics which render the same especially suitable for various applications, in particular in the field of optic microscopy and imaging techniques.

Consequently, a further aspect of the present invention relates to the use of a novel compound as defined above or of a leuco derivative thereof or of a conjugate comprising the same as a fluorescent label, probe, tracer or marker, as well as quencher in fluorescence energy transfer (FRET) experiments, imaging and optical microscopy.

In a more specific embodiment, these compounds, derivatives or conjugates may be used for tracking and monitoring dynamic processes in a sample or in an object.

In another specific embodiment, these compounds, derivatives or conjugates may be used as fluorescent tags, analytical reagents and labels in optical microscopy, imaging techniques, protein tracking, nucleic acid labeling and flow cytometry.

In still more specific embodiments, the optical microscopy and imaging methods may comprise stimulated emission depletion microscopy [STED], single molecule switching techniques (SMS: diffraction unlimited optical resolution achieved by recording the fluorescence signals of single molecules, provided that they are reversibly or irreversibly switched between "dark" and "bright" states), such as single molecule localization microscopy [SMLM], photoactivation localization microscopy [PALM, PALMIRA, fPALM], stochastic optical reconstruction microscopy [STORM]), fluorescence correlation spectroscopy [FCS], fluorescence recovery after photobleaching [FRAP], fluorescence lifetime imaging [FLIM], ground state depletion with individual molecular return [GSD or GSDIM], and fluorescence resonant energy transfer [FRET].

The presently-disclosed subject matter further includes a method of using the compounds described herein. In some embodiments, the method comprises utilizing the compound as a reporter for enzyme activity, as a fluorescent tag, as a pH indicator, as a redox indicator, as a sensor for a target substance (an analyte), as an agent for imaging experiments, and/or as an imaging agent for super-resolution microscopy.

Some embodiments of the presently-disclosed subject matter include methods for detecting a target sample with a compound of the following formulae:

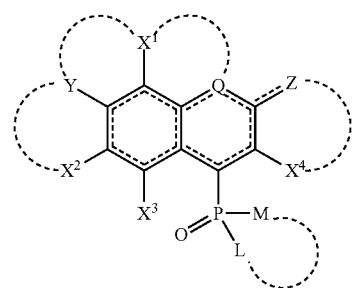

-continued

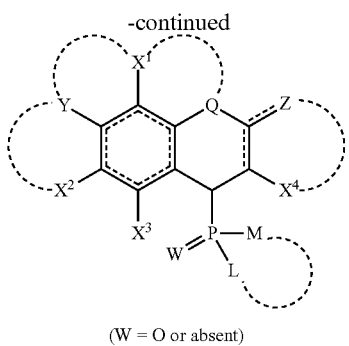

(W = O or absent)

wherein:

each $X^1$, $X^2$, $X^3$, $X^4$ is independently selected from H, halogen, CN, $NO_2$, $OR^1$, $SR^1$, $NR^1R^2$, $COR^1$, $COOR^1$, $CONR^1R^2$, $PO_3R^1R^2$, $SO_2R^1$, $SO_3R^1$ and $R^3$, wherein:

$R^1$ and $R^2$ can represent H, unsubstituted or substituted alkyl (cycloalkyl), unsubstituted or substituted aryl, unsubstituted or substituted heteroaryl, and wherein $R^1$ and $R^2$ can form together a substituted or unsubstituted 4-7 membered ring;

$R^3$ is alkyl, cycloalkyl, alkenyl, alkynyl, aryl or heteroaryl, optionally substituted with one or more heteroatoms independently selected from N, O, S, halogen, $N_3$, amine, OH, $OR^1$, $OCOR^1$, aryl, $COOR^1$, $NR^1COR^2$, $CONR^1R^2$, $PO_3R^1R^2$ and $SO_3R^1$, where $R^1$ and $R^2$ are defined as above;

Y is selected from $OR^1$ or $NR^1R^2$, where $R^1$ and $R^2$ are defined as above; in addition, either Y and $X^1$, or Y and $X^2$, or both of these pairs, taken together with the atoms to which they are bonded, can form substituted or unsubstituted 5-7 membered rings;

Q is selected from O, S, $SO_2$, NR, $C(R^3)_2$, $Si(R^3)_2$, $Ge(R^3)_2$, $P(=O)R^3$, where $R^3$ is defined as above, and wherein Q and $X^1$, taken together with the atoms to which they are bonded, can form a substituted or unsubstituted 5-7 membered ring;

L and M are independently selected from $OR^1$, $SR^1$, $NR^1R^2$ and $R^3$, where $R^1$, $R^2$ and $R^3$ are defined as above, and wherein L and M, taken together with the atoms to which they are bonded, can form a substituted or unsubstituted 5-7 membered ring;

Z is selected from O, S, $NR^1$, $CR^1_{(2)}$ (including a substituted aryl group), and wherein Z and $X^4$, taken together with the atoms to which they are bonded, can form a substituted or unsubstituted 5-7 membered ring.

The presently-disclosed method for detecting a target substance can further comprise a detecting step that includes detecting an emission light from the compound, the emission light indicating the presence of the target substance.

In some embodiments the method for using the compounds further comprises exciting the compound by exposing the compound to an absorption light that includes an absorption wavelength. As described herein, the absorption light can include an absorption wavelength from ultraviolet light to near infrared light. In specific embodiments the absorption wavelength can be in a range of 200 nm to about 1000 nm, or in a range of about 300 nm to about 800 nm.

In some embodiments the detecting step is performed by use of fluorescence spectroscopy or by the naked eye. In some embodiments the detecting step is performed with a microscope. In some embodiments the detecting step is performed with a fluorimeter or a microplate reader. In some embodiments the presence of a target substance can indicate the occurrence or absence of a particular biological function, as will be appreciated by those skilled in the art. In some embodiments the method is performed in a live cell, a tissue and/or a subject.

Some embodiments of detection methods comprise contacting the sample with two or more embodiments of compounds that are selective for different target substances. Methods for detecting two or more target substances with two or more of the presently-disclosed compounds are referred to herein as "multiplex" detection methods.

In some of the present multiplex methods, two or more distinct target substances and/or two or more regions of one target substance are detected using two or more probes, wherein each of the probes is labeled with a different embodiment of the present compounds. The presently-disclosed compounds can be used in multiplex detection methods for a variety of target substances, whereby the first compound can be selective for a first target substance, is absorbing at a first absorption wavelength and can be emitting a first emission light, and the second compound can be selective for a second target substance, is absorbing at a second absorption wavelength and can be emitting a second emission light. In some embodiments the emission wavelengths of the first and second compounds are different from one another, and in other embodiments the absorption wavelengths of the first and second compounds are different from one another, providing an efficient means for detecting a plurality of different target substances in one setting.

Figure 1:
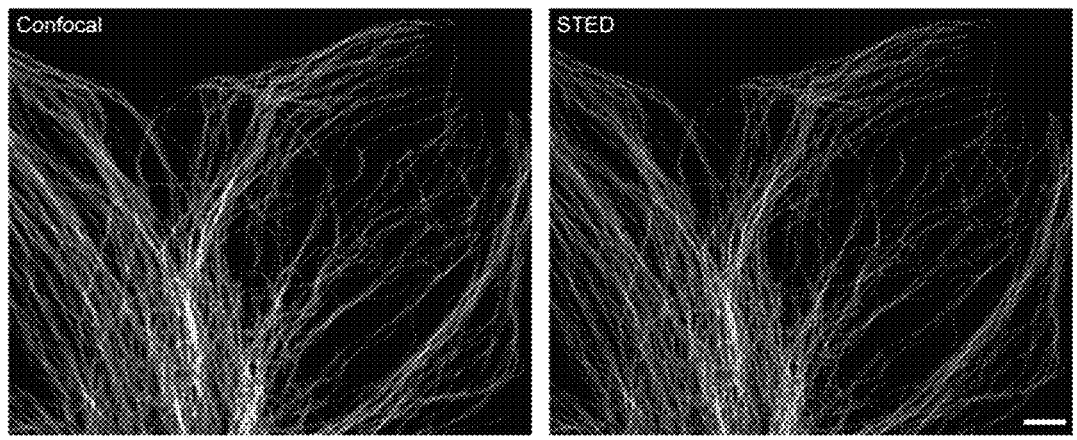
FIG. 1 shows confocal and STED images of tubulin filaments in a methanol-fixed Vero cell using a primary anti-tubulin antibody and a secondary antibody conjugated with the dye 23-NHS.

The present invention is further illustrated by the following specific but non-limiting examples.

EXAMPLE 1

Synthesis of Fluorescent Phosphorylated Coumarin Dyes and their Precursors

Dimethyl [3-(benzo[d]thiazol-2-yl)-7-(diethylamino)-2-oxo-2H-chromen-4-yl]phosphonate (1)

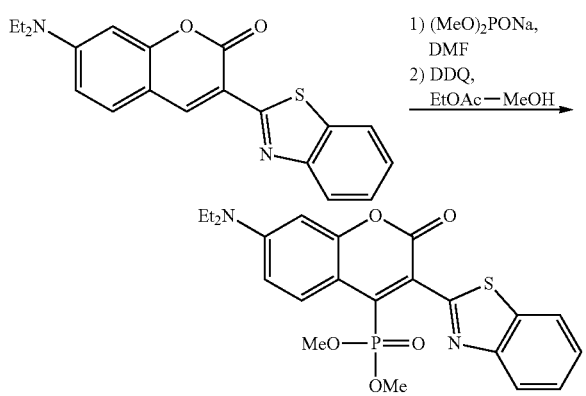

Compound 1. To a stirred suspension of NaH (17 mg of 60 wt. % in mineral oil, 0.429 mmol) in dry DMF (0.5 mL), cooled in ice-water bath, dimethyl phosphite (40 μL, 0.429 mmol) was added in one portion. The resulting suspension was warmed up to rt and stirred for 30 min, turning into a clear solution, which was added to a stirred suspension of Coumarin 6 (50 mg, 0.143 mmol) in DMF (0.5 mL). The orange solid dissolved immediately and clear red-orange solution formed. The mixture was stirred at rt for 1 h, and the resulting pale orange solution was poured into water (30 mL) and brine (10 mL), extracted with EtOAc (4×15 mL), the combined extracts were dried over $Na_2SO_4$, filtered and evaporated. The residue was taken up in EtOAc (20 mL) and MeOH (5 mL), heated up to 70° C., and a solution of DDQ (32 mg, 0.143 mmol) in EtOAc (2 mL) was added quickly dropwise. The mixture was stirred at 70° C. for 5 min, cooled down to rt and evaporated. The crude product was purified by column chromatography twice (16 g $SiO_2$, gradient 50% to 100% EtOAc/hexane, and 17 g $SiO_2$, gradient 50% to 80% EtOAc/hexane) and lyophilized from 1,4-dioxane. Bright yellow solid, yield 34 mg (52%). $^1H$ NMR (400 MHz, $CDCl_3$): δ 8.18 (d, J=9.3 Hz, 1H), 8.08 (ddd, J=8.1, 1.3, 0.7 Hz, 1H), 7.92 (ddd, J=8.0, 1.3, 0.7 Hz, 1H), 7.48 (ddd, J=8.2, 7.2, 1.3 Hz, 1H), 7.41 (ddd, J=8.3, 7.3, 1.2 Hz, 1H), 6.65 (dd, J=9.4, 2.7 Hz, 1H), 6.52 (dd, J=2.7, 1.7 Hz, 1H), 3.67 (s, 3H), 3.64 (s, 3H), 3.44 (q, J=7.1 Hz, 4H), 1.23 (t, J=7.1 Hz, 6H). $^{13}C$ NMR (101 MHz, $CDCl_3$): 5 162.2 (d, J=7.1 Hz), 160.0 (d, J=19.9 Hz), 156.6 (d, J=14.3 Hz), 152.8, 151.5, 142.3 (d, J=172.0 Hz), 137.1, 130.5 (d, J=2.7 Hz), 126.1, 125.6, 123.6, 121.7, 119.5 (d, J=6.4 Hz), 109.7, 107.2 (d, J=9.9 Hz), 97.4 (d, J=2.5 Hz), 67.2, 53.6, 53.5, 45.1, 12.6. $^{31}P$ NMR (162 MHz, $CDCl_3$): δ 13.37. MS (ESI): m/z (positive mode, rel. int., %)=459.1 (100) $[M+H]^+$, 497.1 (45) $[M+K]^+$. HRMS ($C_{22}H_{23}N_2O_5PS$): m/z (positive mode)=459.1138 (found $[M+H]^+$), 459.1138 (calc.). UV/Vis (MeCN): $λ_{max}$ (ε)=439 nm (24000 $M^{-1}cm^{-1}$); fluorescence (MeCN): $λ_{excit}$=470 nm, $λ_{em}$=651 nm, $Φ_{fl}$=0.20. Standard: Abberior Star520SX tert-butyl ester, $Φ_{fl}$=0.27 (MeCN).

3-(Benzo[d]thiazol-2-yl)-2-oxo-2H-chromen-7-yl trifluoromethanesulfonate (2a)

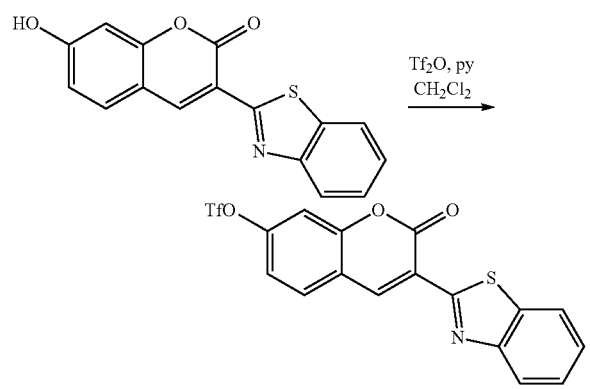

Compound 2a. Pyridine (0.55 mL, 6.8 mmol, 4 eq) was added to a suspension of 3-(2-benzothiazolyl)umbelliferone (500 mg, 1.69 mmol) in $CH_2Cl_2$ (25 mL); a voluminous yellow precipitate formed. The suspension was cooled in ice-water bath, and triflic anhydride (572 μL, 3.4 mmol, 2 eq) was added dropwise; the precipitate dissolved. The mixture was warmed up to rt and the resulting thin suspension was stirred at rt (room temperature) for 3 h. It was then cooled in ice-water bath, diluted with water (30 mL), re-extracted with $CH_2Cl_2$ (2×20 mL); the combined organic layers were washed with water and brine, dried over $Na_2SO_4$. The product was isolated by flash chromatography on Biotage Isolera system (12 g Sepacore Silica HP cartridge, gradient 20% to 100% $CH_2Cl_2$/hexane); the fractions containing the product were evaporated to lemon-yellow solid, which was triturated with hexane, filtered off, washed with hexane and dried in vacuo. Yield 630 mg (87%). $^1H$ NMR (400 MHz, $CDCl_3$): δ 9.03 (s, 1H), 8.11-8.05 (m, 1H), 8.00-7.94 (m, 1H), 7.80 (d, J=8.6 Hz, 1H), 7.54 (ddd, J=8.3, 7.1, 1.3 Hz, 1H), 7.43 (ddd, J=8.2, 7.1, 1.1 Hz, 1H), 7.39-7.35 (m, 1H), 7.31 (dd, J=8.6, 2.4 Hz, 1H). $^{19}F$ NMR (376 MHz, $CDCl_3$): δ −72.51. $^{13}C$ NMR (101 MHz, $CDCl_3$): δ 158.9, 158.8, 154.2, 152.6, 151.6, 139.7, 137.1, 131.0, 126.9, 125.9, 123.3, 121.9, 121.5, 119.0, 118.8 (q, J=321.0 Hz), 118.7, 110.6. MS (ESI): m/z (positive mode, rel. int., %)=428.2 (100) $[M+H]^+$. HRMS ($C_{17}H_8NO_5S_2F_3$): m/z (positive mode)=427.9867 (found $[M+H]^+$), 427.9869 (calc.).

3-(Benzo[d]thiazol-2-yl)-7-[3-(tert-butyldimethylsilyloxy)azetidin-1-yl]-2H-chromen-2-one (2b)

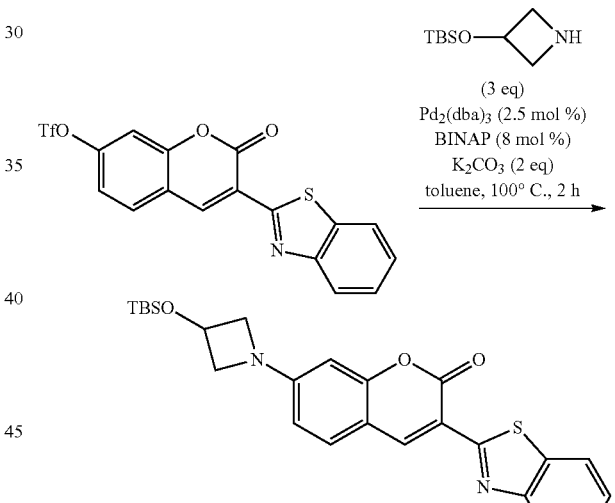

Compound 2b. A mixture of 2a (150 mg, 0.35 mmol), 3-(tert-butyldimethylsilyloxy)azetidine [prepared according to WO 2010015849 A2] (196 mg, 1.05 mmol, 3 eq), $Pd_2(dba)_3$ (8 mg, 8.75 μmol, 2.5 mol %), (±)-BINAP (18 mg, 28 μmol, 8 mol %) and potassium carbonate (97 mg, 0.7 mmol, 2 eq) in toluene (2 mL) was sealed in a 10 mL vial capped with a septum, degassed on a Schlenk line and stirred under argon at 100° C. (bath temperature) for 2 h. Yellow solution gradually turned into an orange suspension. Upon cooling down to rt, acetic acid (1 mL) was added to the reaction mixture, the mixture was diluted with $CH_2Cl_2$ (30 mL) and evaporated on Celite. The product was isolated by flash chromatography on Biotage Isolera system (12 g Sepacore Silica HP cartridge, gradient 50% to 100% $CH_2Cl_2$/hexane); the fractions containing the product were evaporated to bright orange solid, yield 98 mg (60%). $^1H$ NMR (400 MHz, $CD_3CN$+1% TFA): δ 8.16 (ddd, J=8.2, 1.2, 0.7 Hz, 1H), 8.09 (dt, J=8.3, 0.9 Hz, 1H), 7.78 (ddd, J=8.4, 7.3, 1.2 Hz, 1H), 7.72-7.62 (m, 2H), 7.67 (s, 1H), 6.58 (dd, J=8.9, 2.1 Hz, 1H), 6.36 (dd, J=2.1, 0.7 Hz, 1H), 4.89 (tt, J=6.5, 4.2 Hz, 1H), 4.51-4.44 (m, 2H), 4.06-3.99 (m, 2H), 0.95 (s, 9H), 0.14 (s, 6H). $^{13}$C NMR (101 MHz, nitrobenzene-d$_5$): δ 162.1, 161.1, 157.2, 154.7, 153.6, 142.9, 137.2, 131.6, 126.8, 125.3, 123.2, 122.3, 113.3, 110.0, 109.9, 96.5, 62.8, 61.7, 26.0, 18.4, −4.9. MS (ESI): m/z (positive mode, rel. int., %)=465.3 (100) [M+H]$^+$. HRMS (C$_{25}$H$_{28}$N$_2$O$_3$SSi): m/z (positive mode) =465.1653 (found [M+H]$^+$), 465.1663 (calc.).

Dimethyl [3-(benzo[d]thiazol-2-yl)-7-(3-hydroxyazetidin-1-yl)-2-oxo-2H-chromen-4-yl]phosphonate (2)

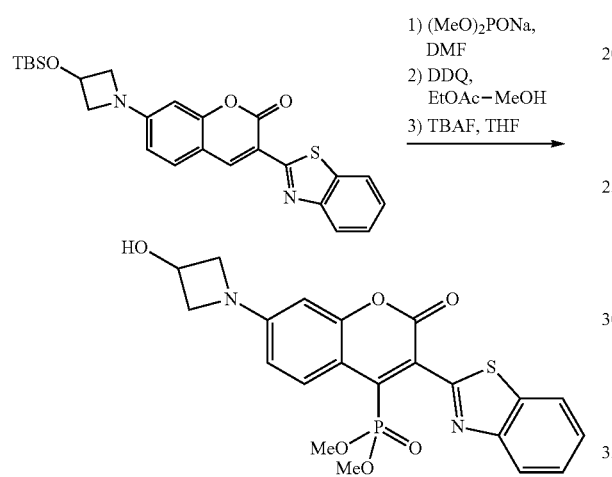

Compound 2. To a stirred suspension of NaH (23 mg of 60 wt. % in mineral oil, 0.58 mmol, 3 eq) in dry DMF (0.5 mL), cooled in ice-water bath, dimethyl phosphite (53 µL, 0.58 mmol, 3 eq) was added in one portion. The resulting suspension was warmed up to rt and stirred for 30 min, turning into a clear solution, which was added to a stirred suspension of 2b (90 mg, 0.194 mmol) in DMF (3 mL). The orange solid quickly dissolved and clear reddish-brown solution formed. The mixture was stirred at rt for 1 h, DMF was evaporated in vacuo at rt, and the residue was mixed with water (20 mL) and brine (20 mL). Acetic acid was added to pH 3, and the mixture was extracted with EtOAc (3×20 mL), the combined extracts were dried over Na$_2$SO$_4$, filtered and evaporated. The residue was taken up in EtOAc (20 mL) and MeOH (5 mL), heated up to 70° C., and a solution of DDQ (44 mg, 0.194 mmol, 1 eq) in EtOAc (3 mL) was added quickly dropwise. The resulting red-orange mixture was stirred at 70° C. for 5 min, cooled down to rt and evaporated on Celite. The product was isolated by flash chromatography on Biotage Isolera system (10 g Biotage SNAP Ultra cartridge, gradient 0% to 10% methanol/CH$_2$Cl$_2$); two fractions were collected, containing the product and the TBS-protected product. Both fractions were pooled together, evaporated and the mixture was used for deprotection. The material was dissolved in THF (7 mL), cooled in ice-water bath, and tetrabutylammonium fluoride trihydrate (92 mg, 0.291 mmol) was added. The resulting brown-yellow solution was allowed to warm up to rt and stirred for 1 h. The mixture was diluted with brine (15 mL), extracted with EtOAc (3×20 mL), the combined extracts were dried over Na$_2$SO$_4$, filtered and evaporated on Celite. The product was isolated by flash chromatography on Biotage Isolera system (12 g Sepacore Silica HP cartridge, gradient 0% to 50% methanol/ethyl acetate); the fractions containing the product were evaporated to brown-red solid, which was freeze-dried from aqueous dioxane to fluffy red solid, yield 20 mg (23% over 3 steps). $^1$H NMR (400 MHz, acetic acid-d$_4$): δ 11.57 (s, 1H), 8.16 (ddd, J=8.2, 1.2, 0.7 Hz, 1H), 8.10 (d, J=9.1 Hz, 1H), 8.03 (ddd, J=8.0, 1.3, 0.7 Hz, 1H), 7.57 (ddd, J=8.3, 7.2, 1.3 Hz, 1H), 7.50 (ddd, J=8.3, 7.2, 1.2 Hz, 1H), 6.48 (dd, J=9.1, 2.4 Hz, 1H), 6.33 (dd, J=2.4, 1.6 Hz, 1H), 4.86 (tt, J=6.6, 4.3 Hz, 1H), 4.34 (ddd, J=9.2, 6.6, 1.3 Hz, 2H), 3.97 (ddd, J=9.2, 4.4, 1.3 Hz, 2H), 3.72 (s, 3H), 3.69 (s, 3H). MS (ESI): m/z (positive mode, rel. int., %)=459.2 (100) [M+H]$^+$. HRMS (C$_{21}$H$_{19}$N$_2$O$_6$PS): m/z (positive mode)=459.0764 (found [M+H]$^+$), 459.0774 (calc.). UV/Vis (MeCN): λ$_{max}$ (ε)=424 nm (19000 M$^{-1}$ cm$^{-1}$); fluorescence (MeCN): λ$_{excit}$=470 nm, λ$_{em}$=651 nm, Φ$_{fl}$=0.16. Standard: Abberior Star520SX tert-butyl ester, Φ$_{fl}$=0.27 (MeCN).

Di-tert-butyl [3-(benzo[d]thiazol-2-yl)-7-(diethylamino)-2-oxo-2H-chromen-4-yl]phosphonate (3)

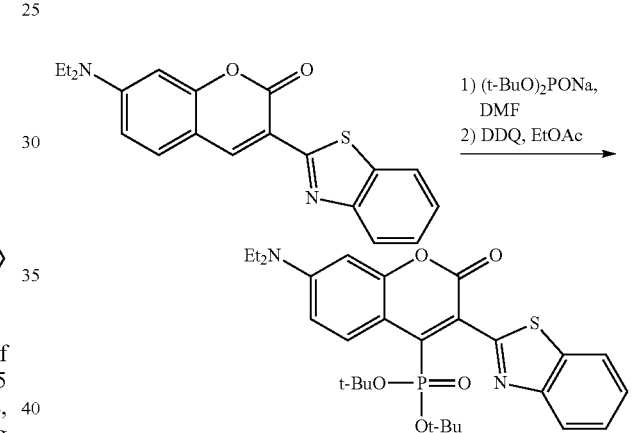

Compound 3. To a stirred suspension of NaH (34 mg of 60 wt. % in mineral oil, 0.858 mmol) in dry DMF (1.5 mL), cooled in ice-water bath, di(tert-butyl) phosphite (173 µL, 0.858 mmol) was added in one portion. The resulting suspension was stirred for 2 h at rt and for 30 min at 55° C. The resulting thin white suspension was added to a stirred suspension of Coumarin 6 (100 mg, 0.286 mmol) in DMF (0.8 mL). The solids dissolved immediately and clear light-orange solution formed. The mixture was stirred at rt for 1 h and then poured into sat. aq. NaHCO$_3$ (50 mL), extracted with EtOAc (4×15 mL), the combined extracts were dried over Na$_2$SO$_4$, filtered and evaporated. The residue was redissolved in EtOAc (20 mL), heated up to 75° C., and a solution of DDQ (65 mg, 0.286 mmol) in EtOAc (3 mL) was added quickly dropwise. The mixture was stirred at 75° C. for 5 min, cooled down to rt and evaporated. The product was isolated by column chromatography (30 g SiO$_2$, gradient 20% to 50% EtOAc/hexane) and lyophilized from 1,4-dioxane. Bright yellow-orange solid, yield 130 mg (84%). $^1$H NMR (400 MHz, acetone-d$_6$): δ 8.25 (br.s, 1H), 8.08-8.03 (m, 1H), 7.99 (ddd, J=8.1, 1.2, 0.6 Hz, 1H), 7.55-7.47 (m, 1H), 7.47-7.41 (m, 1H), 6.84 (dd, J=9.4, 2.7 Hz, 1H), 6.58 (dd, J=2.7, 1.5 Hz, 1H), 3.57 (q, J=7.2 Hz, 4H), 1.45 (s, 18H), 1.26 (t, J=7.1 Hz, 6H). $^{31}$P NMR (162 MHz, acetone-d$_6$): 5 0.60. $^{13}$C NMR (101 MHz, acetone-d$_6$): δ 209.9, 163.7

(d, J=7.0 Hz), 160.4, 157.5 (d, J=13.4 Hz), 154.1, 152.1, 138.2, 132.1 (d, J=2.0 Hz), 126.3, 125.7, 123.9, 122.3, 110.9, 109.8, 107.2 (d, J=7.9 Hz), 97.6 (d, J=2.6 Hz), 85.2 (d, J=7.3 Hz), 67.6, 45.2, 12.8. MS (ESI): m/z (positive mode, rel. int., %)=543.2 (55) [M+H]$^+$, 565.2 (35) [M+Na]$^+$, 581.2 (100) [M+K]$^+$. HRMS ($C_{28}H_{36}N_2O_5PS$): m/z (positive mode)=543.2077 (found [M+H]$^+$), 543.2077 (calc.). UV/Vis (MeCN): $\lambda_{max}$ (ε)=434 nm (39000 M$^{-1}$cm$^{-1}$); fluorescence (MeCN): $\lambda_{excit}$=470 nm, $\lambda_{em}$=658 nm, $\Phi_{fl}$=0.29. Standard: Abberior Star520SX tert-butyl ester, $\Phi_{fl}$=0.27 (MeCN).

[3-(Benzo[d]thiazol-2-yl)-7-(diethylamino)-2-oxo-2H-chromen-4-yl]phosphonic acid (4)

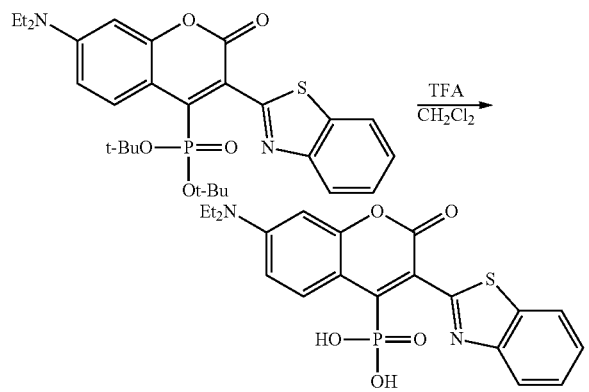

Compound 4. Trifluoroacetic acid (150 μL) was added to a stirred solution of the dye 3 (82 mg, 0.15 mmol) in CH$_2$Cl$_2$ (5 mL). The orange color of the solution turned violet upon addition of the acid and eventually deep purple. The mixture was stirred at rt for 30 min, evaporated to dryness, the residue was dissolved in acetic acid and lyophilized. Yield 64 mg (99%), red-brown solid. $^1$H NMR (400 MHz, acetic acid-d$_4$): δ 9.06 (d, J=9.6 Hz, 1H), 8.14 (t, J=7.3 Hz, 2H), 7.76 (t, J=7.6 Hz, 1H), 7.66 (t, J=7.7 Hz, 1H), 6.91 (d, J=9.2 Hz, 1H), 6.61 (s, 1H), 3.61 (q, J=7.1 Hz, 4H), 1.30 (t, J=7.0 Hz, 6H). $^{31}$P NMR (162 MHz, acetic acid-d$_4$): δ 5.41. MS (ESI): m/z (negative mode, rel. int., %)=429.1 (100) [M−H]$^-$. HRMS ($C_{20}H_{19}N_2O_5PS$): m/z (negative mode)= 429.0684 (found [M−H]$^-$), 429.0680 (calc.). UV/Vis (PBS 7.4): $\lambda_{max}$ (ε)=419 nm (22000 M$^{-1}$cm$^{-1}$); fluorescence (MeCN): $\lambda_{excit}$=460 nm, $\lambda_{em}$=613 nm, $\Phi_{fl}$=0.04. Standard: Abberior Star520SX tert-butyl ester, $\Phi_{fl}$=0.27 (MeCN).

EXAMPLE 2

Synthesis of Fluorescent Phosphorylated Xanthene Dyes and their Precursors 9-(Dimethoxyphosphoryl)-3,6-bis(dimethylamino)-9H-xanthenylium trifluoroacetate (5)

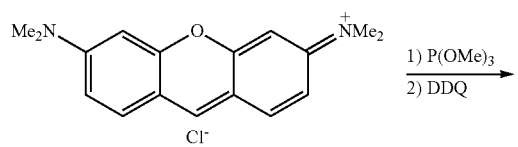

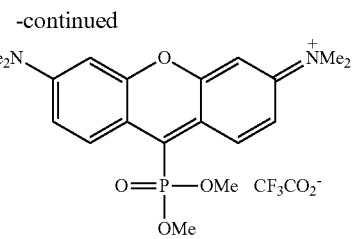

Compound 5. In a screw-cap test tube to a suspension of Pyronin Y (50 mg; 0.165 mmol) in CH$_2$Cl$_2$ (1 mL) P(OMe)$_3$ (20 mg; 0.165 mmol) was added at r.t. under argon. The resulting reaction mixture was warmed up to 40° C. and stirred for 2 h at this temperature. After cooling down to 0° C., DDQ (112 mg; 0.495 mmol) was added. The reaction mixture was stirred additionally for 15 min at 0° C. After dilution with MeCN (~3 mL), the reaction mixture was directly subjected to column chromatography on SiO$_2$ (30 g; MeCN→MeCN/H$_2$O 10:1+0.1 v/v % of TFA) to afford 20 mg (29%) of a dark violet powder. $^1$H NMR (400 MHz, CD$_3$CN): δ=3.30 (s, 12H, 2×NMe$_2$), 3.85 (d, $J_{H-P}$=11.6 Hz, 6H, 2×OMe), 6.74 (m, $J_{H-H}$=2.5 Hz, 2H$_{ar}$), 7.13 (dd, $J_{H-H}$=9.9 and 2.5 Hz, 2H$_{ar}$), 8.69 (d, $J_{H-H}$=9.9 Hz, 2H$_{ar}$) ppm. $^{13}$C NMR (100 MHz, CD$_3$CN, APT): δ=40.4 (+), 53.3 (+, d, $J_{C-P}$=5 Hz), 96.4 (+), 110.0 (−), 115.0 (+), 115.8 (−, d, $J_{C-P}$=10.4 Hz), 132.0 (+, d, $J_{C-P}$=3.3 Hz), 157.0 (−), 157.2 (−, d, $J_{C-P}$=13.3 Hz) ppm. $^{31}$P NMR (162 MHz, CD$_3$CN): (δ=13.7 ppm. MS (ESI): m/z (positive mode, rel. int., %)=375.2 (100) [M−Cl]$^+$. HPLC: t$_R$=8.5 min (96.5%), B/A=30/70-100/0 in 25 min, column 4×250 mm, 1.2 mL/min, detection at 254 nm.

9-(Diisopropoxyphosphoryl)-3,6-bis(dimethylamino)-9H-xanthenylium trifluoroacetate (6)

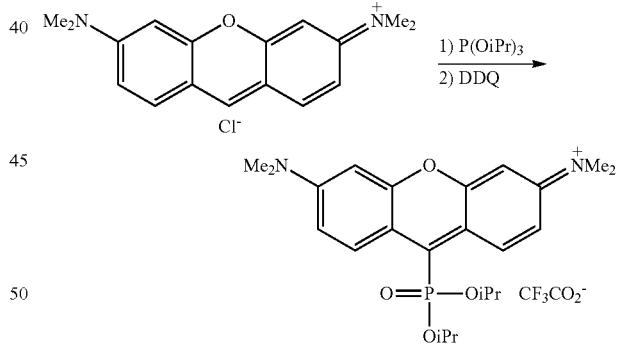

Compound 6. In a screw-cap test tube to a suspension of Pyronin Y (50 mg; 0.165 mmol) in MeCN (1 mL) P(OiPr)$_3$ (34 mg; 0.165 mmol) was added at r.t. under argon. The resulting reaction mixture was warmed up to 60° C. and stirred for 1 h at this temperature. After cooling down to 0° C., DDQ (37 mg; 0.165 mmol) was added, and the reaction mixture was stirred for additional 10 min at 0° C. After warming up to r.t., the reaction mixture was directly subjected to column chromatography on SiO$_2$ (30 g; MeCN-→MeCN/H$_2$O 10:1+0.1 v/v % of TFA) to afford 23 mg (30%) of a dark violet powder. $^1$H NMR (400 MHz, CD$_3$CN): δ=1.17 (d, $J_{H-H}$=6.2 Hz, 6H, OiPr), 1.43 (d, $J_{H-H}$=6.2 Hz, 6H, OiPr), 3.30 (s, 12H, 2×NMe$_2$), 4.85 (m, $J_{H-P}$=12.3 Hz, $J_{H-H}$=6.2 Hz, 2H, 2×OiPr), 6.78 (m, $J_{H-H}$=2.4 Hz, 2H$_{ar}$), 7.16 (dd, $J_{H-H}$=9.9, 2.6 Hz, 2H$_{ar}$), 8.81 (d, $J_{H-H}$=9.9 Hz, 2H$_{ar}$) ppm. $^{13}$C NMR (100 MHz, CD$_3$CN, APT): δ=22.9 (+, d, $J_{C-P}$=5.0 Hz), 23.2 (+, d, $J_{C-P}$=4.0 Hz), 40.4(+), 73.6 (+, d, $J_{C-P}$=5.7 Hz), 96.3 (+, $J_{C-P}$=1.6 Hz), 110.0 (−), 114.8 (+), 115.4 (−, d, $J_{C-P}$=10.5 Hz), 132.4 (+, $J_{C-P}$=3.3 Hz), 157.0 (−), 157.3 (−, $J_{C-P}$=13.0 Hz) ppm. $^{31}$P NMR (162 MHz, CD$_3$CN): δ=8.1 ppm. MS (ESI): m/z (positive mode, rel. int., %)=431.3 (100) [M−Cl]$^+$. HPLC: $t_R$=13.5 min (97%), B/A=30/70-100/0 in 25 min, column 4×250 mm, 1.2 mL/min, detection at 254 nm. UV/Vis (MeCN): $\lambda_{max}$ (ε)=617 nm (57638 M$^{-1}$cm$^{-1}$); fluorescence (MeCN): $\lambda_{excit}$=585 nm, $\lambda_{em}$=649 nm, $\Phi_{fl}$=0.38. Standard: Oxazine 4, $\Phi_{fl}$=0.63 (MeOH). UV/Vis (PBS 7.4): $\lambda_{max}$ (ε)=629 nm (52254 M$^{-1}$cm$^{-1}$); fluorescence (PBS 7.4): $\lambda_{excit}$=585 nm, $\lambda_{em}$=668 nm, $\Phi_{fl}$=0.12. Standard: Oxazine 4, $\Phi_{fl}$=0.63 (MeOH).

9-[(Diisopropylamino)(methoxy)phosphoryl]-3,6-bis(dimethylamino)-9H-xanthenylium trifluoroacetate (7)

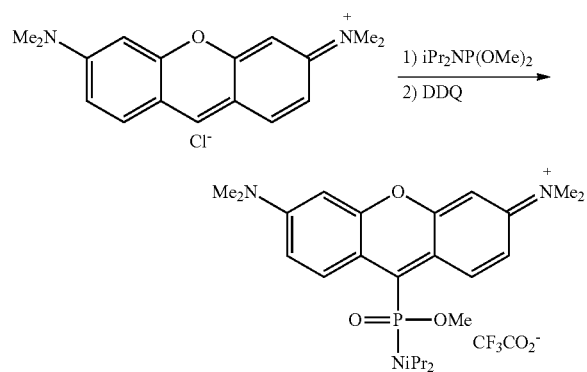

Compound 7. In a screw-cap test tube to a suspension of Pyronin Y (50 mg; 0.165 mmol) in MeCN (1 mL) dimethyl N,N-diisopropylphosphoramidite (32 mg; 0.165 mmol) was added at r.t. under Ar. The reaction mixture was warmed up to 60° C. and stirred for 30 min at this temperature. After cooling down to 0° C., DDQ (37 mg; 0.165 mmol) was added, and the reaction mixture was stirred for additional 10 min at 0° C. After warming up to r.t., the reaction mixture was directly subjected to column chromatography on SiO$_2$ (30 g; MeCN→MeCN/H$_2$O 20:1+0.1 v/v % of TFA). Fractions containing the title compound were evaporated to dryness, dissolved in water and extracted with CH$_2$Cl$_2$ (3×). The combined extracts were dried with Na$_2$SO$_4$ and evaporated to yield 32 mg (40%) of a dark violet solid. $^1$H NMR (400 MHz, CD$_3$CN): δ=1.23 (d, $J_{H-H}$=6.8 Hz, 6H, NiPr$_2$), 1.26 (d, $J_{H-H}$=6.8 Hz, 6H, NiPr$_2$), 3.29 (s, 12H, 2×NMe$_2$), 3.44-3.60 (m, 2H, NiPr$_2$), 3.72 (d, $J_{H-P}$=11.5 Hz, 3H, OMe), 6.74-6.77 (m, 2H$_{ar}$), 7.15 (dd, $J_{H-H}$=9.9 and 2.7 Hz, 2H$_{ar}$), 8.89 (d, $J_{H-H}$=9.9 Hz, 2H$_{ar}$) ppm. $^{13}$C NMR (100 MHz, CD$_3$CN, APT): δ=18.1 (+), 21.8 (+, d, $J_{C-P}$=2.7 Hz), 21.9 (+, d, $J_{C-P}$=2.7 Hz), 47.0 (+, m), 52.0 (+, d, $J_{C-P}$=5.8 Hz), 96.2 (+), 114.7 (+), 116.0 (−, d, $J_{C-P}$=9.2 Hz), 132.2 (+, d, $J_{C-P}$=3.3 Hz), 156.9 (−), 157.4 (−, d, $J_{C-P}$=11.7 Hz) ppm. $^{31}$P NMR (162 MHz, CD$_3$CN): δ=20.1 ppm. MS (ESI): m/z (positive mode, rel. int., %)=444.4 (100) [M−Cl]$^+$. HPLC: $t_R$=13.1 min (91%), B/A=30/70-100/0 in 25 min, column 4×250 mm, 1.2 mL/min, detection at 254 nm. UV/Vis (MeCN): $\lambda_{max}$ (ε)=616 nm (52455 M$^{-1}$cm$^{-1}$); fluorescence (MeCN): $\lambda_{excit}$=590 nm, $\lambda_{em}$=649 nm, $\Phi_{fl}$=0.39. Standard: Oxazine 4, $\Phi_{fl}$=0.63 (MeOH). UV/Vis (PBS 7.4): $\lambda_{max}$ (ε)=628 nm (46051 M$^{-1}$cm$^{-1}$); fluorescence (PBS 7.4): $\lambda_{excit}$=590 nm, $\lambda_{em}$=664 nm, $\Phi_{fl}$=0.11. Standard: Oxazine 4, $\Phi_{fl}$=0.63 (MeOH).

3,6-Bis(dimethylamino)-9-(diphenylphosphoryl)-9H-xanthenylium trifluoroacetate (8)

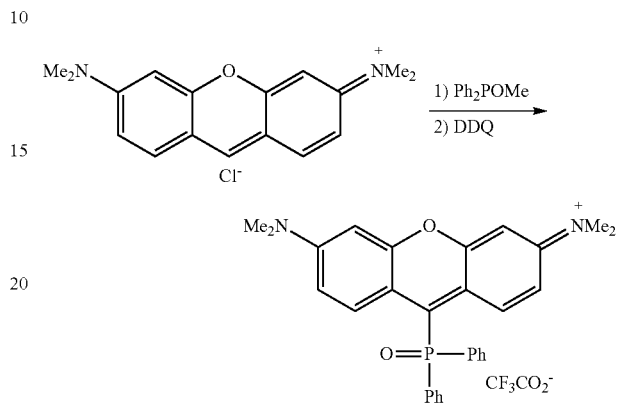

Compound 8. In a screw-cap test tube to a solution of Pyronin Y (50 mg; 0.165 mmol) in acetonitrile (5 mL) methoxydiphenylphosphine (56 mg; 0.330 mmol) was added at r.t. under argon. The resulting reaction mixture was warmed up to 60° C. and stirred for 1 h at this temperature. After cooling down to 0° C., DDQ (75 mg; 0.330 mmol) was added. The reaction mixture was stirred additionally for 30 min at 0° C. and directly subjected to column chromatography on SiO$_2$ (30 g; MeCN→5% to 50% H$_2$O/MeCN+0.1 v/v % of TFA) to afford 18 mg (22%) of the product as violet solid. HPLC: $t_R$=10.7 min (86%), B/A=30/70-100/0 in 25 min, column 4×250 mm, 1.2 mL/min, detection at 254 nm.

2-[[3,6-Bis(dimethylamino)-9H-xanthen-9-yl](dimethylamino)phosphoryloxy]benzoic acid (9a)

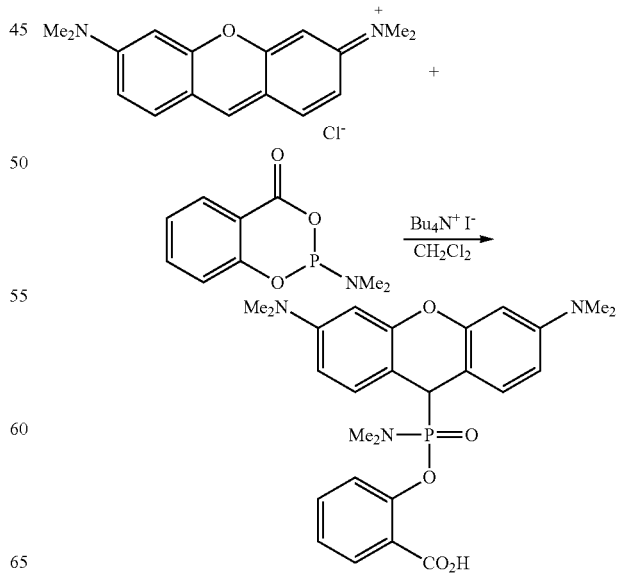

Compound 9a. A suspension of Pyronin Y (151 mg; 0.5 mmol) and tetrabutylammonium iodide (185 mg; 0.5 mmol) in $CH_2Cl_2$ was sonicated briefly, and 2-dimethylamino-4H-1,3,2-benzodioxaphosphorin-4-one [prepared according to Gast, R.; Kaukorat, T.; Neda, I.; Schmutzler, R. *Z. Naturforsch.* 1993, 48b, 867-874] (211 mg, 1 mmol) was added. The resulting mixture was sonicated for 2 min and stirred vigorously for 1 h, during which time a bright pink solution turned into a deep purple thin suspension. Sodium hydroxide (1 mL of 10% in MeOH/$H_2O$ 1:1) was added followed by just enough MeOH to homogenize the mixture. After stirring for 10 min, AcOH (2 mL) was added, and the mixture was evaporated to dryness (re-evaporated several times with acetone). The residue was subjected to column chromatography (45 g of $SiO_2$, gradient 10% to 40% MeOH/$CH_2Cl_2$). Fractions containing the product were pooled, evaporated to dryness, redissolved in 1,4-dioxane (20 mL), filtered through a 0.45 μm PTFE membrane filter and freeze-dried, yielding the intermediate xanthene 9a (106 mg, 43% yield) as a fluffy violet solid. MS (ESI): m/z (negative mode, rel. int., %)=494.3 (100) [M−H]$^+$. HRMS ($C_{27}H_{30}N_3O_5P$): m/z (negative mode)=494.1850 (found [M−H]$^−$), 494.1850 (calc.).

2-[[3,6-Bis(dimethylamino)-9H-xanthenylium-9yl] (dimethylamino)phosphoryloxy]-benzoate (9)

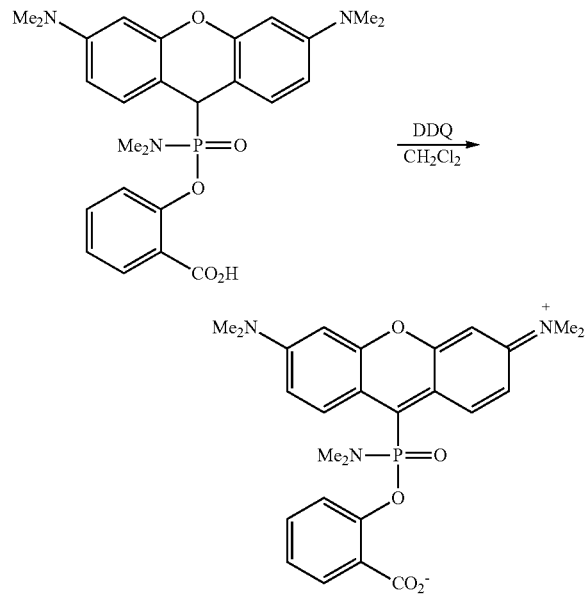

Compound 9. The compound 9a (52 mg; 0.105 mmol) was dissolved in $CH_2Cl_2$ (5 mL), the solution was cooled in dry ice-acetone bath, and DDQ (24 mg; 0.105 mmol) in $CH_2Cl_2$ (3 mL) was added quickly dropwise. The resulting dark violet solution was allowed to warm up to rt and evaporated to dryness. The residue was subjected to column chromatography (30 g of $SiO_2$, gradient 5% to 50% MeOH/$CH_2Cl_2$); the fractions containing the product were evaporated and re-purified by reversed-phase chromatography (15 g of RP—$C_{18}$, gradient 10% to 30% $H_2O$/MeCN). The pure fractions were evaporated to yield the product as a bronze solid (40 mg, 77%). $^1$H NMR (400 MHz, $CD_3OD$): δ 9.14 (d, J=9.8 Hz, 2H), 7.43 (d, J=8.4 Hz, 1H), 7.32 (ddd, J=8.5, 6.4, 2.8 Hz, 1H), 7.14-7.04 (m, 4H), 6.72-6.68 (m, 2H), 3.28 (s, 12H), 2.75 (s, 3H), 2.64 (s, 3H) ppm. $^{13}$C NMR (126 MHz, $CD_3OD$): δ 170.3, 158.6 (d, J=11.7 Hz), 158.1, 153.8 (d, J=155.5 Hz), 149.2 (d, J=7.4 Hz), 135.3 (d, J=2.9 Hz), 131.3, 129.6 (d, J=6.2 Hz), 128.8, 124.8, 122.3 (d, J=3.0 Hz), 116.8, 116.7 (d, J=9.4 Hz), 97.2 (d, J=1.4 Hz), 40.9, 39.0, 34.9. $^{31}$P NMR (162 MHz, $CD_3OD$): δ −1.56 ppm. MS (ESI): m/z (positive mode, rel. int., %)=494.2 (100) [M+H]$^+$, 516.2 (91) [M+Na]$^+$. HRMS ($C_{26}H_{28}N_3O_5P$): m/z (positive mode)=494.1841 (found [M+H]$^+$), 494.1839 (calc.). UV/Vis (MeOH): $\lambda_{max}$ (ε)=589 nm (49000 M$^{-1}$cm$^{-1}$); fluorescence (MeOH): $\lambda_{excit}$=540 nm, $\lambda_{em}$=622 nm, $\Phi_{fl}$=0.36. Standard: Atto 594, $\Phi_{fl}$=0.85 ($H_2O$). UV/Vis (PBS 7.4): $\lambda_{max}$ (ε)=603 nm (69000 M$^{-1}$cm$^{-1}$); fluorescence (PBS 7.4): $\lambda_{excit}$=540 nm, $\lambda_{em}$=638 nm, $\Phi_{fl}$=0.09. Standard: Atto 594, $\Phi_{fl}$=0.85 ($H_2O$).

tert-Butyl 3-[(diethoxyphosphino)(methyl)amino] propanoate (10a)

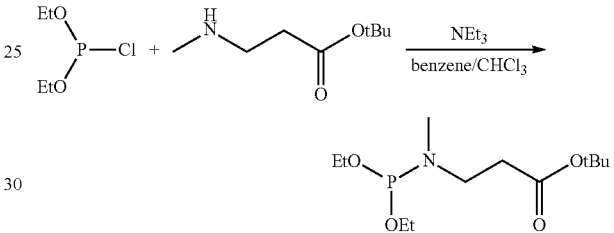

Compound 10a. To a solution of tert-butyl 3-(methylamino)propionate [prepared according to WO2009/083614 A1] (500 mg; 3.14 mmol) and $NEt_3$ (380 mg; 3.77 mmol) in a mixture of benzene and $CHCl_3$ (20 mL; 3:1), a solution of diethyl chlorophosphite (490 mg; 3.14 mmol) in benzene (2 mL) was added dropwise at 0° C. The reaction mixture was refluxed for 2 h. After cooling down to r.t., the reaction mixture was diluted with n-hexane (~20 mL) and filtered through a glass filter. The filtrate was evaporated and subjected to column chromatography (30 g of $SiO_2$, Hex/EtOAc 1:3+0.1 v/v % of $NEt_3$) to afford 392 mg (50%) of a colorless oil. $^1$H NMR (400 MHz, $CD_3CN$): δ=1.18 (t, $J_{H-H}$=7.0 Hz, 6H, 2×OEt), 1.43 (s, 9H, tBu), 2.37 (t, $J_{H-H}$=7.0 Hz, 2H, $CH_2$), 2.52 (d, $J_{H-P}$=6.6 Hz, 3H, NMe), 3.21 (dt, $J_{H-P}$=9.7 Hz, $J_{H-H}$=7.0 Hz, 2H, $NCH_2$), 3.57-3.72 (m, 4H, 2×OEt) ppm. $^{31}$P NMR (162 MHz, $CD_3CN$): δ=144.9 ppm.

tert-Butyl 3-[[[3,6-bis(dimethylamino)-9H-xanthen-9-yl](ethoxy)phosphoryl](methyl)-amino]propanoate (10b)

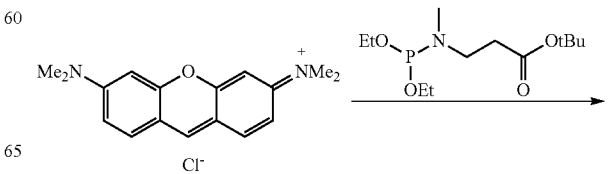

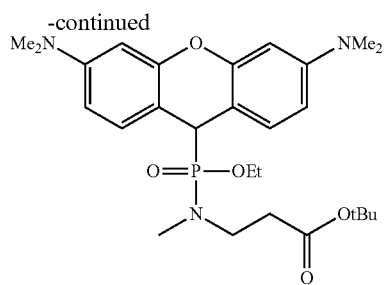

Compound 10b. In a screw-cap test tube to a suspension of Pyronin Y (50 mg; 0.165 mmol) in MeCN (1 mL) compound 10a (62 mg; 0.247 mmol) was added at r.t. under argon. The resulted mixture was stirred for 2 h at 60° C. After cooling down to r.t., the reaction mixture was diluted with CH$_2$Cl$_2$ (~3 mL) and subjected to column chromatography (30 g of SiO$_2$, CH$_2$Cl$_2$/MeOH 30:1) to yield 37 mg (43%) of a brown oil. $^1$H NMR (400 MHz, CD$_3$CN): (δ=1.21 (t, J$_{H-H}$=7.0 Hz, 3H, OEt), 1.38 (s, 9H, tBu), 2.05-2.25 (m, 2H, CH$_2$), 2.39 (d, J$_{H-P}$=8.2 Hz, 3H, NMe), 2.78-2.94 (m, 2H, NCH$_2$), 2.93 (s, 12H, 2×NMe$_2$), 3.74-3.98 (m, 2H, OEt), 4.25 (d, J$_{H-P}$=20.9 Hz, 1H), 6.37 (m, J$_{H-H}$=2.2 Hz, 2H$_{ar}$), 6.50 (dd, J$_{H-H}$=8.7 Hz and 2.6 Hz, 2H$_{ar}$), 7.05 (dd, J$_{H-H}$=8.6 Hz and 2.4 Hz, 1H$_{ar}$), 7.15 (dd, J$_{H-H}$=8.5 Hz and 2.5 Hz, 1H$_{ar}$) ppm. $^{31}$P NMR (162 MHz, CD$_3$CN): δ=26.9 ppm. HPLC: t$_R$=7.8 min (84%), B/A=30/70-100/0 in 25 min, column 4×250 mm, 1.2 mL/min, detection at 254 nm.

3-[[[3,6-Bis(dimethylamino)-9H-xanthen-9-yl] (ethoxy)phosphoryl]methyl)amino]-propanoic acid (10c)

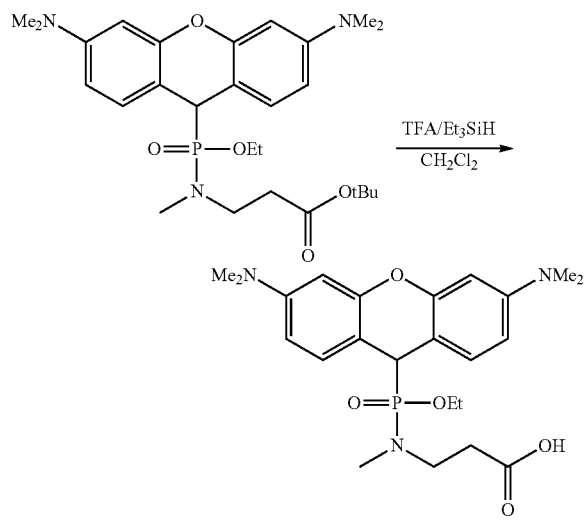

Compound 10c. To a solution of compound 10b (33 mg; 0.064 mmol) in CH$_2$Cl$_2$ (1 mL) Et$_3$SiH (37 mg; 0.319 mmol) and TFA (1 mL) were added dropwise. The resulting reaction mixture stirred for 1.5 h at r.t., and all volatiles were removed in vacuo. The residue was subjected to column chromatography (25 g of SiO$_2$, CH$_2$Cl$_2$/MeOH 10:1) to afford 27 mg (92%) of a bluish solid. $^1$H NMR (400 MHz, CD$_3$CN): δ=1.20 (t, J$_{H-H}$=7.0 Hz, 3H, OEt), 2.09-2.24 (m, 2H, CH$_2$), 2.39 (d, J$_{H-P}$=8.1 Hz, 3H, NMe), 2.75-3.07 (m, 2H, NCH$_2$), 2.93 (s, 12H, NMe$_2$), 3.74-3.97 (m, 2H, OEt), 4.31 (d, J$_{H-P}$=21.1 Hz), 6.38-6.43 (m, 2H$_{ar}$), 6.49-6.55 (m, 2H$_{ar}$), 7.02-7.09 (m, 1H$_{ar}$), 7.12-7.18 (m, 1H$_{ar}$) ppm. $^{31}$P NMR (162 MHz, CD$_3$CN): δ=27.3 ppm. MS (ESI): m/z (negative mode, rel. int., %)=460.4 (100) [M-H]$^-$.

9-[[(2-Carboxyethyl)(methyl)amino]ethoxy)phosphoryl]-3,6-bis(dimethylamino)-9H-xanthenylium trifluoroacetate (10)

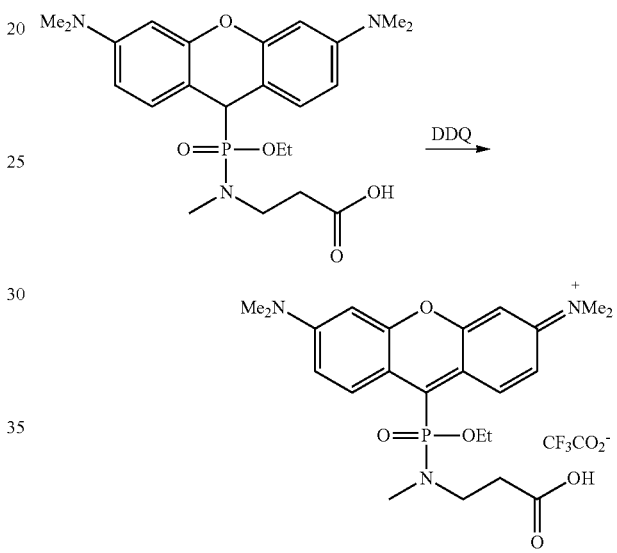

Compound 10. To a solution of compound 10c (25 mg; 0.054 mmol) in MeCN (1 mL) DDQ (12 mg; 0.054 mmol) was added at 0° C. The resulted mixture was stirred for 30 min at r.t. and was then directly subjected to column chromatography (15 g of SiO$_2$, MeCN→MeCN/H$_2$O 1:1+0.1 v/v % of TFA to yield 22 mg (80%) of a dark violet solid. $^1$H NMR (400 MHz, CDCl$_3$): δ=1.41 (t, J$_{H-H}$=7.3 Hz, 3H, OEt), 2.54-2.73 (m, 2H, CH$_2$), 2.80 (d, J$_{H-P}$=10.8 Hz, 3H, NMe), 3.27-3.50 (m, 2H, NCH$_2$), 3.37 (s, 12H, 2×NMe$_2$), 4.18-4.37 (m, 2H, OEt), 6.74 (s, broad, 2H$_{ar}$), 7.18 (dd, J$_{H-H}$=9.9 Hz, J$_{H-P}$=2.3 Hz, 2H$_{ar}$), 8.86 (d, J$_{H-H}$=9.9 Hz, 2H$_{ar}$) ppm. $^{31}$P NMR (162 MHz, CDCl$_3$): δ=17.7 ppm. MS (ESI): m/z (positive mode, rel. int., %)=460.2 (100) [M-Cl]$^+$. HPLC: t$_R$=16.0 min (95%), B/A=20/80-100/0 in 25 min, column 4×250 mm, 1.2 mL/min, detection at 636 nm. UV/Vis (MeCN): λ$_{max}$ (ε)=615 nm (22224 M$^{-1}$cm$^{-1}$); fluorescence (MeCN): λ$_{excit}$=600 nm, λ$_{em}$=652 nm, Φ$_{fl}$=0.46. Standard: Nile Blue, Φ$_{fl}$=0.27 (MeOH). UV/Vis (PBS 7.4): λ$_{max}$ (ε)=625 nm (13816 M$^{-1}$cm$^{-1}$); fluorescence (PBS 7.4): λ$_{excit}$=610 nm, λ$_{em}$=670 nm, Φ$_{fl}$=0.17. Standard: Nile Blue, Φ$_{fl}$=0.27 (MeOH).

9-[[[(2-Carboxyethyl)(methyl)amino]ethoxy)phosphoryl]-3,6-bis(dimethylamino)-9H-xanthenylium trifluoroacetate NHS ester (10-NHS)

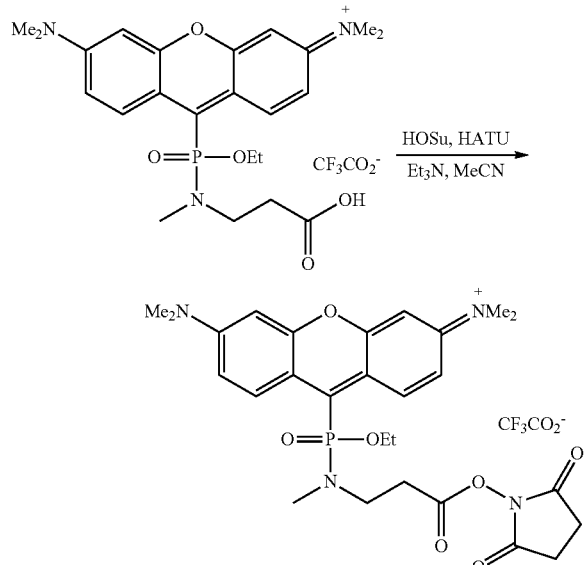

Compound 10-NHS. To a solution of compound 10 (10 mg; 0.020 mmol) in MeCN (1 mL), N-hydroxysuccinimide (35 mg; 0.30 mmol), HATU (30 mg; 0.08 mmol) and Et$_3$N (36 mg; 0.36 mmol) were added at r.t. under Ar. After stirring for 30 min, the reaction mixture was quenched with AcOH (21 µL), diluted with CH$_2$Cl$_2$ and washed with water (2×). The organic layer was dried with Na$_2$SO$_4$ and evaporated to give 10 mg (85%) of crude blue material. HPLC analysis (B/A=30/70-100/0 in 25 min, column 4×250 mm, 1.2 mL/min, detection at 636 nm) showed the presence of two substances with $t_R$=6.6 min (10%; the starting material) and $t_R$=8.6 min (90%; the title compound). After purification by preparative HPLC, 3 mg (25%) of a violet solid were isolated. MS (ESI): m/z (positive mode, rel. int., %)=557.2 (100) [M−Cl]$^+$. HPLC: $t_R$=8.6 min (94%), B/A=30/70-100/0 in 25 min, column 4×250 mm, 1.2 mL/min, detection at 254 nm.

Ethyl [3,6-bis(dimethylamino)-9H-xanthenylium-9-yl]phosphonate (11)

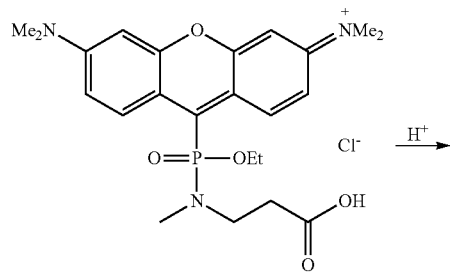

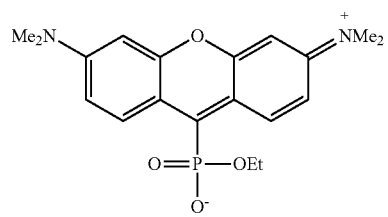

Compound 11. Solutions of compound 10 in protic solvents (MeOH, H$_2$O) spontaneously decompose (particularly in the presence of acids) with formation of compound 11. $^1$H NMR (400 MHz, CD$_3$CN): δ=1.04 (t, $J_{H-H}$=7.0 Hz, 3H, OEt), 3.27 (s, 12H, 2×NMe$_2$), 3.79 (dt, $J_{H-P}$=14.2 Hz, $J_{H-H}$=7.2 Hz, 2H, OEt), 6.77-6.80 (m, 2H$_{ar}$), 7.18 (dd, $J_{H-H}$=9.8 Hz, $J_{H-H}$=2.6 Hz, 2H$_{ar}$), 9.04 (d, $J_{H-H}$=9.8 Hz, 2H$_{ar}$) ppm. $^{31}$P NMR (162 MHz, CD$_3$CN): δ=3.7 ppm. MS (ESI): m/z (positive mode, rel. int., %)=375.1 (100) [M+H]$^+$, 397.2 (47) [M+Na]$^+$. UV/Vis (MeCN): λ$_{max}$ (ε)=565 nm (63519 M$^{-1}$cm$^{-1}$); fluorescence (MeCN): λ$_{excit}$=550 nm, λ$_{em}$=595 nm, Φ$_{fl}$=0.44. Standard: Atto Rho11, Φ$_{fl}$=0.80 (H$_2$O). UV/Vis (PBS 7.4): λ$_{max}$ (ε)=597 nm (66564 M$^{-1}$cm$^{-1}$); fluorescence (PBS 7.4): λ$_{excit}$=580 nm, λ$_{em}$=633 nm, Φ$_{fl}$=0.22. Standard: Atto 594, Φ$_{fl}$=0.85 (H$_2$O).

Allyl 4-[(dimethoxyphosphino)oxy]butanoate (12a)

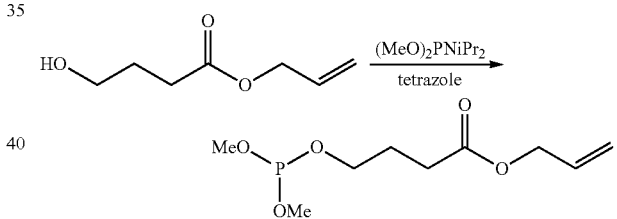

Compound 12a. To a solution of allyl 4-hydroxybutyrate (100 mg; 0.69 mmol) in CH$_2$Cl$_2$ (7 mL) a solution of tetrazole (0.45 M; 6.4 mL; 2.89 mmol) in MeCN and dimethyl N,N-diisopropylphosphoramidite (306 mg; 1.59 mmol) were added under Ar. The reaction mixture was stirred for 1 h at r.t., and then sat. aq. NaHCO$_3$ was added (~10 mL). The organic layer was separated, and the aq. layer was extracted with CH$_2$Cl$_2$ (2×). Combined organic solutions were dried with Na$_2$SO$_4$ and evaporated. The residue was subjected to column chromatography (10 g of SiO$_2$, hexane/EtOAc 6:1) to yield 103 mg (63%) of colorless oil. $^1$H NMR (400 MHz, CD$_3$CN): δ=1.84-1.92 (m, 2H, CH$_2$), 2.42 (t, $J_{H-H}$=7.3 Hz, 2H, CH$_2$), 3.47 (d, $J_{H-P}$=10.6 Hz, 6H, 2×OMe), 3.81 (dt, $J_{H-P}$=7.5 Hz, $J_{H-H}$=6.3 Hz, 2H, OCH$_2$), 4.56 (dt, $J_{H-H}$=5.5 and 1.5 Hz, 2H, OAll), 5.22 (m, $J_{H-H}$=10.5 and 1.4 Hz, 1H, OAll), 5.31 (m, $J_{H-H}$=17.3 and 1.6 Hz, 1H, OAll), 5.95 (m, $J_{H-H}$=17.3, 10.5 and 5.5 Hz, 1H, OAll) ppm. $^{31}$P NMR (162 MHz, CD$_3$CN): δ=140.1 ppm.

9-[[4-(Allyloxy)-4-oxobutoxy](methoxy)phosphoryl]-3,6-bis(dimethylamino)-9H-xanthen-9-ylium chloride (12)

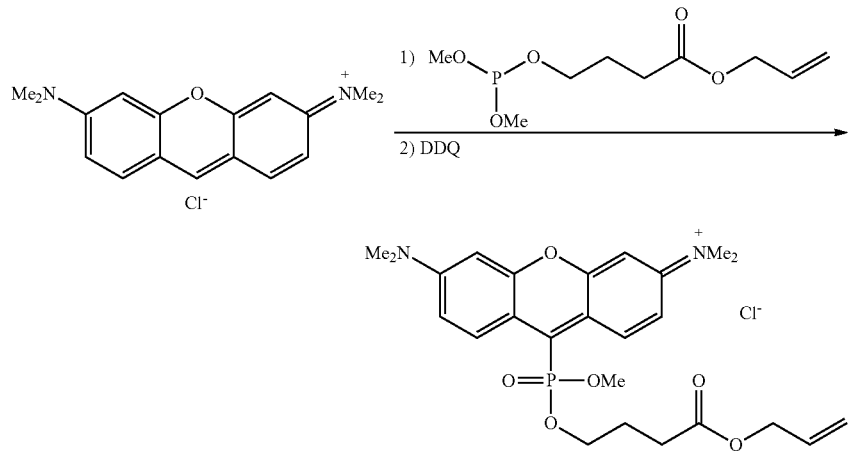

Compound 12. In a screw-cap test tube to a suspension of Pyronin Y (50 mg; 0.165 mmol) in MeCN (1 mL) the compound 12a (58 mg; 0.247 mmol) was added at r.t. under argon. The resulting mixture was stirred overnight at 50° C. After cooling down to 0° C., DDQ (56 mg; 0.165 mmol) was added, and the reaction mixture was stirred for additional 10 min at 0° C. After warming up to r.t., the reaction mixture was directly subjected to column chromatography on $SiO_2$ (30 g; MeCN→MeCN/$H_2O$ 20:1) to afford 20 mg (23%) of a violet solid. $^1$H NMR (400 MHz, $CD_3CN$): δ=1.92-1.97 (m, 2H, $CH_2$, overlapped with solvent signal), 2.35-2.41 (m, $J_{H-H}$=7.3, 7.1 and 3.8 Hz, 2H, $CH_2$), 3.31 (s, 12H, 2×$NMe_2$), 3.84 (d, $J_{H-P}$=11.6 Hz, 3H, OMe), 4.18 (ddt, $J_{H-P}$=10.3 Hz, $J_{H-H}$=7.8 and 6.3 Hz, 1H, $OCH_2$), 4.28 (ddt, $J_{H-P}$=10.3 Hz, $J_{H-H}$=7.5 and 6.2 Hz, 1H, $OCH_2$), 4.47-4.50 (m, $J_{H-H}$=5.4 and 1.5 Hz, 2H, OAll), 5.16-5.21 (m, $J_{H-H}$=10.5 and 1.4 Hz, 1H, OAll), 5.22-5.28 (m, $J_{H-H}$=17.3 and 1.6 Hz, 1H, OAll), 5.83-5.93 (m, $J_{H-H}$=17.2, 10.8 and 5.5 Hz, 1H, OAll), 6.77 (m, $J_{H-H}$=2.4 Hz, 2$H_{ar}$), 7.15 (dd, $J_{H-H}$=9.9 and 2.6 Hz, 2$H_{ar}$), 8.72 (d, $J_{H-H}$=9.9 Hz, 2$H_{ar}$) ppm. $^{31}$P NMR (162 MHz, $CD_3CN$): δ=12.5 ppm. MS (ESI): m/z (positive mode, rel. int., %)=487.2 (100) [M–Cl]$^+$. HPLC: $t_R$=12.2 min (95%), B/A=30/70-100/0 in 25 min, column 4×250 mm, 1.2 mL/min, detection at 600 nm. UV/Vis (MeCN): $\lambda_{max}$ (ε)=621 nm (42690 M$^{-1}$cm$^{-1}$); fluorescence (MeCN): $\lambda_{excit}$=610 nm, $\lambda_{em}$=653 nm, $\Phi_{fl}$=0.32. Standard: Atto 633, $\Phi_{fl}$=0.64 ($H_2O$). UV/Vis (PBS 7.4): $\lambda_{max}$ (ε)=632 nm (29540 M$^{-1}$cm$^{-1}$); fluorescence (PBS 7.4): $\lambda_{excit}$=620 nm, $\lambda_{em}$=669 nm, $\Phi_{fl}$=0.17. Standard: Atto 633, $CD_{fl}$=0.64 ($H_2O$).

[3,6-Bis(dimethylamino)-9H-xanthen-9-yl]phosphinic acid (13a)

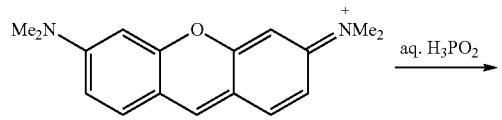

-continued

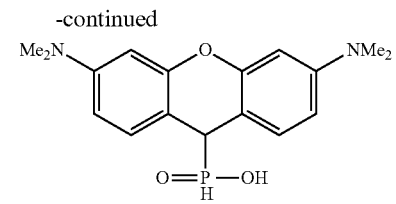

Compound 13a. A solution of Pyronin Y (1 g; 3.3 mmol) in aq. $H_3PO_2$ (50%, 4.4 g; 33.3 mmol) was stirred overnight at 100° C. After cooling down to r.t., the reaction mixture was diluted with $H_2O$ (~25 mL) and subjected to reverse-phase column chromatography (100 g of RP—$SiO_2$, $H_2O$→$H_2O$/MeCN 5:1+0.1 v/v % of TFA to yield 1031 mg (94%) of the title product as a red solid. $^1$H NMR (400 MHz, $CD_3OD$): δ=3.06 (s, 12H, 2×$NMe_2$), 4.30 (d, $J_{H-P}$=15.5 Hz, 1H), 7.03-7.11 (m, 4$H_{ar}$), 7.37-7.43 (m, 2$H_{ar}$) ppm. With addition of $NEt_3$ (1 eq.): $^1$H NMR (400 MHz, $CD_3OD$): δ=1.15 (t, $J_{H-H}$=7.2 Hz, 9H, $NEt_3$), 2.88 (s, 12H, 2×$NMe_2$), 2.90-2.99 (m, 6H, $NEt_3$), 3.82 (d, $J_{H-P}$=15.5 Hz, 1H), 6.39 (d, $J_{H-H}$=2.5 Hz, 2$H_{ar}$), 6.49 (dd, $J_{H-H}$=8.5 and 2.6 Hz, 2$H_{ar}$), 6.76 (d, $J_{H-P}$=504 Hz, 1H, PH) 7.11 (dd, $J_{H-H}$=8.5 Hz, $J_{H-P}$=2.0 Hz, 2$H_{ar}$) ppm. $^{31}$P NMR (162 MHz, $CD_3OD$): δ=26.4 ppm. MS (ESI): m/z (positive mode, rel. int., %)=333.1 (100) [M+H]$^+$. MS (ESI): m/z (negative mode, rel. int., %)=331.2 (100) [M–H]$^-$.

[3,6-Bis(dimethylamino)-9H-xanthenylium-9-yl] phosphinate (13)

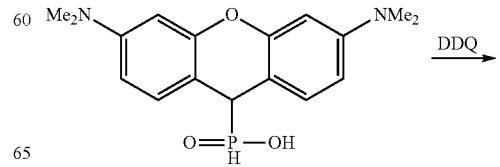

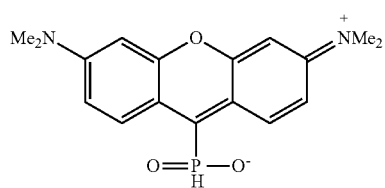

Compound 13. To a solution of compound 13a (50 mg; 0.15 mmol) in MeOH (2 mL) DDQ (36 mg; 0.16 mmol) was added at 0° C. After stirring for 15 min, all volatiles were removed in vacuo, and the residue was dissolved in aq. NaHCO$_3$ (~50 mL). This solution was extracted with CH$_2$Cl$_2$ (4×50 mL), the aq. layer was acidified with conc. HCl to pH 0, saturated with NaCl and again extracted with CH$_2$Cl$_2$ (4×50 mL). The combined organic extracts from the second extraction were evaporated. The residue was subjected to reverse-phase column chromatography (25 g of RP—SiO$_2$, MeCN/H$_2$O 1:1) to give 30 mg (61%) of a violet powder. Et$_3$N (1 eq.) was added to the NMR samples. $^1$H NMR (400 MHz, CD$_3$OD): δ=1.28 (t, $J_{H-H}$=7.3 Hz, 9H, NEt$_3$), 3.17 (q, $J_{H-H}$=7.3 Hz, 6H, NEt$_3$), 3.29 (s, 12H, 2×NMe$_2$), 6.79-6.83 (m, 2H$_{ar}$), 7.13 (dd, $J_{H-H}$=9.7 Hz and 2.6 Hz, 2H$_{ar}$), 8.32 (d, $J_{H-P}$=547 Hz, 1H, PH) 8.71 (d, $J_{H-H}$=9.7 Hz, 2H$_{ar}$) ppm. $^{31}$P NMR (162 MHz, CD$_3$OD): δ=2.1 ppm. MS (ESI): m/z (positive mode, rel. int., %)=331.1 (85) [M+H]$^+$, 353.1 (100) [M+Na]$^+$. UV/Vis (PBS 7.4): λ$_{max}$ (ε)=590 nm (59543 M$^{-1}$cm$^{-1}$); fluorescence (PBS 7.4): λ$_{excit}$=560 nm, λ$_{em}$=627 nm, Φ$_{fl}$=0.33. Standard: Oxazine 4, Φ$_{fl}$=0.63 (MeOH).

tert-Butyl 2-[[3,6-bis(dimethylamino)-9H-xanthen-9-yl](ethoxy)phosphoryl]acetate (14a)

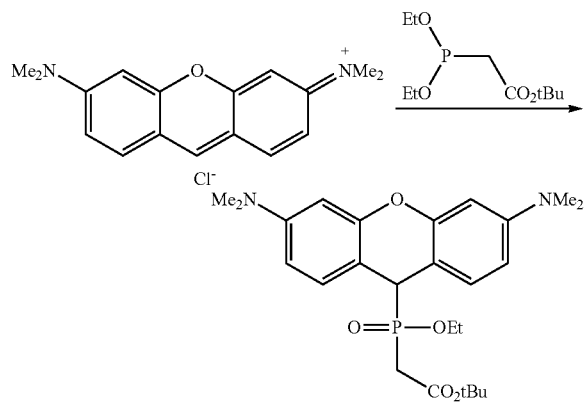

Compound 14a. In a screw-cap test tube to a suspension of Pyronin Y (50 mg; 0.165 mmol) in DMF (1 mL) tert-butyl 2-diethoxyphosphinoacetate (117 mg; 0.49 mmol) was added at r.t. under argon. The resulted mixture stirred overnight at 60° C. After cooling down to r.t., the reaction mixture was diluted with water (~50 mL) and extracted with Et$_2$O (3×50 mL). The combined ethereal solutions were dried with Na$_2$SO$_4$ and evaporated. The residue was subjected to column chromatography (20 g of SiO$_2$, n-hexane/EtOAc 1:3) to give brown oil which was dried in vacuo overnight. Yield 35 mg (45%). $^1$H NMR (400 MHz, CD$_3$CN): δ=1.15 (t, =7.0 Hz, 3H, OEt), 1.46 (s, 9H, tBu), 2.65 (dd, $J_{H-P}$=14.7 Hz, $J_{H-H}$=13.9 Hz, 1H), 2.69 (dd, $J_{H-H}$=14.9 Hz, $J_{H-H}$=13.9 Hz, 1H), 2.94 (s, 12H, 2×NMe$_2$), 3.78-3.95 (m, 2H, OEt), 4.39 (d, $J_{H-P}$=15.8 Hz, 1H), 6.40 (s, broad, 1H$_{ar}$), 6.41 (s, broad, 1H$_{ar}$), 6.51-6.56 (m, 2H$_{ar}$), 7.15 (dd, $J_{H-H}$=8.6 Hz, $J_{H-P}$=2.3 Hz, 1H$_{ar}$), 7.22 (dd, $J_{H-H}$=8.6 Hz, $J_{H-P}$=2.4 Hz, 1H$_{ar}$) ppm. $^{31}$P NMR (162 MHz, CD$_3$CN): δ=41.5 ppm. MS (ESI): m/z (positive mode, rel. int., %)=497.2 (100) [M+Na]$^+$.

2-[[3,6-Bis(dimethylamino)-9H-xanthenylium-9-yl](ethoxy)phosphoryl]acetate (14)

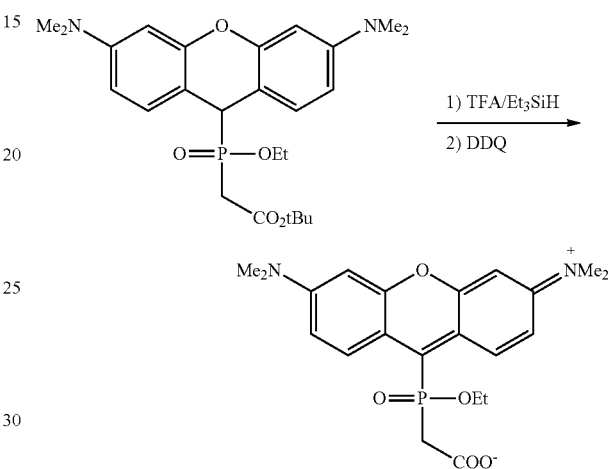

Compound 14. To a solution of compound 14a (18 mg; 0.038 mmol) in CH$_2$Cl$_2$ (1 mL) Et$_3$SiH (26 mg; 0.22 mmol) and TFA (1 mL) were added dropwise. The resulting reaction mixture was stirred for 1.5 h at r.t., and all volatiles were removed in vacuo. The residue was dissolved in MeCN (~3 mL), the resulting solution was cooled down in an ice bath, and DDQ (10 mg; 0.046 mmol) was added. After 30 min stirring at 0° C., the reaction mixture was directly subjected to column chromatography (20 g of SiO$_2$, MeCN→MeCN/H$_2$O+0.1 v/v % of TFA). Fractions containing the blue substance were combined and freeze-dried. In order to get rid of residual SiO$_2$, the product was dissolved in water, the resulted solution was saturated with NH$_4$Cl and extracted with CH$_2$Cl$_2$ (5×). Combined organic solutions were dried with Na$_2$SO$_4$ and evaporated to afford 10 mg (63%) of a blue solid. $^1$H NMR (400 MHz, CD$_3$CN): δ=1.33 (t, $J_{H-H}$=7.0 Hz, 3H, OEt), 3.29 (s, 12H, 2×NMe$_2$), 3.43-3.57 (m, 2H, CH$_2$), 4.09 (ddt, $J_{H-P}$=15.1 Hz, $J_{H-H}$=10.2 and 7.0 Hz, 1H, OEt), 4.30 (ddt, $J_{H-P}$=15.2 Hz, $J_{H-H}$=10.3 and 7.0 Hz, 1H, OEt), 6.74-6.77 (m, 2H$_{ar}$), 7.15 (dd, $J_{H-H}$=9.9 and 2.7 Hz, 2H$_{ar}$), 8.85 (d, $J_{H-H}$=9.9 Hz, 2H$_{ar}$) ppm. $^{31}$P NMR (162 MHz, CD$_3$CN): δ=31.4 ppm. MS (ESI): m/z (positive mode, rel. int., %)=417.1 (100) [M+H]$^+$. UV/Vis (MeCN): λ$_{max}$ (ε)=625 nm (22599 M$^{-1}$cm$^{-1}$); fluorescence (MeCN): λ$_{excit}$=620 nm, λ$_{em}$=656 nm, Φ$_{fl}$=0.32. Standard: Atto 633, Φ$_{fl}$=0.64 (H$_2$O). UV/Vis (PBS 7.4): λ$_{max}$ (ε)=631 nm (47622 M$^{-1}$cm$^{-1}$); fluorescence (PBS 7.4): λ$_{excit}$=620 nm, λ$_{em}$=667 nm, Φ$_{fl}$=0.22. Standard: Nile Blue, Φ$_{fl}$=0.27 (MeOH).

Bis(triethylammonium) 3-[[3,6-bis(dimethylamino)-9H-xanthen-9-yl]oxidophosphoryl]-propanoate (15a)

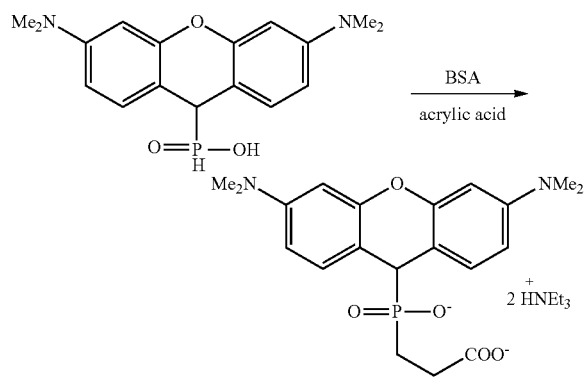

Compound 15a. To a suspension of compound 13a (73 mg; 0.22 mmol) in CH$_2$Cl$_2$ (1 mL) acrylic acid (60 mg; 0.82 mmol) and N,O-bis(trimethylsilyl)acetimidate (BSA; 380 mg, 1.87 mmol) were added dropwise at 0° C. under Ar. A clear red solution formed. After stirring at r.t. overnight, the reaction mixture was quenched with MeOH (~1 mL) at 0° C. and evaporated. The oily residue was subjected to reverse-phase column chromatography (30 g of RP—SiO$_2$, MeCN/H$_2$O 1:10+0.1 v/v % of NEt$_3$). Fractions containing the title product were evaporated, and the residue was redissolved in MeOH. The methanolic solution was filtered through a fine sintered glass filter and evaporated to afford 67 mg (50%) of a blue amorphous solid. $^1$H NMR (400 MHz, CD$_3$OD): δ=1.13-1.19 (m, 18H, 2×NEt$_3$), 1.58-1.67 (m, 2H, CH$_2$), 2.25-2.33 (m, 2H, CH$_2$), 2.88 (s, 12H, 2×NMe$_2$), 2.93-3.01 (m, 12H, 2×NEt$_3$), 3.90 (d, J$_{H-P}$=19.5 Hz), 6.39 (m, 2H$_{ar}$), 6.49 (d, J$_{H-H}$=8.5 Hz, 1H$_{ar}$), 6.50 (d, J$_{H-H}$=8.5 Hz, 1H$_{ar}$), 7.16-7.23 (m, 2H$_{ar}$) ppm. $^{31}$P NMR (162 MHz, CD$_3$OD): δ=37.3 ppm. MS (ESI): m/z (negative mode, rel. int., %)=403.4 (100) [M−2NEt$_3$−H]$^-$.

[3,6-Bis(dimethylamino)-9H-xanthenyhum-9-yl](2-carboxyethyl)phosphinate (15)

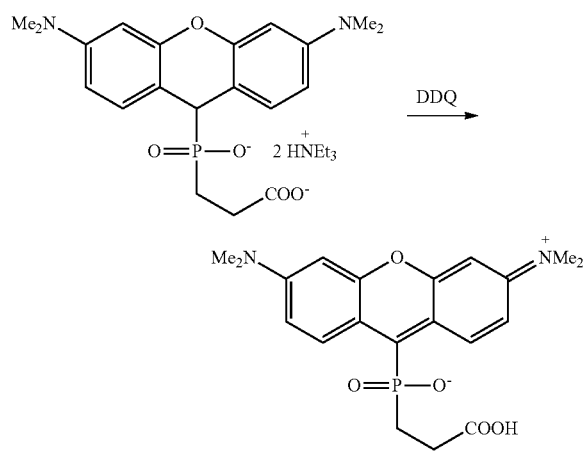

Compound 15. To a solution of compound 15a (67 mg; 0.11 mmol) in MeCN (3 mL) DDQ (25 mg; 0.11 mmol) was added at 0° C. The resulting mixture was stirred at r.t. for 15 min and was then directly subjected to column chromatography (30 g of SiO$_2$, MeCN→MeCN/H$_2$O 10:1+0.1 v/v % of TFA→2:1+0.1 v/v % of TFA). Fractions containing the title compound were evaporated, and the residue was dissolved in H$_2$O (~20 mL). The solution was saturated with NaCl, acidified with TFA (~1 mL) and extracted with CH$_2$Cl$_2$ (3×50 mL). The combined organic extracts were evaporated to give 34 mg (77%) of a violet solid. $^1$H NMR (400 MHz, CD$_3$OD): δ=2.09-2.22 (m, 2H, CH$_2$), 2.45-2.58 (m, 2H, CH$_2$), 3.28 (s, 12H, 2×NMe$_2$), 6.77 (s, 2H$_{ar}$), 7.11 (d, J$_{H-H}$=9.0 Hz, 2H$_{ar}$), 9.19 (d, J$_{H-H}$=9.0 Hz, 2H$_{ar}$) ppm. MS (ESI): m/z (positive mode, rel. int., %)=403.1 (100) [M+H]$^+$. UV/Vis (PBS 7.4): λ$_{max}$ (ε)=598 nm (52094 M$^{-1}$cm$^{-1}$); fluorescence (PBS 7.4): λ$_{excit}$=560 nm, λ$_{em}$=636 nm, Φ$_{fl}$=0.29. Standard: Oxazine 4, Φ$_{fl}$=0.63 (MeOH).

tert-Butyl 6-(N-methylacrylamido)hexanoate (16a)

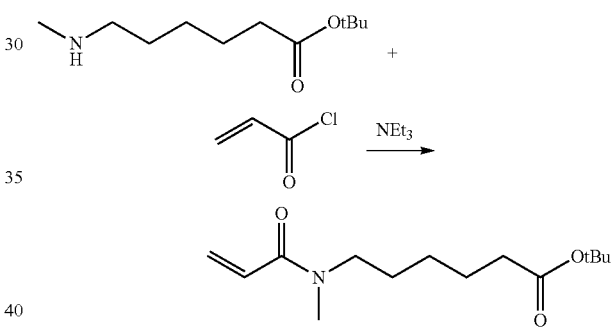

Compound 16a. To a solution of tert-butyl 6-(methylamino)hexanoate [prepared according to Epstein, M. G.; Reeves, B. D.; Maaty, W. S.; Fouchard, D.; Dratz, E. A.; Bothner, B.; Grieco, P. A. *Bioconjugate Chem.* 2013, 24, 1552-1561] (600 mg; 2.98 mmol) and Et$_3$N (391 mg; 3.87 mmol) in CH$_2$Cl$_2$ (5 mL) a solution of acryloyl chloride (324 mg; 3.58 mmol) in CH$_2$Cl$_2$ (5 mL) was added dropwise at 0° C. under vigorous stirring. The resulting mixture was stirred overnight at r.t., diluted with Et$_2$O, filtered through a glass filter and evaporated. The residue was subjected to column chromatography (30 g of SiO$_2$, n-hexane/EtOAc 1:2) to afford 657 mg (86%) as colorless oil. $^1$H NMR (400 MHz, CDCl$_3$): δ=1.28-1.36 (m, 2H, CH$_2$), 1.43 (s, 9H, tBu), 1.54-1.65 (m, 4H, 2×CH$_2$), 2.21 (t, J$_{H-H}$=7.4 Hz, 2H, CH$_2$), 3.00 (br.s, 3H, NMe), 3.29-3.48 (m, 2H, NCH$_2$), 5.66 (dd, J$_{H-H}$=10.4 and 2.0 Hz, 1H), 6.31 (dd, J$_{H-H}$=16.7 and 1.9 Hz, 1H), 6.55 (dd, J$_{H-H}$=16.7 and 10.4 Hz, 1H) ppm. MS (ESI): m/z (positive mode, rel. int., %)=278.2 (100) [M+Na]$^+$. HRMS (C$_{14}$H$_{25}$NO$_3$P): m/z (positive mode)= 278.1721 (found [M+Na]$^+$), 278.1727 (calc.).

Triethylammonium [3,6-bis(dimethylamino)-9H-xanthen-9-yl][3-[(6-tert-butoxy-6-oxohexyl)(methypamino]-3-oxopropyl]phosphinate (16b)

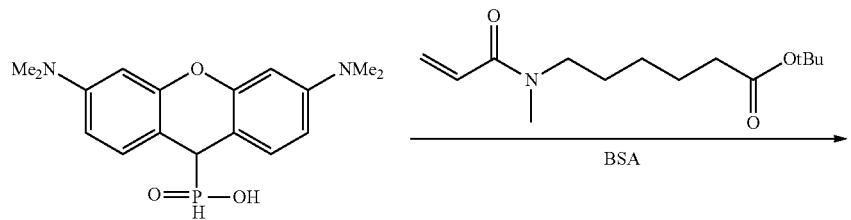

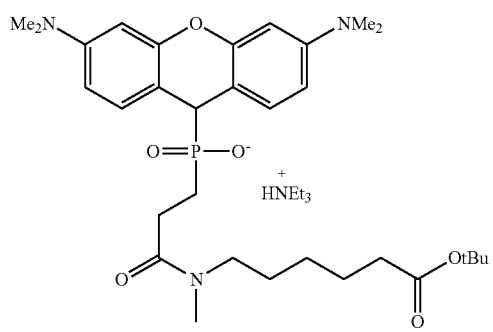

Compound 16b. To a suspension of compound 13a (100 mg; 0.30 mmol) and compound 16a (288 mg; 1.13 mmol) in CH$_2$Cl$_2$ (2 mL), N,O-bis(trimethylsilyl)acetimidate (BSA; 457 mg, 2.25 mmol) was added dropwise at 0° C. under argon. A clear red solution formed. After stirring at r.t. overnight and at 40° C. for 3 h, the reaction mixture was quenched with MeOH (~5 mL) at 0° C. and evaporated. The oily residue was subjected to reverse-phase column chromatography (30 g of RP—SiO$_2$, MeCN/H$_2$O 3:1+0.1 v/v % of NEt$_3$). Fractions containing the title product were evaporated, and the residue was redissolved in MeOH. The methanolic solution was filtered through a fine sintered glass filter and evaporated to afford 30 mg (14%) of a red amorphous solid. $^1$H NMR (400 MHz, CD$_3$OD), mixture of 2 rotameric forms: δ=1.23 (t, J$_{H-H}$=7.3 Hz, 9H, NEt$_3$), 1.25-1.34 (m, 2H, CH$_2$), 1.42 (s, 9H, tBu), 1.49-1.64 (m, 6H, 3×CH$_2$), 2.15-2.27 (m, 4H, 2×CH$_2$), 2.79 (s, 3H, NMe), 2.89 (m, 12H, NMe$_2$), 3.09 (q, J$_{H-H}$=7.3 Hz, 6H, NEt$_3$), 3.31-3.44 (m, 2H, CH$_2$), 3.93 (d, J$_{H-P}$=23.1 Hz, 1H), 6.37-6.40 (m, 2H$_{ar}$), 6.48-6.52 (m, 2H$_{ar}$), 7.23-7.28 (m, $^2$H$_{ar}$) ppm $^{31}$P NMR (162 MHz, CD$_3$OD), mixture of 2 rotameric forms: δ=39.0 (minor), 39.1 (major) ppm. MS (ESI): m/z (negative mode, rel. int., %)=586.3 (100) [M—NEt$_3$—H]$^-$. HRMS (C$_{31}$H$_{46}$N$_3$O$_6$P): m/z (negative mode)=586.3044 (found [M—NEt$_3$-H]$^+$), 586.3051 (calc.).

Triethylammonium 6-[3-[[3,6-bis(dimethylamino)-9H-xanthenylium-9-yl]oxidophosphoryl]-N-methyl-propanamido]hexanoate (16)

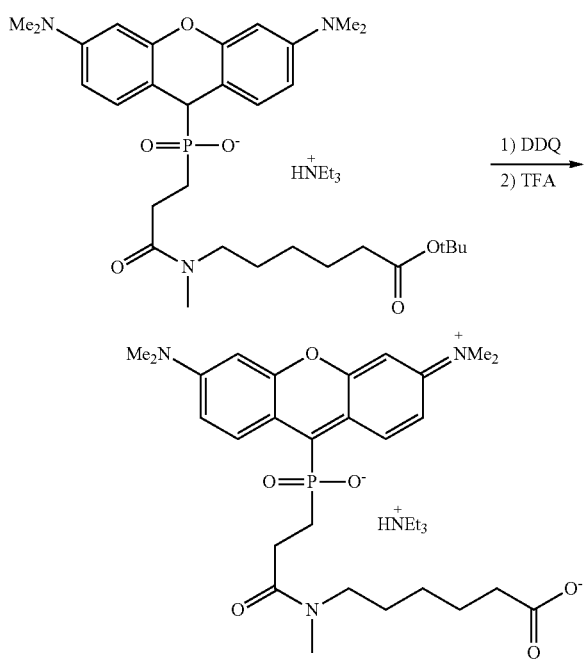

Compound 16. To a solution of compound 16b (30 mg; 0.051 mmol) in MeOH (2 mL) DDQ (12 mg; 0.051 mmol) was added at 0° C. The resulting mixture was stirred for 15 min at r.t. and was then directly subjected to reverse-phase column chromatography (25 g of RP—SiO$_2$, MeCN/H$_2$O 1:2+0.1 v/v % of NEt$_3$→10:1+0.1 v/v % of NEt$_3$). Fractions containing the title product were evaporated, and the residue was redissolved in MeOH. The methanolic solution was filtered through a fine sintered glass filter and evaporated to afford 12 mg of a violet solid. This substance was dissolved in TFA (1 mL) and stirred for 30 min at r.t. The volatiles were evaporated and the residue was subjected to reverse-phase column chromatography (25 g of RP—SiO$_2$, MeCN/H$_2$O 3:1+0.1 v/v % of HCOOH) to yield 8 mg (25%) of a violet solid. MS (ESI): m/z (negative mode, rel. int., %)=528.2 (100) [M−NEt$_3$−H]$^-$. HRMS (C$_{27}$H$_{36}$N$_3$O$_6$P): m/z (negative mode)=528.2256 (found [M−NEt$_3$−H]$^+$), 528.2269 (calc.). HPLC: t$_R$=16.1 min (100%), B/A=20/80-50/50 in 25 min, column 4.0×250 mm, 1.2 mL/min, detection at 592 nm. UV/Vis (PBS 7.4): λ$_{max}$ (ε)=603 nm (10750 M$^{-1}$cm$^{-1}$); fluorescence (PBS 7.4): λ$_{excit}$=565 nm, λ$_{em}$=636 nm, Φ$_{fl}$=0.30. Standard: Oxazine 4, Φ$_{fl}$=0.63 (MeOH).

6-[3-[[3,6-Bis(dimethylamino)-9H-xanthenylium-9-yl]oxidophosphoryl]-N-methylpropanamido]hexanoic acid NHS ester (16-NHS)

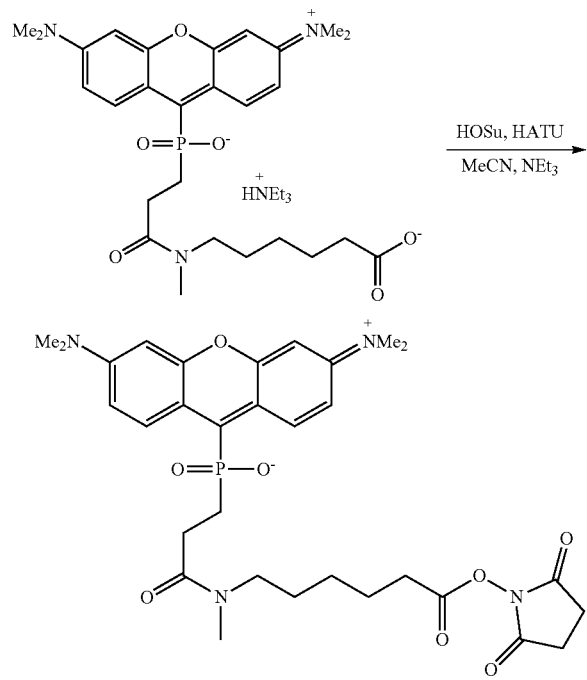

Compound 16-NHS. To a solution of compound 16 (3 mg; 0.006 mmol) in MeCN (1 mL), N-hydroxysuccinimide (10 mg; 0.085 mmol), HATU (9 mg; 0.027 mmol) and NEt$_3$ (10 mg; 0.10 mmol) were added at r.t. under Ar. After stirring for 1 h, the reaction mixture was evaporated to dryness, and the residue was subjected to column chromatography (20 g of SiO$_2$, MeCN/H$_2$O 4:1). Fractions containing the NHS-ester were combined and freeze-dried to give 1 mg (28%) of a dark blue solid. MS (ESI): m/z (positive mode, rel. int., %)=627.1 (45) [M+H]$^+$, 649.1 (100) [M+Na]$^+$. HPLC: t$_R$=21.8 min (70%), B/A=20/80-50/50 in 25 min, column 4.0×250 mm, 1.2 mL/min, detection at 254 nm.

3-[[2[2-(6-chlorohexyloxy)ethoxy]ethyl]amino]-3-oxopropyl[6-(dimethylamino)-3-(dimethyliminio)-3H-xanthen-9-yl]phosphinate (16-Halo)

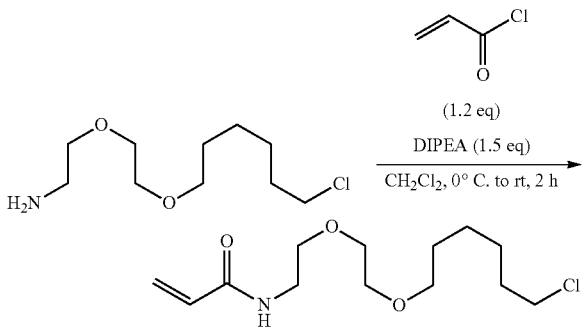

HaloTag(O2)-acrylamide. To a solution of HaloTag® Amine (O2) Ligand [Singh, V.; Wang, S.; Kool, E. T. *J. Am. Chem. Soc.* 2013, 135, 6184-6191] (300 mg, 1.34 mmol) and N-ethyldiisopropylamine (350 µL, 2 mmol) in dry CH$_2$Cl$_2$ (5 mL), cooled in ice-water bath, acryloyl chloride (131 µL, 1.61 mmol) dissolved in dry CH$_2$Cl$_2$ (1 mL) was added dropwise. The reaction mixture was stirred at 0° C. for 30 min and at rt for 2 h. The mixture was then diluted with CH$_2$Cl$_2$ (40 mL), washed with sat. aq. NaHCO$_3$, brine and dried over Na$_2$SO$_4$. The product was isolated by column chromatography (20 g SiO$_2$, gradient 0% to 5% methanol/EtOAc) and dried in vacuo to yield 325 mg (87%) of the product as colorless oil. The material contained ~30% of 3-hydroxypropionamide impurity and was used without further purification. $^1$H NMR (400 MHz, DMSO-d$_6$): δ 8.15 (t, J=5.8 Hz, 1H), 8.05 (t, J=5.2 Hz, impurity), 6.24 (dd, J=17.1, 10.1 Hz, 1H), 6.07 (dd, J=17.1, 2.3 Hz, 1H), 5.56 (dd, J=10.1, 2.3 Hz, 1H), 3.77 (t, J=6.4 Hz, impurity), 3.61 (t, J=6.6 Hz, 2H), 3.53-3.25 (m, 10H), 3.21 (q, J=5.8 Hz, impurity), 2.56 (t, J=6.4 Hz, impurity), 1.75-1.66 (m, 2H), 1.48 (tt, J=8.0, 6.4 Hz, 2H), 1.43-1.24 (m, 4H). $^{13}$C NMR (101 MHz, DMSO-d$_6$): δ 168.9 (impurity), 164.6, 131.7, 125.0, 70.2, 69.6, 69.41 (impurity), 69.40, 69.05 (impurity), 69.02, 45.3, 41.0 (impurity), 38.64 (impurity), 38.61, 38.2 (impurity), 32.0, 29.1, 26.1, 24.9. MS (ESI): m/z (positive mode, rel. int., %)=278.2 (29) [M+H]$^+$, 300.1 (100) [M+Na]$^+$, 316.1 (78) [M+K]$^+$. HRMS (C$_{13}$H$_{24}$NO$_3$Cl): m/z (positive mode)=278.1518 (found [M+H]$^+$), 278.1517 (calc.).

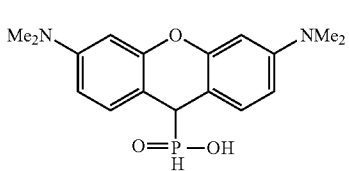

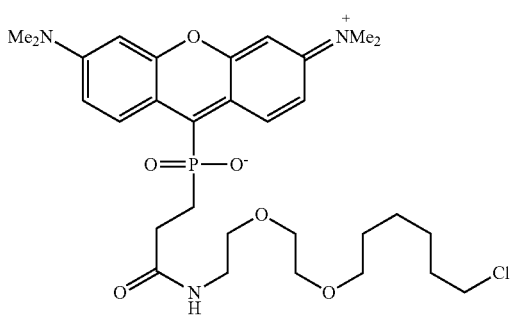

Compound 16-Halo.

To a suspension of 13a (60 mg, 0.18 mmol) in 1,2-dichloroethane (2 mL), cooled in ice-water bath, N,O-bis(trimethylsilyl)acetimidate (BSA; 350 μL, 1.44 mmol) was added quickly dropwise. The resulting clear solution was stirred at 0° C. under $N_2$ atmosphere for 10 min, followed by addition of HaloTag(O2)-acrylamide (278 mg, purity ~70%, ~0.7 mmol) in 1,2-dichloroethane (1.5 mL). The mixture was stirred at 70° C. under $N_2$ atmosphere overnight, the solvent was evaporated, the residue was redissolved in $CH_2Cl_2$ (3 mL), cooled in dry ice-acetone bath followed by addition of DDQ (41 mg, 0.18 mmol) in $CH_2Cl_2$ (3 mL) quickly dropwise. The dark violet mixture was allowed to warm up to rt and stirred for 15 min. Trifluoroacetic acid (50 μL) was added, the mixture was evaporated to dryness and the product was isolated by column chromatography (30 g $SiO_2$, gradient 10% to 30% methanol/$CH_2Cl_2$) and lyophilized from aqueous 1,4-dioxane. Dark violet crystalline solid, yield 53 mg (48%). $^1$H NMR (400 MHz, $CD_3OD$): δ 9.43 (d, J=9.9 Hz, 2H), 7.99 (t, J=5.6 Hz, 1H), 7.13 (dd, J=9.9, 2.7 Hz, 2H), 6.81 (dd, J=2.7, 1.3 Hz, 2H), 3.56-3.51 (m, 6H), 3.43 (t, J=6.5 Hz, 2H), 3.42 (t, J=5.6 Hz, 2H), 3.31 (s, 12H), 3.20 (td, J=5.6, 4.0 Hz, 2H), 2.43-2.34 (m, 2H), 2.16-2.06 (m, 2H), 1.78-1.68 (m, 2H), 1.54 (dq, J=7.6, 6.6 Hz, 2H), 1.47-1.28 (m, 4H). MS (ESI): m/z (positive mode, rel. int., %)=608.3 (48) $[M+H]^+$, 630.3 (53) $[M+Na]^+$, 646.2 (100) $[M+K]^+$. HRMS ($C_{13}H_{24}NO_3Cl$): m/z (positive mode)=608.2653 (found $[M+H]^+$), 608.2651 (calc.).

9-[(Diisopropylamino)(methoxy)phosphoryl]-1H,2H,3H5H,6H,7H,11H,12H,13H,15H,16H,17H-pyrido[3,2,1-ij]quinolizino[1',9':6,7,8]chromeno[2,3-f]quinolinium trifluoroacetate (17) and Methyl (1H,2H,3H,5H,6H,7H,11H,12H,13H,15H,16H,17H-pyrido[3,2,1-ij]quinolizino[1',9':6,7,8]chromeno[2,3-f]quinolinium-9-yl)phosphonate (18)

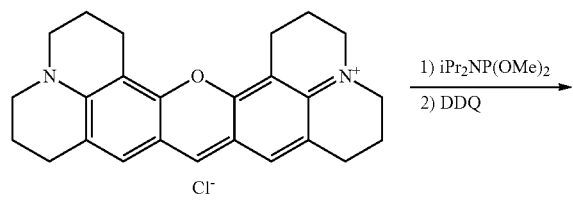

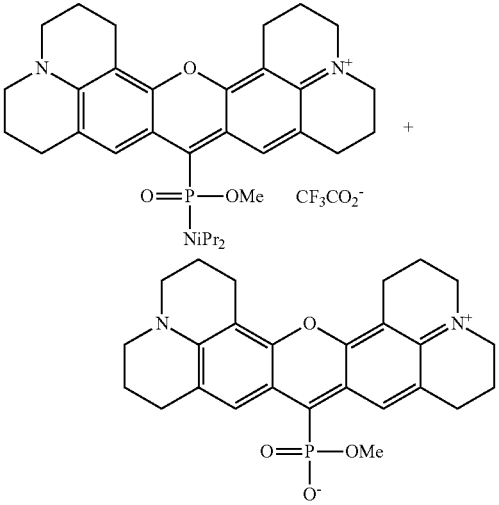

Compounds 17 and 18. In a screw-cap test tube to a suspension of the corresponding pyronine (50 mg; 0.13 mmol) in MeCN (1 mL) dimethyl N,N-diisopropylphosphoramidite (100 mg; 0.52 mmol) was added at r.t. under Ar. The resulting reaction mixture was warmed up to 60° C. and stirred for 2.5 h at this temperature. After cooling down to 0° C., DDQ (116 mg; 0.52 mmol) was added, and the reaction mixture was stirred for additional 10 min at 0° C. After warming up to r.t., the reaction mixture was diluted with MeCN (10 ml) and directly subjected to column chromatography on $SiO_2$ (100 g; MeCN→MeCN/$H_2O$ 20:1+0.1 v/v % of TFA). Fractions containing the title compound were evaporated to dryness, dissolved in water and extracted with $CH_2Cl_2$ (3×). Combined organic solutions were dried with $Na_2SO_4$ and evaporated to yield 40 mg of a dark blue solid. HPLC analysis (B/A=50/50-100/0 in 25 min, column 4×250 mm, 1.2 mL/min, detection at 254 nm) showed the presence of two colored substances: 17 with $t_R$=10.7 min (58%) and 18 with $t_R$=18.3 min (42%). This mixture was subjected to reverse-phase column chromatography (30 g of RP—$SiO_2$, MeCN/$H_2O$ 2:1+0.1 v/v % of TFA→MeCN+0.1 v/v % of TFA→MeOH) to yield 8 mg (10%) of 17 and 7 mg (12%) of 18.

Compound 17: MS (ESI): m/z (positive mode, rel. int., %)=548.3 (100) $[M-Cl]^+$. HRMS ($C_{32}H_{43}N_3O_3P$): m/z (positive mode)=548.3046 (found $[M-Cl]^+$), 548.3037 (calc.). UV/Vis (MeCN): $\lambda_{max}$ (ε)=649 nm (52455 $M^{-1}cm^{-1}$); fluorescence (MeCN): $\lambda_{excit}$=610 nm, $\lambda_{em}$=679 nm, $\Phi_{fl}$=0.25. Standard: Oxazine 1, $\Phi_{fl}$=0.11 (EtOH). UV/Vis (PBS 7.4): $\lambda_{max}$ (ε)=661 nm (46976 $M^{-1}cm^{-1}$); fluorescence (PBS 7.4): $\lambda_{excit}$=650 nm, $\lambda_{em}$=696 nm, $\Phi_{fl}$=0.11. Standard: Atto 655, $\Phi_{fl}$=0.30 ($H_2O$).

Compound 18: $^1$H NMR (400 MHz, $CDCl_3$): δ=1.94-2.02 (m, 4H, 2×$CH_2$), 2.03-2.11 (m, 4H, 2×$CH_2$), 2.84-2.90 (m, 4H, 2×$CH_2$), 2.91-2.98 (m, 4H, 2×$CH_2$), 3.43-3.52 (m, 8H, 4×$CH_2$), 3.59 (d, $J_{H-P}$=11.5 Hz, 3H, OMe), 8.95 (s, 2$H_{ar}$) ppm. $^{31}$P NMR (162 MHz, $CD_3CN$): δ=5.0 ppm. UV/Vis (MeCN): $\lambda_{max}$ (ε)=596 nm (49565 $M^{-1}cm^{-1}$); fluorescence (MeCN): $\lambda_{excit}$=580 nm, $\lambda_{em}$=623 nm, $\Phi_{fl}$=0.85. Standard: Atto 590, $\Phi_{fl}$=0.80 ($H_2O$). UV/Vis (PBS 7.4): $\lambda_{max}$ (ε)=630 nm (52286 $M^{-1}cm^{-1}$); fluorescence (PBS 7.4): $\lambda_{excit}$=620 nm, $\lambda_{em}$=666 nm, $\Phi_{fl}$=0.17. Standard: Atto 637, $CD_{fl}$=0.25 ($H_2O$).

9-[[(2-Carboxyethyl)(methyl)amino](ethoxy)phosphoryl]-1H,2H,3H,5H,6H,7H,11H,12H,13H,15H,16H,17H-pyrido[3,2,1-ij]quinolizino[1',9':6,7,8]chromeno[2,3-f]quinolinium trifluoroacetate (19)

9-[[(2-Carboxyethyl)(methyl)amino](ethoxy)phosphoryl]-1H,2H,3H,5H,6H,7H,11H,12H,13H,15H,16H,17H-pyrido[3,2,1-ij]quinolizino[1',9':6,7,8]chromeno[2,3-f]quinolinium NHS ester trifluoroacetate (19-NHS)

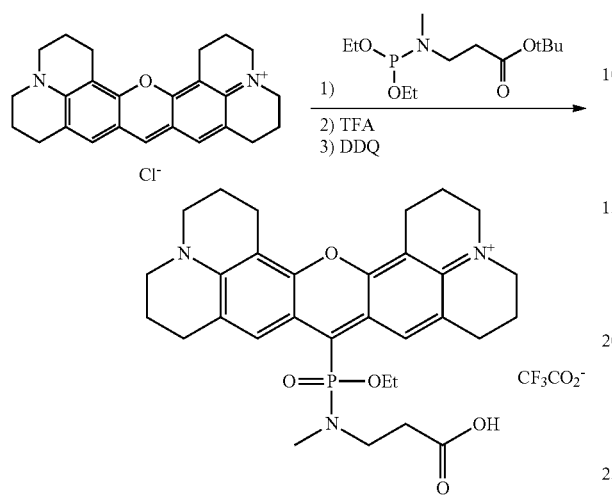

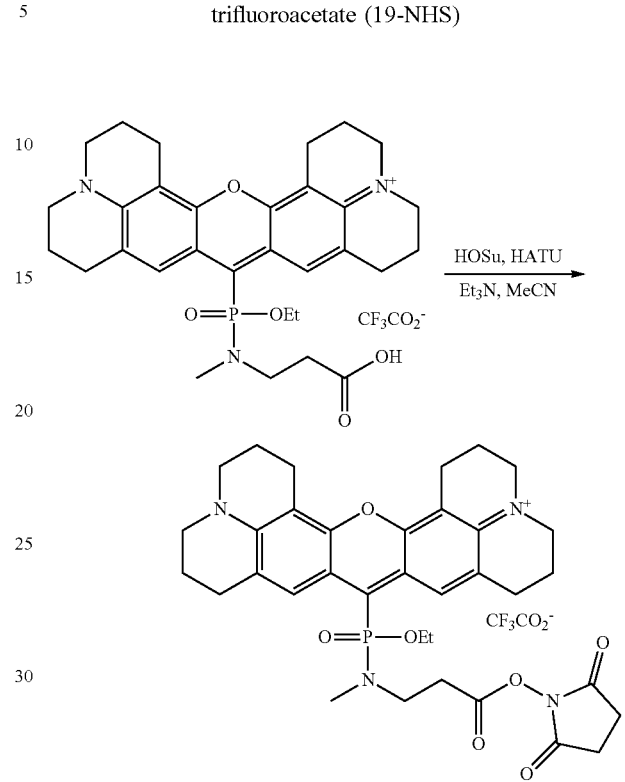

Compound 19. In a screw-cap test tube to a solution of the corresponding pyronine (100 mg; 0.26 mmol) in MeCN (2 mL) compound 10a (97 mg; 0.39 mmol) was added at r.t. under argon. The resulted mixture was stirred overnight at 60° C. After cooling down to r.t., the reaction mixture was diluted with CH$_2$Cl$_2$ (~3 mL) and subjected to column chromatography (30 g of SiO$_2$, CH$_2$Cl$_2$/MeOH 30:1) to give 50 mg (31%) of a violet oil. The product from previous step was dissolved in a mixture of CH$_2$Cl$_2$ and TFA (1:1, 2 mL), and the resulted solution was stirred for 2 h at r.t. Afterwards, all volatiles were removed in vacuo, and the residue was subjected to column chromatography (25 g of SiO$_2$, CH$_2$Cl$_2$/MeOH 10:1). The crude product was dissolved in MeCN (3 mL), the resulted solution was cooled down with an ice bath, and DDQ (18 mg; 0.079 mmol) was added. After 10 min stirring at r.t, the reaction mixture was directly subjected to column chromatography (25 g of SiO$_2$, MeCN→MeCN/H$_2$O 10:1+0.1 v/v % of TFA to yield 27 mg of crude product which was further purified by additional column chromatography (20 g of SiO$_2$, MeCN/H$_2$O 10:1+0.1 v/v % of TFA) to afford 11 mg (7% based on the starting pyronine) of a dark blue solid. $^1$H NMR (400 MHz, CDCl$_3$): δ=1.35 (t, J$_{H-H}$=7.0 Hz, 3H, OEt), 1.99-2.14 (m, 8H, 4×CH$_2$), 2.60-2.67 (m, J$_{H-H}$=6.7 Hz, 2H, CH$_2$), 2.77 (d, =10.5 Hz, 3H, NMe), 2.84-3.00 (m, 8H, 4×CH$_2$), 3.51-3.58 (m, 8H, 4×NCH$_2$), 3.58-3.66 (m, 2H, NCH$_2$), 4.09-4.35 (m, 2H, OEt), 8.33 (s, 2H$_{ar}$). $^{31}$P NMR (162 MHz, CDCl$_3$): δ=18.9 ppm. MS (ESI): m/z (positive mode, rel. int., %)=564.2 (100) [M−Cl]$^+$. HPLC: t$_R$=12.0 min (96%), B/A=30/70-100/0 in 25 min, column 4×250 mm, 1.2 mL/min, detection at 254 nm. UV/Vis (MeCN): λ$_{max}$ (ε)=648 nm (29373 M$^{-1}$cm$^{-1}$); fluorescence (MeCN): λ$_{excit}$=630 nm, λ$_{em}$=682 nm, Φ$_{fl}$=0.19. Standard: Atto 655, Φ$_{fl}$=0.30 (H$_2$O). UV/Vis (PBS 7.4): λ$_{max}$ (ε)=659 nm (37214 M$^{-1}$cm$^{-1}$); fluorescence (PBS 7.4): λ$_{excit}$=640 nm, λ$_{em}$=705 nm, Φ$_{fl}$=0.11. Standard: Atto 655, Φ$_{fl}$=0.30 (H$_2$O).

Compound 19-NHS. To a solution of compound 19 (5 mg; 0.009 mmol) in MeCN (1 mL), N-hydroxysuccinimide (15 mg; 0.133 mmol), HATU (13 mg; 0.035 mmol) and NEt$_3$ (16 mg; 0.16 mmol) were added at r.t. under Ar. After 1 h stirring, the reaction mixture was evaporated to dryness, the residue was dissolved in CH$_2$Cl$_2$ (~20 mL) and washed with water (2×20 mL). The organic solution was dried with Na$_2$SO$_4$ and evaporated. The residue was subjected to column chromatography (20 g of SiO$_2$, MeCN/H$_2$O 15:1+0.1 v/v % of TFA). Fractions containing the NHS-ester were combined and freeze-dried to give 3 mg (50%) of a dark blue solid. MS (ESI): m/z (positive mode, rel. int., %)=661.3 (100) [M−Cl]$^+$. HPLC: t$_R$=14.3 min (97%), B/A=30/70-100/0 in 25 min, column 4×250 mm, 1.2 mL/min, detection at 254 nm.

10-(Diethylamino)-7-(dimethoxyphosphoryl)-3-(dimethylamino)-6,7-dihydro-5H-benzo[c]xanthenylium trifluoroacetate (20)

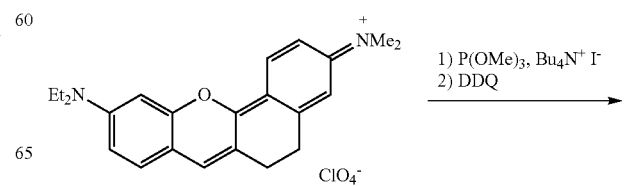

-continued

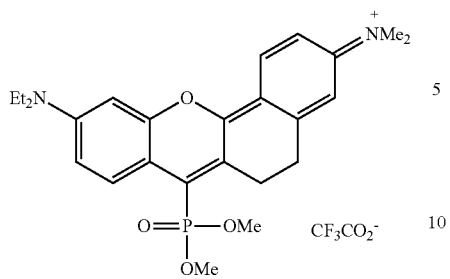

Compound 20. Trimethyl phosphite (88 μL; 0.75 mmol, 3 eq) was added to a stirred solution of the dye H-hNR [Niu, G.; Liu, W.; Zhou, B.; Xiao, H.; Zhang, H.; Wu, J.; Ge, J.; Wang, P. *J. Org. Chem.* 2016, 81(17), 7393-7399.] (112 mg; 0.25 mmol) and tetrabutylammonium iodide (92 mg; 0.25 mmol) in dry $CH_2Cl_2$ (6 mL). The reaction mixture was stirred at rt for 3 h, eventually turning light blue. The mixture was evaporated to dryness on Celite, and the leuco dye was isolated by flash column chromatography (Büchi Sepacore Silica HP 12 g, gradient 50% to 100% EtOAc/hexane) and used directly in the next step.

The material was dissolved in $CH_2Cl_2$ (5 mL), the solution was cooled in dry ice-acetone bath, and DDQ (57 mg; 0.25 mmol) in $CH_2Cl_2$ (5 mL) was added quickly dropwise. The resulting dark green solution was allowed to warm up to rt and stirred for 15 min. The mixture was evaporated to dryness Celite, and the product was isolated by flash column chromatography (Büchi Sepacore Silica HP 12 g, gradient 0% to 100% A:B, A–5% $H_2O$/MeCN+0.1% v/v TFA, B–MeCN); the fractions containing the product were pooled and evaporated. The residue was dissolved in 1,4-dioxane, filtered through a 0.2 μM PTFE membrane filter and lyophilized. Black solid, yield 130 mg (92%). $^1H$ NMR (400 MHz, DMSO-$d_6$): δ 8.57 (d, J=9.6 Hz, 1H), 8.14 (d, J=9.3 Hz, 1H), 7.22 (dd, J=9.7, 2.7 Hz, 1H), 7.16 (t, J=2.4 Hz, 1H), 6.91 (dd, J=9.3, 2.4 Hz, 1H), 6.75 (d, J=2.3 Hz, 1H), 3.82 (s, 2H), 3.79 (s, 2H), 3.61 (q, J=6.8 Hz, 4H), 3.30-3.24 (m, 2H), 3.22 (s, 7H), 2.95 (dd, J=8.5, 6.1 Hz, 2H), 1.21 (t, J=7.0 Hz, 7H). $^{31}P$ NMR (162 MHz, DMSO-$d_6$): δ 14.64. $^{19}F$ NMR (376 MHz, DMSO-$d_6$): δ −74.60. $^{13}C$ NMR (101 MHz, DMSO-$d_6$): δ 164.1 (d, J=15.3 Hz), 158.3 (q, J=35.2 Hz), 155.7, 155.5 (d, J=12.9 Hz), 152.5, 146.7, 138.4 (d, J=170.3 Hz), 130.3, 129.6, 129.5, 125.6 (d, J=10.6 Hz), 115.0, 114.8 (d, J=12.1 Hz), 113.5 (d, J=1.5 Hz), 113.0, 110.5, 96.3, 53.31, 53.26, 44.8, 40.2, 27.0, 25.1, 12.5. MS (ESI): m/z (positive mode, rel. int., %)=455.2 (100) $[M]^+$. HRMS ($C_{24}H_{35}H_3O_2PS$): m/z (positive mode)=455.2099 (found $[M]^+$), 455.2094 (calc.). UV/Vis (MeCN): $\lambda_{max}$ (ε) 681 nm (40000 $M^{-1}cm^{-1}$); fluorescence (MeCN): $\lambda_{excit}$=630 nm, $\lambda_{em}$=737 nm, $\Phi_{fl}$=0.17 (abs.). UV/Vis (PBS 7.4): $\lambda_{max}$ (ε)=693 nm (29000 $M^{-1}cm^{-1}$); fluorescence (MeCN): $\lambda_{excit}$=630 nm, $\lambda_{em}$=754 nm, $\Phi_{fl}$=0.02 (abs.).

EXAMPLE 3

Synthesis of Fluorescent Phosphorylated Thioxanthene Dyes and their Precursors 3,6-Bis(dimethylamino)-9H-thioxanthenylium perchlorate (21a)

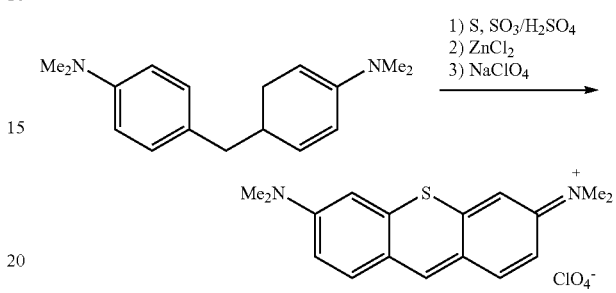

Compound 21a. Powdered sulfur (10 g) was added in portions over 15 min to 30% $SO_3$—$H_2SO_4$ (25 mL), the resulting brown yellow suspension was cooled in ice-water bath and 4,4'-bis(dimethylamino)diphenylmethane (9.5 g, 37.4 mmol) was added in portions at such a rate that the temperature of the reaction mixture remained below 20° C. (over ~10 min). The yellow suspension was stirred at rt for 1.5 h. The mixture was then poured on ice (~250 mL), the dark purple mixture was allowed to warm up to rt, transferred into a 500 mL round-bottom flask and refluxed for 1 h. The resulting suspension was cooled down to rt, filtered through a layer of Celite, a solution of $ZnCl_2$ (80 g in 150 mL water) was added and the mixture was left at 4° C. overnight. A dark red oil, containing the crystals of 3,6-bis(dimethylamino)thioxanthylium trichlorozincate [prepared according to WO 2010067078 A2 and *Heterocyclic Chemistry*, 1966, 3, p. 228], separated. The colorless supernatant was decanted off, the residue was dissolved in boiling water (150 mL) and $NaClO_4$ solution (5 g in 10 mL water) was added. The resulting suspension was allowed to cool down to rt and then left in ice-water bath to complete crystallization. The crystals were filtered off, washed with water, $Et_2O$/hexane (1:1) and $Et_2O$, dried in vacuo. Small brown crystals, yield 606 mg (4%). MS (ESI): m/z (positive mode, rel. int., %)=283.1 (100) $[M]^+$.

9-[(Diisopropylamino)(methoxy)phosphoryl]-3,6-bis(dimethylamino)-9H-thioxanthen-9-ylium trifluoroacetate (21)

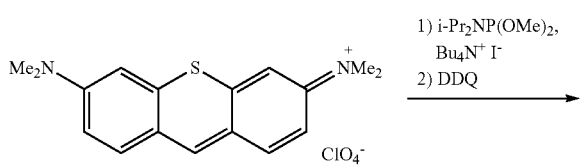

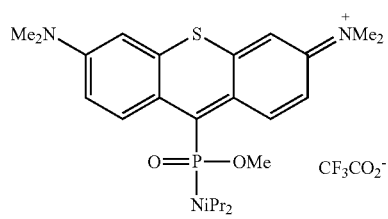

Compound 21. Dimethyl N,N-diisopropylphosphoramidite (181 µL; 0.786 mmol) was added to a stirred suspension of 21a (100 mg; 0.262 mmol) and tetrabutylammonium iodide (97 mg; 0.262 mmol) in dry $CH_2Cl_2$ (4 mL). The reaction mixture, which quickly turned into a light-brown clear solution, was stirred at rt for 30 min. The mixture was evaporated to dryness, and the leuco dye was isolated by column chromatography (18 g $SiO_2$, gradient 50% to 100% EtOAc/hexane) and used directly in the next step.

The material was dissolved in $CH_2Cl_2$ (3 mL), the solution was cooled in dry ice-acetone bath, and DDQ (59 mg; 0.26 mmol) in $CH_2Cl_2$ (3 mL) was added quickly dropwise. The resulting turquoise-blue solution was allowed to warm up to rt, stirred for 15 min. The mixture was evaporated to dryness, and the residue was subjected to column chromatography (20 g of $SiO_2$, gradient 0% to 5% $H_2O$/MeCN, then 5% $H_2O$/MeCN+0.5 v/v % TFA); the fractions containing the product were pooled and evaporated. The residue was dissolved in 1,4-dioxane (with addition of minimal amount of water to dissolve the solids), centrifuged, the supernatant was filtered through 0.2 µM PTFE membrane filter and lyophilized. Blue solid, yield 145 mg (97%). MS (ESI): m/z (positive mode, rel. int., %)=460.2 (100) [M]$^+$. HRMS ($C_{24}H_{35}N_3O_2PS$): m/z (positive mode)=460.2184 (found [M]$^+$), 460.2182 (calc.). UV/Vis (MeCN): $\lambda_{max}$ (ε)=654 nm (64000 $M^{-1}cm^{-1}$); fluorescence (MeCN): $\lambda_{excit}$=610 nm, $\lambda_{em}$=728 nm, $\Phi_{fl}$=0.10. Standard: Oxazine 1, $\Phi_{fl}$=0.11 (EtOH).

EXAMPLE 4

Synthesis of Fluorescent Phosphorylated Acridine Dyes and their Precursors 9-(Dimethoxyphosphoryl)-3,6-bis(dimethylamino)-10-methylacridinium trifluoroacetate (22)

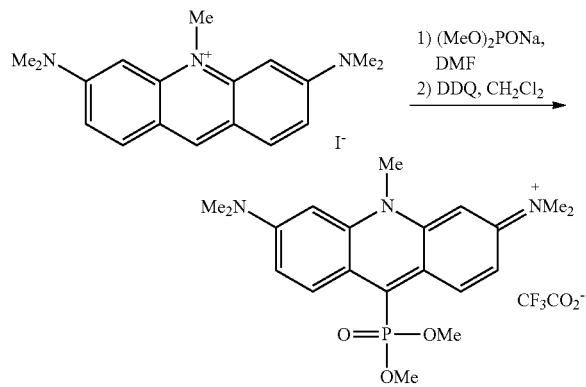

Compound 22. To a stirred suspension of NaH (33 mg of 60 wt. % in mineral oil, 0.825 mmol) in dry DMF (1 mL), cooled in ice-water bath, dimethyl phosphite (78 µL, 0.825 mmol) was added in one portion. The resulting suspension was warmed up to rt and stirred for 30 min, turning into a clear solution. A suspension of 3,6-bis(dimethylamino)-10-methylacridinium iodide [prepared according to Rodriguez, M. E.; Azizuddin, K.; Zhang, P.; Chiu, S.; Lam, M.; Kenney, M. E.; Burda, C.; Oleinick, N. L. Mitochondrion 2008, 8, 237-246] (100 mg, 0.25 mmol) in DMF (1 mL) was added, and the resulting clear orange-brown solution was stirred at rt for 1 h and at 100° C. for 1 h. The reaction mixture was evaporated to dryness (bath temperature 60° C.) and re-evaporated with acetone. The intermediate leuco dye was isolated by column chromatography (15 g of $SiO_2$, gradient 0% to 5% MeOH/EtOAc) and used directly in the next step.

The material was dissolved in $CH_2Cl_2$ (3 mL), the solution was cooled in dry ice-acetone bath, and DDQ (30 mg; 0.13 mmol) in $CH_2Cl_2$ (2 mL) was added quickly dropwise. The resulting bright red-purple mixture was allowed to warm up to rt and stirred for 15 min. The mixture was evaporated to dryness, and the residue was subjected to column chromatography (15 g of $SiO_2$, gradient 0% to 5% $H_2O$/MeCN, then 5% to 10% $H_2O$/MeCN+0.5 v/v % TFA); the fractions containing the product were pooled, evaporated and re-purified by column chromatography (18 g of $SiO_2$, 5% $H_2O$/MeCN+0.2 v/v % TFA). The residue after evaporation was dissolved in 1,4-dioxane (with addition of minimal amount of water to dissolve the solids), centrifuged, the supernatant was filtered through 0.2 µM PTFE membrane filter and lyophilized. Purple solid, yield 65 mg (52%). $^{13}$C NMR (126 MHz, $CD_3OD$): δ 156.2 (d, J=1.8 Hz), 145.0 (dd, J=14.0, 2.9 Hz), 137.3 (d, J=172.6 Hz), 132.4 (d, J=4.1 Hz), 120.2 (dd, J=11.2, 2.2 Hz), 116.5, 94.3, 68.1, 54.1 (d, J=5.9 Hz), 40.7, 38.3. MS (ESI): m/z (positive mode, rel. int., %)=388.2 (100) [M]$^+$. HRMS ($C_{20}H_{22}N_3O_3P$): m/z (positive mode)=388.1785 (found [M]$^+$), 388.1785 (calc.). UV/Vis (MeOH): $\lambda_{max}$ (ε)=560 nm (43000 $M^{-1}cm^{-1}$); fluorescence (MeOH): $\lambda_{excit}$=510 nm, $\lambda_{em}$=620 nm, $\Phi_{fl}$=0.95. Standard: Atto 495, $\Phi_{fl}$=0.5 (EtOH).

10-(4-tert-Butoxy-4-oxobutyl)-3,6-bis(dimethylamino)acridinium iodide (23a)

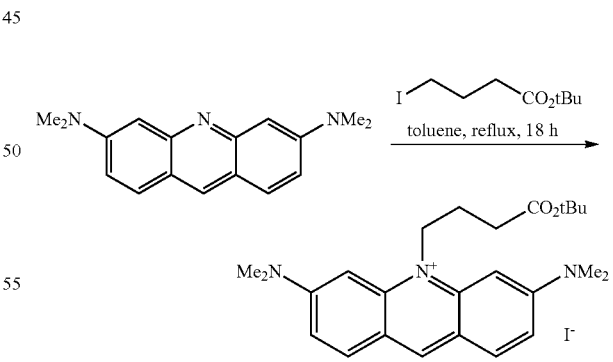

Compound 23a (Atto 495 tert-butyl ester). A suspension of Acridine Orange base (265 mg, 1 mmol) and tert-butyl 4-iodobutyrate [prepared according to Hardouin, C.; Kelso, M. J.; Romero, F. A.; Rayl, T. J.; Leung, D.; Hwang, I.; Cravatt, B. F.; Boger, D. L. J. Med. Chem. 2007, 50(14), 3359-3368] in toluene (15 mL) was refluxed for 18 h. The reaction mixture was evaporated to dryness, and the residue was subjected to column chromatography (40 g of $SiO_2$, gradient 5% to 10% EtOH/CH$_2$Cl$_2$), eluting the fluorescent band. The eluate was evaporated and the product was isolated by reversed-phase column chromatography (30 g RP-C$_{18}$, gradient 50% to 20% H$_2$O/MeCN+1 v/v % TFA), the fractions containing the product were pooled and the residue was lyophilized from H$_2$O/MeCN (2:1). Orange solid, yield 165 mg (31%). $^1$H NMR (400 MHz, CD$_3$OD): δ 8.46 (d, J=3.3 Hz, 1H), 7.76 (dd, J=9.3, 2.3 Hz, 2H), 7.15 (dt, J=9.3, 2.2 Hz, 2H), 6.79 (br.s, 2H), 4.59-4.51 (m, 2H), 3.29 (s, 12H), 2.64 (dd, J=6.9, 4.9 Hz, 2H), 2.05 (dq, J=11.8, 6.4 Hz, 2H), 1.49 (s, 9H) ppm. $^{13}$C NMR (101 MHz, CD$_3$OD): δ 174.4, 157.5, 144.1, 144.0, 134.2, 118.3, 115.4, 93.7, 82.2, 48.1, 41.0, 31.9, 28.5, 21.4 ppm. MS (ESI): m/z (positive mode, rel. int., %)=408.3 (100) [M]$^+$. HRMS (C$_{25}$H$_{34}$N$_3$O$_2$): m/z (positive mode)=408.2643 (found [M]$^+$), 408.2646 (calc.).

10-(3-Carboxypropyl)-3,6-bis(dimethylamino)-9-(hydroxyhydrophosphoryl)acridinium trifluoroacetate (23)

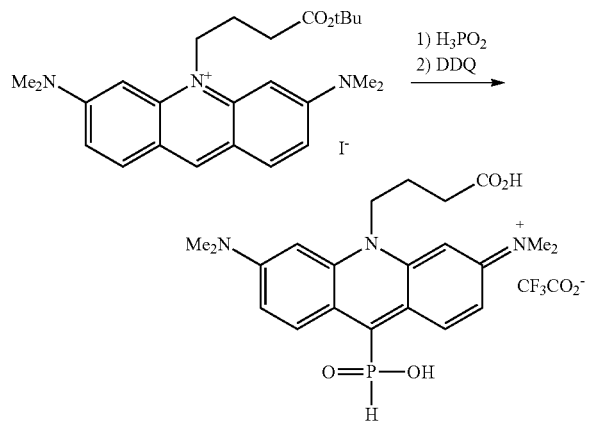

Compound 23. A suspension of 23a (165 mg, 0.31 mmol) in 50% aq. H$_3$PO$_2$ (2 mL) was stirred at 100° C. for 4 days. The resulting solution was cooled down to rt and transferred directly on top of a reversed-phase column (15 g RP-C$_{18}$), excess H$_3$PO$_2$ was washed off first with water, followed by the 50% to 30% H$_2$O/MeCN gradient. Fractions containing the leuco dye were pooled, MeCN was evaporated and the residue was lyophilized, giving 100 mg of the leuco dye as a red solid. MS (ESI): m/z (negative mode, rel. int., %)=416.2 (100) [M–H]$^-$.

The leuco acid was dissolved in the mixture of CH$_2$Cl$_2$ (3 mL) and MeOH (3 mL), the solution was cooled in dry ice-acetone bath, and DDQ (54 mg; 0.24 mmol) in CH$_2$Cl$_2$ (4 mL) was added quickly dropwise. The resulting bright-pink suspension was allowed to warm up to rt and stirred for 15 min. The mixture was evaporated to dryness, and the residue was subjected to column chromatography (30 g of SiO$_2$, gradient 20% to 50% H$_2$O/MeCN, then 50% H$_2$O/MeCN+1 v/v % TFA); the fractions containing the product were pooled and evaporated. Further purification was done by reversed-phase column chromatography (15 g RP-C$_{18}$, gradient 10% to 40% H$_2$O/MeCN+5 v/v % 0.1 M Et$_3$NH$^+$ HCO$_3^-$ in H$_2$O). The pure fractions containing the product were evaporated to dryness, the residue was dissolved in acetic acid (~50 mL), centrifuged, the supernatant was filtered through 0.2 μM PTFE membrane filter and lyophilized; the impure fractions were re-chromatographed and treated again as described, giving the combined yield of 100 mg (61% over 2 steps) as a red solid. $^1$H NMR (400 MHz, acetic acid-d$_4$): δ 9.02 (d, J=9.8 Hz, 2H), 8.57 (d, J=567.5 Hz, 1H), 7.23 (dd, J=9.5, 1.9 Hz, 2H), 6.73 (s, 2H), 4.72-4.54 (m, 2H), 3.30 (s, 12H), 2.80 (t, J=6.1 Hz, 2H), 2.27 (td, J=11.9, 5.6 Hz, 1H). $^{31}$P NMR (162 MHz, acetic acid-d$_4$): δ 5.81. $^{19}$F NMR (376 MHz, acetic acid-d$_4$): δ –76.67. MS (ESI): m/z (positive mode, rel. int., %)=416.2 (100) [M]$^+$, 438.2 (48) [MH+Na]$^+$, 454.1 (34) [M–H+K]$^+$. HRMS (C$_{21}$H$_{27}$N$_3$O$_4$P): m/z (positive mode)=416.1732 (found [M]$^+$), 416.1734 (calc.). UV/Vis (MeOH): λ$_{max}$ (ε)=527 nm (67000 M$^{-1}$cm$^{-1}$); fluorescence (MeOH): λ$_{excit}$=490 nm, λ$_{em}$=579 nm, Φ$_{fl}$=0.75. Standard: Atto 495, Φ$_{fl}$=0.5 (EtOH). UV/Vis (PBS 7.4): λ$_{max}$ (ε)=535 nm (38000 M$^{-1}$cm$^{-1}$); fluorescence (PBS 7.4): λ$_{excit}$=490 nm, λ$_{em}$=595 nm, Φ$_{fl}$=0.14. Standard: Rhodamine 6G, Φ$_{fl}$=0.95 (EtOH).

[10-(3-Carboxypropyl)-3,6-bis(dimethylamino)acridinium-9-yl]phosphinate NHS ester (23-NHS)

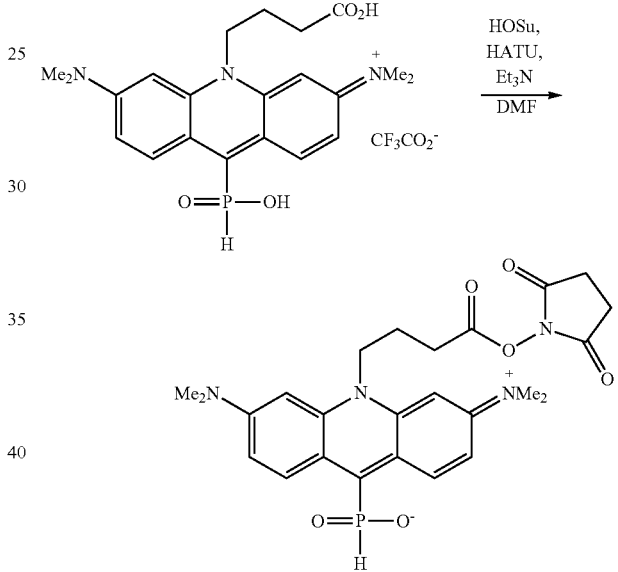

Compound 23-NHS. Triethylamine (20 μL, ~140 μmol) N-hydroxysuccinimide (50 μL of a 1.13 M solution in DMF, 56.5 μmol) and HATU (50 μL of a 0.76 M solution in DMF, 38 μmol) were added to a suspension of 23 (2 mg, 3.8 μmol) in DMF (0.1 mL). The resulting clear bright-pink solution was stirred at rt for 1 h. The solvent was evaporated to dryness at rt, and the product was isolated from the residue by column chromatography (15 g of SiO$_2$, gradient 10% to 25% H$_2$O/MeCN in 5% increments). The fractions containing the product were pooled, evaporated at rt, the residue was dissolved in dioxane (with minimal amount of water added to dissolve the solids), centrifuged off the silica dust, filtered the supernatant through 0.2 μM PTFE membrane filter and lyophilized the filtrate. Yield 1.2 mg (62%), purity 87% (HPLC), red solid. MS (ESI): m/z (positive mode, rel. int., %)=513.2 (100) [M+H]$^+$, 535.2 (51) [M+Na]$^+$. HPLC: t$_R$=9.0 min (87%), B/A=30/70-100/0 in 25 min, column 4×250 mm, flow 1.2 mL/min, detection at 254 nm.

EXAMPLE 5

Synthesis of Fluorescent Phosphorylated Carbopyronine Dyes and their Precursors 9-(Diisopropoxyphosphoryl)-3,6-bis(dimethyl-amino)-10,10-dimethyl-9,10-dihydro-anthracenylium trifluoromethanesulfonate (24)

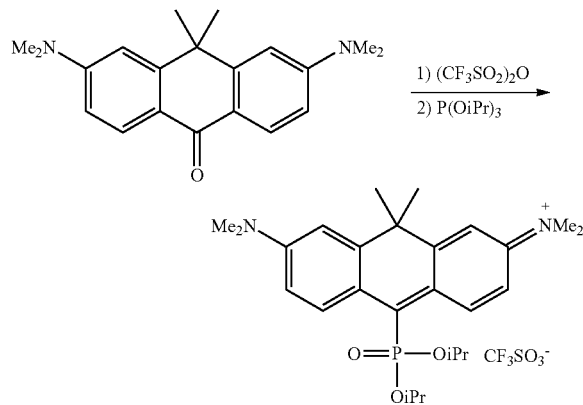

Compound 24. In a Schlenk flask to a solution of 3,6-bis(dimethylamino)-10,10-dimethylanthrone [prepared according to WO 2012052435 A1] (20 mg; 0.065 mmol) in CH$_2$Cl$_2$ (1 ml) triflic anhydride (18 mg; 0.065 mmol) was injected under argon. The resulted blue colored reaction mixture stirred for 10 min at r.t., and P(OiPr)$_3$ (13 mg; 0.065 mmol) was injected thereto. After overnight stirring at r.t., all volatiles were evaporated in the flow of argon. The residue was subjected to reverse-phase chromatography (30 g of RP—SiO$_2$, MeCN/H$_2$O 1:1+0.1 v/v % of TFA). Green-colored fractions were collected, combined and evaporated. After additional normal phase column chromatography (30 g of SiO$_2$, CH$_2$Cl$_2$/MeOH 20:1→10:1) 10 mg (25%) of a dark green solid were obtained. $^1$H NMR (400 MHz, CD$_3$CN): δ=1.18 (d, $J_{H-H}$=6.2 Hz, 6H, OiPr), 1.41 (d, $J_{H-H}$=6.2 Hz, 6H, OiPr), 1.66 (s, 6H, 2×Me), 3.35 (s, 2×NMe$_2$), 4.92 (m, 2H, 2×OiPr), 6.92 (dd, $J_{H-H}$=9.8 and 2.7 Hz, 2H$_{ar}$), 7.13 (m, $J_{H-H}$=2.7 Hz), 8.80 (d, $J_{H-H}$=9.8 Hz) ppm. MS (ESI): m/z (positive mode, rel. int., %)=457.3 (100) [M—OTf]$^+$. UV/Vis (MeCN): λ$_{max}$ (ε)=694 nm (37946 M$^{-1}$cm$^{-1}$); fluorescence (MeCN): λ$_{excit}$=660 nm, λ$_{em}$=779 nm, Φ$_{fl}$=0.03. Standard: Rhodamine 800, Φ$_{fl}$=0.25 (EtOH).

9-[(Allyloxy)(diisopropylamino)phosphoryl]-3,6-bis(dimethylamino)-10,10-dimethyl-9,10-dihydroanthracenylium trifluoromethanesulfonate (25)

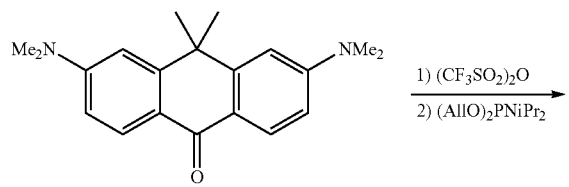

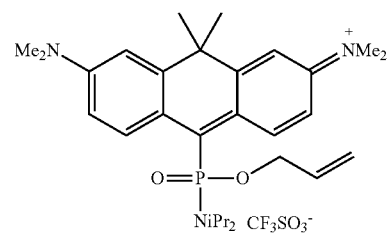

Compound 25. In a Schlenk flask to a solution of 3,6-bis(dimethylamino)-10,10-dimethylanthrone (50 mg; 0.16 mmol) in CH$_2$Cl$_2$ (2 mL) triflic anhydride (46 mg; 0.16 mmol) was injected under argon. The resulted blue colored reaction mixture stirred for 10 min at r.t., and diallyl N,N-diisopropylphosphoramidite (40 mg; 0.16 mmol) was injected thereto. After overnight stirring at r.t., the reaction mixture was diluted with MeCN (~5 mL) and directly subjected to column chromatography (30 g of SiO$_2$, MeCN→MeCN/H$_2$O 20:1→10:1→5:1→2:1). Green-colored fractions were collected, combined and evaporated. After additional reverse-phase column chromatography (20 g of RP—SiO$_2$, MeCN/H$_2$O 1:1→5:1+0.1 v/v % of TFA) 18 mg (21%) of a dark green solid were obtained. $^1$H NMR (400 MHz, CDCl$_3$): δ=1.28 (d, $J_{H-H}$=6.7 Hz, 6H, NiPr), 1.33 (d, $J_{H-H}$=6.8 Hz, 6H, NiPr), 1.69 (s, 6H, 2×Me), 3.35 (s, 12H, 2×NMe$_2$), 3.47-3.58 (m, 2H, NiPr$_2$), 4.27-4.37 (m, 1H, OAll), 4.52-4.61 (m, 1H, OAll), 5.09-5.14 (m, $J_{H-H}$=10.3 and 1.1 Hz, 1H, OAll), 5.19-5.26 (m, $J_{H-H}$=17.1 and 1.5 Hz, 1H, OAll), 5.75-5.86 (m, 1H, OAll), 6.75 (t, $J_{H-H}$=9.8 Hz, $J_{H-P}$=2.5 Hz, 2H$_{ar}$), 7.11 (t, $J_{H-H}$=2.5 Hz, $J_{H-P}$=2.5 Hz, 2H$_{ar}$), 8.84 (d, $J_{H-H}$=9.8 Hz, 2H$_{ar}$) ppm. $^{13}$C NMR (100 MHz, CDCl$_3$, APT): δ=14.0 (+), 22.6 (+, d, $J_{C-P}$=3.1 Hz), 22.8 (+, d, $J_{C-P}$=2.7 Hz), 41.4 (+), 47.3 (+, d, $J_{C-P}$=6.0 Hz), 66.8 (−, d, $J_{C-P}$=5.3 Hz), 111.2 (+), 112.3 (+), 118.6 (−), 124.0 (−, d, $J_{C-P}$=8.5 Hz), 129.0 (+), 132.6 (+, d, $J_{C-P}$=6.7 Hz), 138.6 (d, +, $J_{C-P}$=4.2 Hz), 155.4 (−), 156.7 (−, d, $J_{C-P}$=12.1 Hz) ppm. $^{31}$P NMR (162 MHz, CDCl$_3$): δ=22.3 ppm. MS (ESI): m/z (positive mode, rel. int., %)=496.4 (100) [M—OTf]$^+$. HPLC: t$_R$=15.7 min (96%), B/A=30/70-100/0 in 25 min, column 4×250 mm, 1.2 mL/min, detection at 635 nm. UV/Vis (MeCN): λ$_{max}$ (ε)=698 nm (40789 M$^{-1}$cm$^{-1}$); fluorescence (MeCN): λ$_{excit}$=700 nm, λ$_{em}$=775 nm, Φ$_{fl}$=0.26. Standard: Rhodamine 800, CD$_{fl}$=0.25 (EtOH).

6-[(Allyloxy)(diisopropylamino)phosphoryl]-1,11-bis(2-methoxyethyl)-13,13-dimethyl-1,2,3,4,6,8,9,10,11,13-decahydrobenzo[1,2-g:5,4-g']diquinolin-6-ylium trifluoroacetate (26)

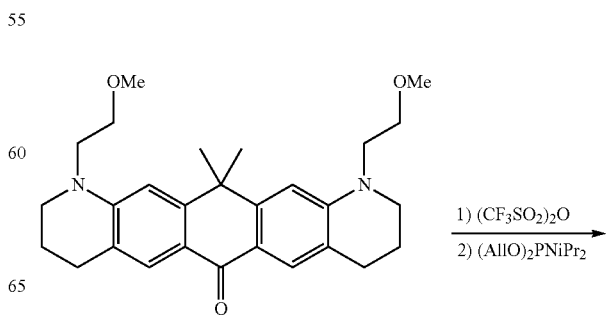

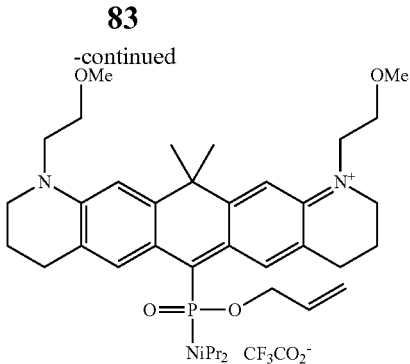

Compound 26. Prepared similarly to compound 25 from the corresponding ketone. The product was isolated by column chromatography (30 g of SiO$_2$, MeCN→MeCN/H$_2$O 20:1→→5:1→2:1). Green-colored fractions were collected, combined and evaporated. After additional reverse-phase column chromatography (20 g of RP—SiO$_2$, MeCN/H$_2$O 1:1→5:1, then 1:10→1:5→1:1+0.1 v/v % of TFA) 4 mg (5%) of green powder was obtained. HPLC: t$_R$=19.8 min (93%), B/A=30/70-100/0 in 25 min, column 4×250 mm, 1.2 mL/min, detection at 254 nm.

EXAMPLE 6

Synthesis of Fluorescent Phosphorylated Si-pyronine Dyes and their Precursors

Methyl P-[3,7-bis(dimethylamino)-5,5-dimethyl-5,10-dihydrodibenzo[b,e]silin-10-yl]-N,N-diisopropyl-phosphonamidate (27)

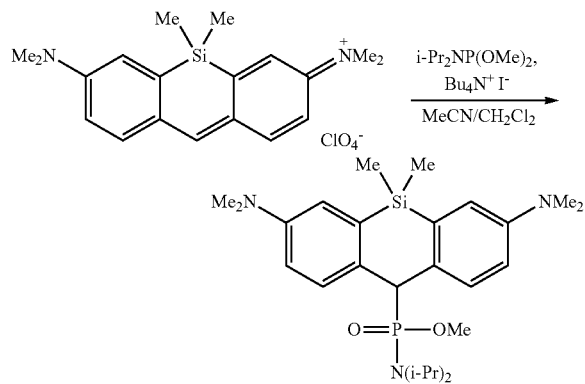

Compound 27. Dimethyl N,N-diisopropylphosphoramidite (84 μL, 0.366 mmol) was added to a solution of 3,7-bis(dimethylamino)-5,5-dimethyl-5,10-dihydrodibenzo[b,e]silinylium perchlorate [Koide, Y.; Urano, Y.; Hanaoka, K.; Terai, T.; Nagano, T. *ACS Chem. Biol.* 2011, 6(14), 600-608] (50 mg, 0.122 mmol) and tetrabutylammonium iodide (45 mg, 0.122 mmol) in MeCN (2 mL) and CH$_2$Cl$_2$ (2 mL), and the resulting mixture was stirred at rt for 20 min. The clear colorless solution was evaporated to dryness and the product was isolated by column chromatography (25 g of SiO$_2$, gradient 33% to 50% EtOAc/hexane). The fraction containing the product was pooled, evaporated and dried in vacuo to yield 55 mg (92%) of the leuco dye as a viscous colorless oil. $^1$H NMR (400 MHz, CD$_3$CN): δ 7.18 (ddd, J=8.6, 3.7, 2.5 Hz, 2H), 6.97 (dd, J=16.1, 2.9 Hz, 2H), 6.73 (dddd, J=11.4, 8.5, 3.0, 0.9 Hz, 2H), 4.49 (d, J=24.2 Hz, 1H), 3.41 (dp, J=17.6, 6.7 Hz, 2H), 3.16 (d, J=10.6 Hz, 3H), 2.92 (s, 6H), 2.90 (s, 6H), 1.17 (d, J=6.6 Hz, 6H), 0.93 (d, J=6.7 Hz, 6H), 0.61 (s, 3H), 0.37 (s, 3H) ppm. $^{13}$C NMR (101 MHz, CD$_3$CN): δ 150.1 (d, J=3.0 Hz), 149.8 (d, J=2.9 Hz), 138.3 (d, J=4.8 Hz), 137.8 (d, J=4.6 Hz), 132.5 (d, J=8.5 Hz), 132.1 (d, J=5.4 Hz), 131.5 (d, J=6.9 Hz), 118.7 (d, J=3.4 Hz), 118.1 (d, J=3.2 Hz), 114.3 (d, J=3.0 Hz), 113.8 (d, J=3.3 Hz), 52.1 (d, J=120.9 Hz), 51.2 (d, J=7.6 Hz), 46.7 (d, J=3.6 Hz), 41.0 (d, J=1.1 Hz), 24.2, 22.6 (d, J=2.3 Hz), 0.2 (d, J=1.0 Hz), −0.1 (d, J=4.2 Hz) ppm. $^{31}$P NMR (162 MHz, CD$_3$CN): δ 31.20 ppm. MS (ESI): m/z (positive mode, rel. int., %)=488.3 (100) [M+H]$^+$. HRMS (C$_{26}$H$_{42}$N$_3$O$_2$PSi): m/z (positive mode)=488.2860 (found [M+H]$^+$), 488.2857 (calc.).

Oxidation of the leuco dye (DDQ in CH$_2$Cl$_2$) as follows led to formation of an unstable silaxanthylium dye 27 (easily hydrolyzes to the starting 3,7-bis(dimethylamino)-5,5-dimethyl-5,10-dihydrodibenzo[b,e]silinylium). 22 mg (0.045 mmol) of the leuco dye was dissolved in CH$_2$Cl$_2$ (2 mL), and the solution was cooled to −78° C. A solution of DDQ (10 mg, 0.044 mmol) in CH$_2$Cl$_2$ (1 mL) was then added. The reaction mixture was allowed to warm up to rt and directly subjected to column chromatography (30 g of SiO$_2$, MeCN→MeCN+0.1% v/v TFA→MeCN/H$_2$O 40:1+0.1 v/v % of TFA), the green-colored fractions were pooled and evaporated. The residue was redissolved in cold water and freeze-dried to give 50 mg of the material.

EXAMPLE 7

Synthesis of Fluorescent Phosphorylated Benzanthrylium Dyes and their Precursors 1-Bromo-5-(Dimethylamino)Naphthalene (28a)

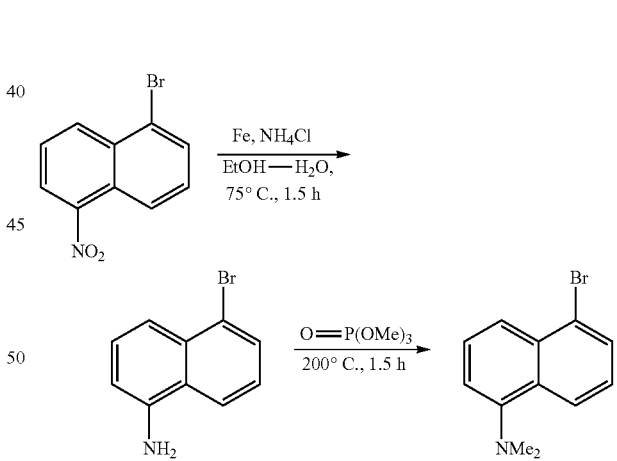

Compound 28a. To a suspension of 1-bromo-5-nitronaphthalene (2 g, 7.94 mmol) in EtOH (50 mL), a solution of NH$_4$Cl (2.2 g, 41.1 mmol) in water (20 mL) was added, followed by iron powder (1.33 g, 23.82 mmol). The resulting mixture was stirred at 75° C. (bath temperature) for 1.5 h. Celite (3 g) was added, and the mixture was allowed to cool down to rt, diluted with CH$_2$Cl$_2$ (100 mL), filtered through a plug of Celite, washing with CH$_2$Cl$_2$ (150 mL). The filtrate was washed with brine and dried over Na$_2$SO$_4$. Upon evaporation of the filtrate, the crude material was redissolved in CH$_2$Cl$_2$ (20 mL), transferred on top of a 80 g SiO$_2$ column, and ran with 20% to 80% EtOAc/hexane gradient.

The fractions containing the product were evaporated to viscous light brown oil that quickly crystallized. Yield of 5-bromo-1-aminonaphthalene [West, R. W. *J. Chem. Soc.* 1925, 127, 494] 1.48 g (84%).

5-Bromo-1-aminonaphthalene (1.37 g, 6.17 mmol) was dissolved in trimethyl phosphate (760 μL, 6.5 mmol) in a 50 mL round-bottom flask, equipped with an air condenser and a CaCl$_2$ drying tube, the apparatus was flushed with nitrogen, and the mixture was heated at 200° C. (bath temperature) for 1.5 h. The flask was then allowed to cool below 100° C., 1 N NaOH (20 mL) was added, the resulting suspension was sonicated briefly and stirred at rt overnight. The mixture was diluted with brine, extracted with CH$_2$Cl$_2$ (3×50 mL), the combined extracts were dried over Na$_2$SO$_4$. The product was isolated by column chromatography (100 g of SiO$_2$, gradient 10% to 50% CH$_2$Cl$_2$/hexane) to yield 1-bromo-5-(dimethylamino)naphthalene 28a [West, R. W. *J. Chem. Soc.* 1925, 127, 494] as a light-orange viscous oil (1.29 g, 84%). $^1$H NMR (301 MHz, CDCl$_3$): δ 8.26 (dt, J=8.6, 1.0 Hz, 1H), 7.95 (dt, J=8.6, 0.9 Hz, 1H), 7.78 (dt, J=7.4, 1.0 Hz, 1H), 7.51 (ddd, J=8.5, 7.5, 0.7 Hz, 1H), 7.32 (ddd, J=8.4, 7.3, 0.7 Hz, 1H), 7.14 (dd, J=7.6, 1.0 Hz, 1H), 2.90 (s, 6H) ppm. $^{13}$C NMR (76 MHz, CDCl$_3$): δ 151.3, 133.4, 130.4, 130.1, 127.3, 125.4, 124.3, 123.3, 122.0, 115.0, 45.5.

4-(Dimethylamino)-2-(4,4,5,5-tetramethyl-1,3,2-dioxaborolan-2-yl)benzaldehyde (28b)

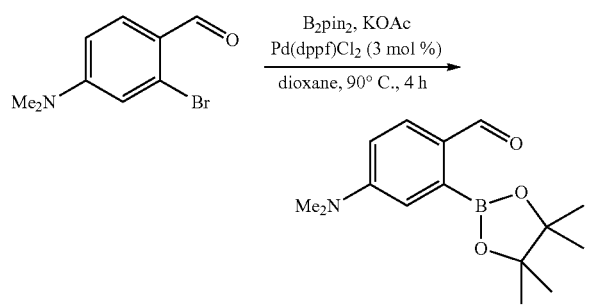

Compound 28b. 1,4-Dioxane (25 mL) was added to the solid 2-bromo-4-(dimethylamino)benzaldehyde [Meyer, W. E.; Tomcufcik, A. S.; Chan, P. S.; Emma, J. E. *J. Med. Chem.* 1984, 27, 1705-1710] (684 mg, 3 mmol), bis(pinacolato)diboron (840 mg, 3.3 mmol), KOAc (880 mg, 9 mmol) and Pd(dppf)Cl$_2$ (66 mg, 0.09 mmol), the mixture was deoxygenated on a Schlenk line and stirred under N$_2$ at 90° C. (bath temperature) for 4 h. Upon cooling to rt, the reaction mixture was filtered through a 1.5 cm pad of Celite, washing with EtOAc (100 mL). The filtrate was evaporated; the residue was dissolved in CH$_2$Cl$_2$, transferred on top of a 30 g SiO$_2$ column and ran with 10% to 50% EtOAc/hexane gradient. The fractions containing the product were evaporated, and the residue was recrystallized from CH$_2$Cl$_2$-hexane (with cooling in −78° C. bath) to give 536 mg (65%) of 28b as light-orange crystals. $^1$H NMR (500 MHz, CDCl$_3$): δ 10.20 (s, 1H), 7.84 (d, J=8.8 Hz, 1H), 7.01 (d, J=2.7 Hz, 1H), 6.77 (dd, J=8.8, 2.7 Hz, 1H), 3.08 (s, 6H), 1.39 (s, 12H). $^{13}$C NMR (126 MHz, CDCl$_3$): δ 192.22, 192.20, 152.9, 130.8, 130.1, 117.3, 112.9, 84.3, 40.4, 25.1. MS (ESI): m/z (positive mode, rel. int., %)=244.1 (100), 298.2 (3) [M+Na]$^+$. HRMS (C$_{15}$H$_{22}$NO$_3$B): m/z (positive mode)=298.1578 (found [M+Na]$^+$), 298.1588 (calc.).

4-(Dimethylamino)-2-[5-(dimethylamino)naphthalen-1-yl]benzaldehyde (28c)

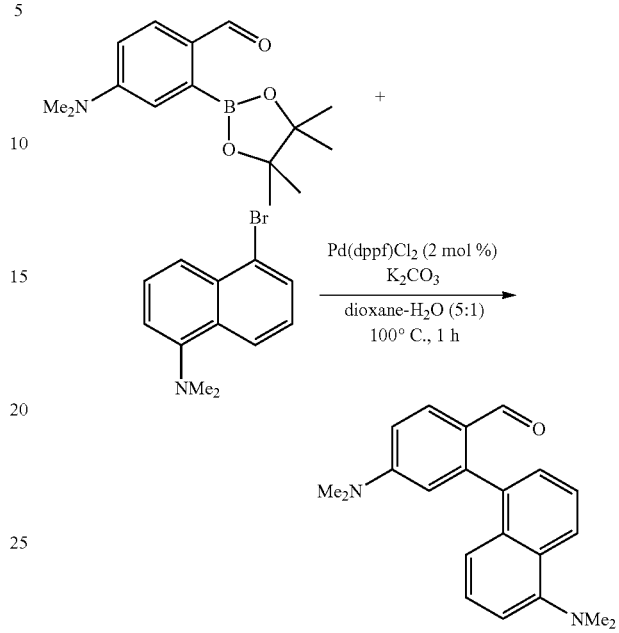

Compound 28c. 1,4-Dioxane (15 mL) and water (3 mL) were added to a mixture of 28a (414 mg, 1.65 mmol), 28b (500 mg, 1.82 mmol), K$_2$CO$_3$ (455 mg, 3.3 mmol) and Pd(dppf)Cl$_2$ (24 mg, 0.033 mmol), the mixture was deoxygenated on a Schlenk line and stirred under N$_2$ at 100° C. (bath temperature) for 1 h. Upon cooling down to rt, the mixture was diluted with sat. aq. NaHCO$_3$ (50 mL), extracted with EtOAc (3×40 mL), washed with brine and dried over Na$_2$SO$_4$. The product was isolated by column chromatography (40 g of SiO$_2$, gradient 10% to 30% EtOAc/hexane) and dried in vacuo to yield 28c (524 mg, 99%) as a yellowish foam. $^1$H NMR (400 MHz, CDCl$_3$): δ 9.39 (s, 1H), 8.38 (d, J=8.5 Hz, 1H), 8.06 (d, J=8.9 Hz, 1H), 7.56 (dd, J=8.6, 6.9 Hz, 1H), 7.45 (d, J=6.9 Hz, 1H), 7.37-7.25 (m, 2H), 7.11 (dd, J=6.7, 1.8 Hz, 1H), 6.83 (dd, J=8.9, 2.7 Hz, 1H), 6.61 (d, J=2.7 Hz, 1H), 3.09 (s, 6H), 2.96 (s, 6H). $^{13}$C NMR (101 MHz, CDCl$_3$): δ 190.4, 153.5, 151.0, 147.2, 137.2, 134.2, 129.0, 128.8, 127.5, 126.3, 124.4, 124.2, 124.1, 121.2, 114.2, 113.1, 111.0, 45.4, 40.1. MS (ESI): m/z (positive mode, rel. int., %)=319.2 (100) [M+H]$^+$, 341.2 (29) [M+Na]$^+$. HRMS (C$_{21}$H$_{22}$N$_2$O): m/z (positive mode)= 319.1810 (found [M+H]$^+$), 319.1805 (calc.).

4,10-Bis(dimethylamino)-7H-benzo[de]anthracenylium perchlorate (28d)

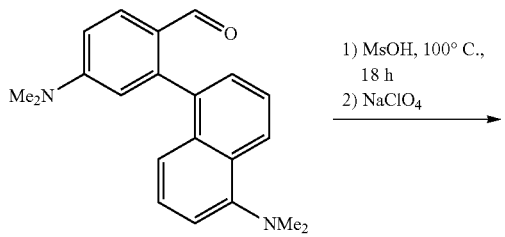

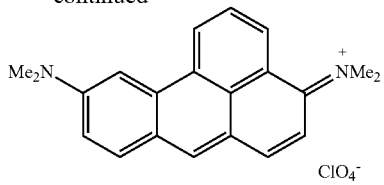

Compound 28d. A solution of 28c (440 mg, 1.38 mmol) in methanesulfonic acid (1 mL) was heated at 100° C. (bath temperature) overnight. The viscous mixture was diluted with methanesulfonic acid (2 mL) and poured into 150 mL of ice-water mixture, containing 5 g $NaClO_4$. The resulting blue suspension was stirred until all ice melted; the dark solid was filtered off, washed with water and dried on filter. The crude solid was recrystallized from $MeOH/CH_2Cl_2$, adding hexane to complete precipitation, filtered off, washed with hexane and dried in vacuo. Small black crystals, yield 520 mg (94%). $^1$H NMR (400 MHz, DMSO-$d_6$): δ 9.28 (d, J=8.0 Hz, 1H), 8.68 (d, J=8.0 Hz, 1H), 8.42 (s, 1H), 8.11 (d, J=9.5 Hz, 1H), 7.94 (t, J=8.1 Hz, 1H), 7.92 (d, J=9.1 Hz, 1H), 7.81 (d, J=2.4 Hz, 1H), 7.38 (d, J=9.5 Hz, 1H), 7.26 (dd, J=9.1, 2.4 Hz, 1H), 3.73 (s, 6H), 3.27 (s, 6H). $^{13}$C NMR (101 MHz, DMSO-$d_6$): δ 163.2, 153.0, 142.9, 141.6, 135.8, 133.7, 133.2, 131.2, 128.3, 126.2, 125.9, 122.3, 121.9, 120.4, 116.2, 115.5, 103.3, 46.3, 40.2. MS (ESI): m/z (positive mode, rel. int., %)=288.2 (100) [M−$CH_3$]$^+$, 301.2 (1) [M]$^+$. HRMS ($C_{21}H_{21}N_2$): m/z (positive mode)= 301.1690 (found [M]$^+$), 301.1699 (calc.). UV/Vis (MeOH): $\lambda_{max}$ (E) =646 nm (23000 $M^{-1}cm^{-1}$); fluorescence (MeOH): $\lambda_{excit}$=550 nm, $\lambda_{em}$=673 nm, $\Phi_{fl}$=0.25. Standard: Atto 594, $\Phi_{fl}$=0.85 ($H_2O$).

7-[(Diisopropylamino)(methoxy)phosphoryl]-4,10-bis(dimethylamino)-7H-benzo[de]anthracen-7-ylium trifluoroacetate (28)

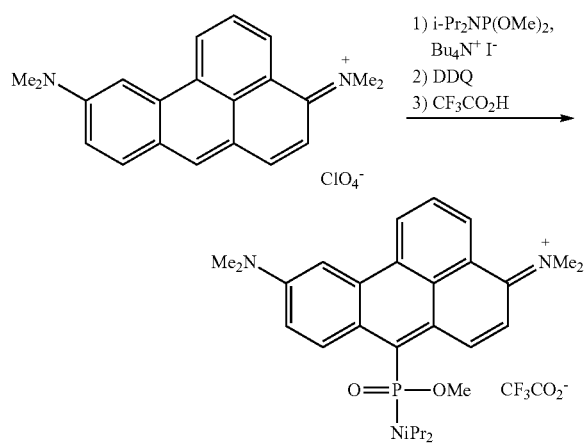

Compound 28. Dimethyl N,N-diisopropylphosphoramidite (172 μL; 0.75 mmol) was added to a stirred solution of 28d (100 mg; 0.25 mmol) and tetrabutylammonium iodide (92 mg; 0.25 mmol) in dry $CH_2Cl_2$ (5 mL). The vial was flushed with argon and the blue suspension was stirred at RT for 30 min, turning into a clear brown solution. The mixture was evaporated to dryness, and the intermediate 7H-benz[de]anthracene adduct was isolated by column chromatography (25 g of $SiO_2$, gradient 50% to 100% $EtOAc_2$/hexane). The compound was used immediately in the next step.

The material was dissolved in $CH_2Cl_2$ (10 mL), the solution was cooled in dry ice-acetone bath, and DDQ (57 mg; 0.105 mmol) in $CH_2Cl_2$ (3 mL) was added quickly dropwise. The resulting blue-green solution was allowed to warm up to RT, stirred for 15 min, followed by addition of trifluoroacetic acid (100 μL). The mixture was evaporated to dryness, and the residue was subjected to column chromatography (35 g of $SiO_2$, gradient 0% to 50% $H_2O$/MeCN); the fractions containing the product were pooled, trifluoroacetic acid (200 μL) was added, MeCN was evaporated (bath temperature ≤25° C.) and the aqueous solution was freeze-dried. The residue was dissolved in 1,4-dioxane (with addition of minimal amount of water to dissolve the solids), filtered through 0.2 μM PTFE membrane filter and re-lyophilized. Blue solid, yield 88 mg (61%). $^1$H NMR (400 MHz, $CD_3OD$): δ 9.49 (d, J=10.3 Hz, 1H), 9.35 (d, J=8.2 Hz, 1H), 9.19 (d, J=9.8 Hz, 1H), 8.73 (d, J=7.9 Hz, 1H), 8.06 (t, J=8.0 Hz, 1H), 8.01 (t, J=2.0 Hz, 1H), 7.58 (d, J=10.3 Hz, 1H), 7.41 (dd, J=9.8, 2.7 Hz, 1H), 4.99 (d, J=1.7 Hz, 6H), 3.85 (s, 6H), 3.68 (d, J=11.5 Hz, 2H), 3.34 (s, 3H), 1.35 (dd, J=6.8, 3.2 Hz, 12H) ppm. $^{19}$F NMR (376 MHz, $CD_3OD$): δ −77.29 ppm. $^{13}$C NMR (101 MHz, $CD_3OD$): δ 165.9, 153.6, 143.1 (d, J=4.9 Hz), 138.9 (d, J=152.9 Hz), 137.8 (d, J=11.5 Hz), 135.3, 133.4 (d, J=4.2 Hz), 132.5, 131.4 (d, J=2.4 Hz), 128.3, 127.9 (d, J=13.7 Hz), 126.3 (d, J=9.4 Hz), 125.3 (d, J=9.1 Hz), 124.0 (d, J=1.2 Hz), 104.4 (d, J=1.2 Hz), 52.9 (d, J=5.9 Hz), 48.7 (d, J=5.8 Hz), 46.7, 40.5, 23.2 (d, J=2.8 Hz), 22.8 (d, J=2.8 Hz) ppm. $^{31}$P NMR (162 MHz, $CD_3OD$): δ 25.95 ppm. MS (ESI): m/z (positive mode, rel. int., %)=478.3 (100) [M]$^+$. HRMS ($C_{28}H_{32}N_3O_2P$): m/z (positive mode)=478.2621 (found [M]$^+$), 478.2618 (calc.). UV/Vis (PBS 7.4): $\lambda_{max}$ (ε)=644 nm (7600 $M^{-1}cm^{-1}$); fluorescence (PBS 7.4): $\lambda_{excit}$=580 nm, $\lambda_{em}$=782 nm, $CD_{fl}$=0.04. Standard: Atto 594, $\Phi_{fl}$=0.85 ($H_2O$).

EXAMPLE 8

Synthesis of Phosphorylated BODIPY Dyes and their Precursors 10-(Diisopropoxyphosphoryl)-5,5-difluoro-1,3,7,9-tetramethyl-5H-dipyrrolo[1,2-c:2',1'-f][1,3,2]diazaborinin-4-ium-5-uide (29)

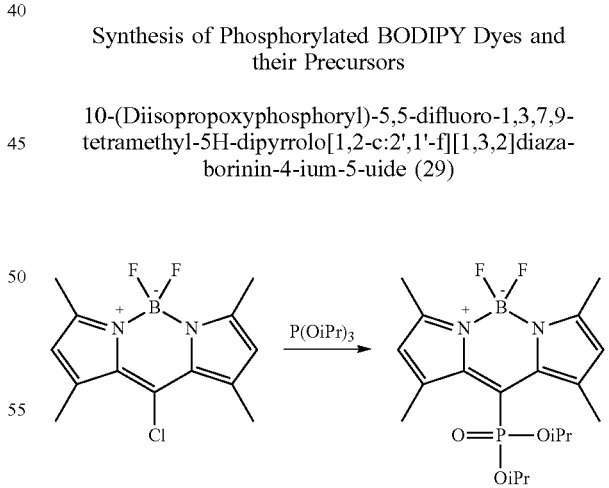

Compound 29. A solution of 10-chloro-5,5-difluoro-1,3,7,9-tetramethyl-5H-dipyrrolo[1,2-c:2',1'-f][1,3,2]diazaborinin-4-ium-5-uide [Leen, V.; Yuan, P.; Wang, L.; Boens, N.; Dehaen, W. Org. Lett. 2012, 14(24), 6150-6153] (20 mg; 0.07 mmol) in triisopropyl phosphite (0.5 mL) was stirred under argon at 100° C. for 30 min. After cooling down to room temperature, the reaction mixture was diluted with n-hexane (~5 mL) and subjected to column chromatography (30 g of SiO$_2$, hexane/EtOAc 1:1) to yield 28 mg (96%) of a violet solid. $^1$H NMR (400 MHz, CDCl$_3$): δ 6.10 (s, 2H$_{Ar}$), 4.84 (d.hept, 2H, J$_{H-P}$=7.7 Hz, J$_{H-H}$=6.2 Hz, 2CH$_{ipr}$), 2.51 (s, 6H, 2Me$_{Ar}$), 2.46 (s, 6H, 2Me$_{Ar}$), 1.40 (d, J$_{H-H}$=6.2 Hz, 6H, 2Me$_{ipr}$), 1.28 (d, J$_{H-H}$=6.2 Hz, 6H, 2Me$_{ipr}$). $^{13}$C NMR (101 MHz, CDCl$_3$): δ 157.6, 144.5, 137.10 (d, $^2$J$_{C-P}$=13.9 Hz), 129.62 (d, $^1$J$_{C-P}$=182.3 Hz), 123.5 (d, $^4$J$_{C-P}$=2.4 Hz), 72.8 (d, $^2$J$_{C-P}$=6.7 Hz), 24.0 (d, $^3$J$_{C-P}$=4.4 Hz), 23.6 (d, $^3$J$_{C-P}$=5.0 Hz), 16.6. $^{19}$F NMR (376 MHz, CDCl$_3$): δ=−146.59 (app.q 1:1:1:1, J$_{F-11B}$=32.2 Hz) ppm. $^{31}$P NMR (162 MHz, CDCl$_3$): δ=9.8 ppm. MS (ESI): m/z (positive mode, rel. int., %)=413.1 (100) [M+H]$^+$, 435.1 (93) [M+Na]$^+$.

EXAMPLE 9

Characterisation of Exemplary Compounds of the Present Invention

General Materials and Methods
Thin Layer Chromatography

Normal phase TLC was performed on silica gel 60 F$_{254}$ (Merck Millipore, Germany). For TLC on reversed phase silica gel 60 RP-18 F$_{254}$S (Merck Millipore) was used. Preparative TLC was performed on HPTLC Silica gel 60 F$_{254}$ with concentrating zone 10×2.5 cm (Merck Millipore). Compounds were detected by exposing TLC plates to UV-light (254 or 366 nm) or heating with vanillin stain (6 g vanillin and 1.5 mL conc. H$_2$SO$_4$ in 100 mL ethanol); leuco dyes were detected by staining with 1% DDQ in CH$_2$Cl$_2$.
Column Chromatography Silica gel 60 with a particle size of 40-63 μm was purchased from Merck Millipore. Reversed phase column chromatography was performed on POLYGOPREP® 60-50 C$_{18}$ (Macherey Nagel GmbH & Co. KG, Germany). Deactivated silica gel 60 was purchased from MP Biomedical. Routine separation was performed with an automated Isolera™ One system (Biotage AG, Sweden) with commercially available cartridges.
Absorption Spectroscopy Absorption spectra were recorded with a Varian Cary 4000 UV-Vis double-beam spectrophotometer (Agilent Technologies, USA). For the determination of the absorption spectra, quartz cells with a 1 cm path length were used. Emission spectra and fluorescence quantum yield were obtained on a Quantaurus-QY Absolute PL quantum yield spectrometer C11347 (Hamamatsu Photonics, Japan) or on a Varian Cary Eclipse fluorescence spectrometer (Agilent Technologies, USA).

Nuclear Magnetic Resonance (NMR)

NMR Spectra were recorded on an Agilent 400MR DD2 spectrometer. All spectra are referenced to tetramethylsilane as an internal standard (δ=0.00 ppm) using the signals of the residual protons of CHCl$_3$ (7.26 ppm) in CDCl$_3$, CHD$_2$OD (3.31 ppm) in CD$_3$OD, CHD$_2$COCD$_3$ (2.05 ppm) in (CD$_3$)$_2$CO or DMSO-d$_5$ in DMSO-d$_6$. Multiplicities of the signals are described as follows: s=singlet, br. s=broad singlet, d=doublet, t=triplet, q=quartet, m=multiplet. Coupling constants $^nJ_{x,y}$ are given in Hz, where n is the number of bonds between the coupled nuclei x and y. For $^{13}$C-signals, which were revealed by indirect detection by HSQC, only resonances of the carbon atoms linked to H-atoms were recorded.
Mass-Spectrometry (MS)

Low resolution mass spectra (50-3500 m/z) with electrospray ionization (ESI) were obtained on a Varian 500-MS spectrometer (Agilent Technologies, USA). High resolution mass spectra (ESI-HRMS) were obtained on a Bruker micro TOF (ESI-TOF-MS) spectrometer (Bruker Corporation, USA).
High-Performance Liquid Chromatography (HPLC)

HPLC system (Knauer, Germany): Smartline pump 1000 (2×) with 10 mL pump-head, UV detector 2500, column thermostat 4000, mixing chamber, injection valve with a 20 or 50 μL loop for the analytical and 500 μL loop for preparative columns; 6-port-3-channel switching valve; analytical column: Eurospher-100 C18 5 μm (unless stated otherwise), or Kinetex C18 100, 5 μm, 250×4 mm, 1.2 mL/min; preparative column: Kinetex C18 100, 5 μm, 250×20 mm, 10 mL min/mL, solvent A: water+0.1% v/v trifluoroacetic acid (TFA); solvent B: MeCN+0.1% v/v TFA (unless stated otherwise). For isolation and purification of the acid sensitive dyes or their derivatives, acetonitrile aqueous systems containing 0.05-0.1 M of Et$_3$N*H$_2$CO$_3$ buffer (pH=8; Sigma, or self-prepared from 1 M aq. Et$_3$N and CO$_2$ gas obtained by evaporation of solid CO$_2$).
STED (Stimulated Emission Depletion) Microscopy STED and confocal counterpart images were acquired using the commercially available two-color STED 775 quad scanning microscope from Abberior Instruments (Gottingen, Germany) equipped with an Olympus IX83 microscope stand and an Olympus UplanSApo 100×/1.4 OIL objective. Dyes were excited respective their excitation; the STED laser was pulsed at 775 nm. Imaging and image processing was done with ImSpector software, and the images are displayed as raw data.

TABLE 2

Properties of exemplary novel compounds of the invention

| No. | Compound | Absorption max., nm (ε, M$^{-1}$cm$^{-1}$) | Emission max., nm (QY) | Stokes shift, nm | Stability; fluorescence lifetime, ns |
|---|---|---|---|---|---|
| 1 |  | 439 (24000)$^a$ | 651 (0.20)$^a$ | 212$^a$ | 2.55$^a$ |

TABLE 2-continued

Properties of exemplary novel compounds of the invention

| No. | Compound | Absorption max., nm (ε, M$^{-1}$cm$^{-1}$) | Emission max., nm (QY) | Stokes shift, nm | Stability; fluorescence lifetime, ns |
|---|---|---|---|---|---|
| 2 | [HO-azetidine-coumarin-benzothiazole with P(=O)(OMe)₂] | 424 (19000)$^a$ | 651 (0.16)$^a$ | 227$^a$ | 1.99$^a$ |
| 3 | [Et₂N-coumarin-benzothiazole with P(=O)(Ot-Bu)₂] | 434 (39000)$^a$ | 658 (0.29)$^a$ | 224$^a$ | 2.49$^a$ |
| 4 | [Et₂N-coumarin-benzothiazole with P(=O)(OH)₂] | 419 (22000)$^b$ | 613 (0.04)$^b$ | 194$^b$ | 2.91$^a$; 1.85$^c$ (0.93)$^d$, 0.93$^e$ (0.07)$^d$; 1.20$^b$ (0.28)$^d$, 0.30$^b$ (0.72)$^d$ |
| 5 | [Me₂N-xanthene-NMe₂ with P(=O)(OMe)₂] | 597 (21400)$^b$ | 667 (0.16)$^b$ | 70$^b$ | moderate |
| 6 | [Me₂N-xanthene-NMe₂ with P(=O)(OiPr)₂] | 617 (57600)$^a$ 629 (52300)$^b$ | 649 (0.38)$^a$ 668 (0.12)$^b$ | 32$^a$ 39$^b$ | moderate |
| 7 | [Me₂N-xanthene-NMe₂ with P(=O)(OMe)(NiPr₂)] | 616 (52500)$^a$ 628 (46100)$^b$ | 649 (0.39)$^a$ 664 (0.11)$^b$ | 33$^a$ 36$^b$ | moderate |

TABLE 2-continued

Properties of exemplary novel compounds of the invention

| No. | Compound | Absorption max., nm (ε, $M^{-1}cm^{-1}$) | Emission max., nm (QY) | Stokes shift, nm | Stability; fluorescence lifetime, ns |
|---|---|---|---|---|---|
| 8 | Me₂N-xanthene-NMe₂⁺ with O=P(Ph)(Ph) | 574[a] 601[b] | 600 (0.35)[a] 639 (0.26)[b] | 26[a] 38[b] | moderate |
| 9 | Me₂N-xanthene-NMe₂⁺ with Me₂N-P(=O)-O-C₆H₄-CO₂⁻ | 603 (69000)[b] 589 (49000)[e] | 638 (0.09)[b] 622 (0.36)[e] | 35[b] 33[e] | moderate 1.88[b] |
| 10 | Me₂N-xanthene-NMe₂⁺ with O=P(OEt)-N(Me)-CH₂CH₂-C(O)OH | 615[a] 625[b] | 652 (0.46)[a] 670 (0.15)[b] | 37[a] 45[b] | moderate |
| 11 | Me₂N-xanthene-NMe₂⁺ with O=P(O⁻)(OEt) | 565 (63500)[a] 597 (66600)[b] | 595 (0.44)[a] 633 (0.22)[b] | 30[a] 36[b] | moderate |
| 12 | Me₂N-xanthene-NMe₂⁺ with O=P(OMe)-O-(CH₂)₃-C(O)O-allyl | 621 (42700)[a] 632[b] | 653 (0.32)[a] 669 (0.17)[b] | 32[a] 37[b] | moderate |
| 13 | Me₂N-xanthene-NMe₂⁺ with O=P(H)(O⁻) | 590 (59400)[b] | 627 (0.33)[b] | 37[b] | good |

TABLE 2-continued

Properties of exemplary novel compounds of the invention

| No. | Compound | Absorption max., nm (ε, $M^{-1}cm^{-1}$) | Emission max., nm (QY) | Stokes shift, nm | Stability; fluorescence lifetime, ns |
|---|---|---|---|---|---|
| 14 | Me₂N-xanthene-NMe₂ with P(=O)(OEt)CH₂COO⁻ | 625[a] 631[b] | 656 (0.32)[a] 667 (0.22)[b] | 31[a] 36[b] | moderate |
| 15 | Me₂N-xanthene-NMe₂ with P(=O)(O⁻)CH₂CH₂COOH | 598 (52100)[b] | 636 (0.29)[b] | 38[b] | good |
| 16 | Me₂N-xanthene-NMe₂ with P(=O)(O⁻)CH₂CH₂C(=O)N(Me)(CH₂)₄COO⁻ | 603[b] | 636 (0.30)[b] | 33[b] | good[f] |
| 17 | julolidine-xanthene with P(=O)(OMe)(NiPr₂) | 649 (53000)[a] 661 (47000)[b] | 679 (0.25)[a] 696 (0.11)[b] | 30[a] 35[b] | moderate |
| 18 | julolidine-xanthene with P(=O)(OMe)(O⁻) | 596 (49600)[a] 630 (52300)[b] | 623 (0.85)[a] 666 (0.17)[b] | 27[a] 36[b] | moderate |

TABLE 2-continued

Properties of exemplary novel compounds of the invention

| No. | Compound | Absorption max., nm ($\varepsilon$, $M^{-1}cm^{-1}$) | Emission max., nm (QY) | Stokes shift, nm | Stability; fluorescence lifetime, ns |
|---|---|---|---|---|---|
| 19 | [structure] | 648$^a$ 659$^b$ | 682 (0.19)$^a$ 705 (0.11)$^b$ | 34$^a$ 46$^b$ | moderate |
| 20 | [structure] | 681 (40000)$^a$ 693 (29000)$^b$ | 737 (0.17)$^a$ 754 (0.02)$^b$ | 56$^a$ 61$^b$ | good 1.50$^a$ |
| 21 | [structure] | 654 (64000)$^a$ | 728 (0.10)$^a$ | 74$^a$ | moderate 0.77$^a$ |
| 22 | [structure] | 560 (43000)$^e$ | 620 (0.95)$^e$ | 60$^e$ | poor |
| 23 | [structure] | 535 (38000)$^b$ 527 (67000)$^e$ | 595 (0.10)$^b$ 579 (0.75)$^e$ | 60$^b$ 52$^e$ | good$^f$ 1.36$^b$ |

TABLE 2-continued

Properties of exemplary novel compounds of the invention

| No. | Compound | Absorption max., nm (ε, M$^{-1}$cm$^{-1}$) | Emission max., nm (QY) | Stokes shift, nm | Stability; fluorescence lifetime, ns |
|---|---|---|---|---|---|
| 24 | [structure] | 694 (37900)$^a$ | 779 (0.03)$^a$ | 85$^a$ | moderate |
| 25 | [structure] | 698 (40800)$^a$ 710 (16700)$^b$ | 775 (0.26)$^a$ 783 (0.19)$^b$ | 77$^a$ 73$^b$ | poor |
| 26 | [structure] | 724 (46700)$^a$ 734 (34700)$^b$ | 812 (0.08)$^a$ 860 (0.05)$^b$ | 88$^a$ 126$^b$ | poor |
| 27 | [structure] | 743 (42700)$^a$ 752$^b$ | 809 (0.06)$^a$ 819 (0.03)$^b$ | 66$^a$ 67$^b$ | poor |
| 28 | [structure] | 644 (7600)$^b$ | 782 (0.04)$^b$ | 138$^b$ | poor |

TABLE 2-continued

Properties of exemplary novel compounds of the invention

| No. | Compound | Absorption max., nm (ε, $M^{-1}cm^{-1}$) | Emission max., nm (QY) | Stokes shift, nm | Stability; fluorescence lifetime, ns |
|---|---|---|---|---|---|
| 29 | [structure: BODIPY with O=P(OiPr)(OiPr)] | 574 (33000)[a] | 647 (<0.002)[a] | 73[a] | no emission (quencher) |

[a] in acetonitrile;
[b] in aq. PBS, pH 7.4;
[c] in methanol + 1% v/v trifluoroacetic acid;
[d] biexponential;
[e] in methanol;
[f] verified as a label in super-resolution microscopy based on stimulated emission depletion (STED with 775 nm STED laser).

EXAMPLE 10

STED Optical Microscopy of Cells using Exemplary Novel Dyes of the Invention

For these experiments, STED optical microscopy was performed as indicated above.

FIG. 1 shows confocal and STED images (raw data) of tubulin filaments in a methanol-fixed Vero cell. Tubulin was marked using a mouse monoclonal primary antibody against alpha-tubulin together with secondary antibody detection (sheep-anti-mouse conjugated with the dye 23-NHS). 23 was excited using a pulsed 485 nm laser. Fluorescence was detected in both available detection channels (605-625 nm, 655-715nm) and summed up for the final images. Scale bar: 4 μm; pixel dwell time: 10 μs; pixel size: 25 nm for both the STED and the confocal image. Each line in the STED channel was scanned twice, and the counts were accumulated.

Figure 2:
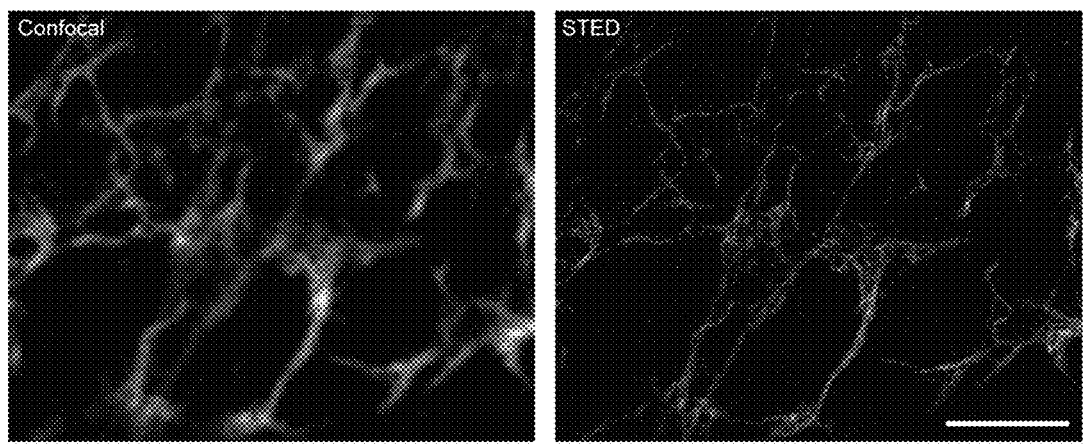
FIG. 2 shows confocal and STED images of vimentin filaments in a living HeLa cell that expresses a vimentin-HaloTag fusion protein labelled with 16-Halo.
Figure 3A:
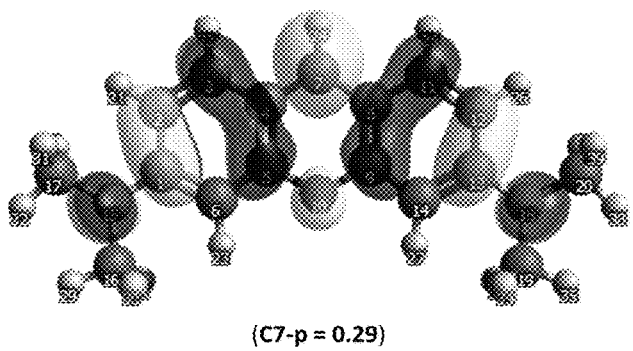
FIGS. 3A, 3B, 3C, 3D, 3E, 3F, 3G, 3H, and 3I show molecular orbital renderings of the dyes of Table 1.
Figure 3B:
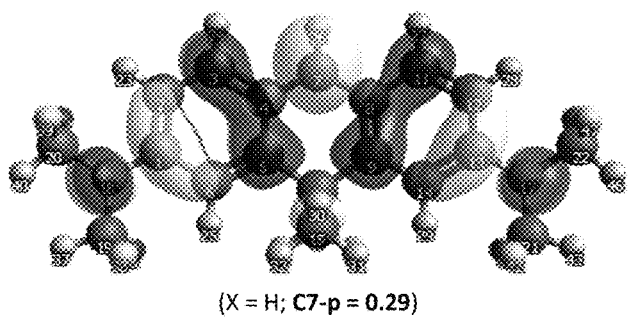
Figure 3C:
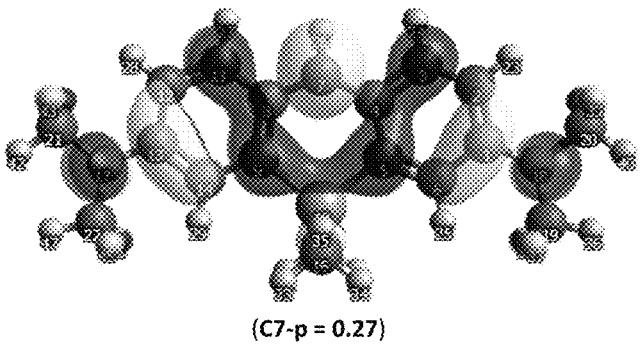
Figure 3D:
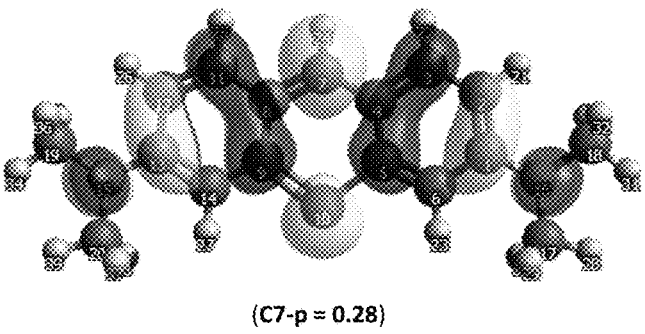
Figure 3E:
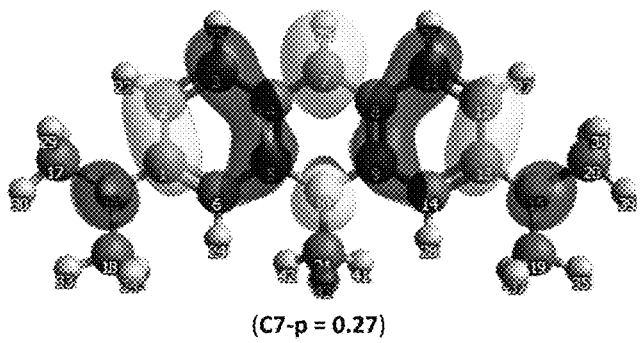
Figure 3F:
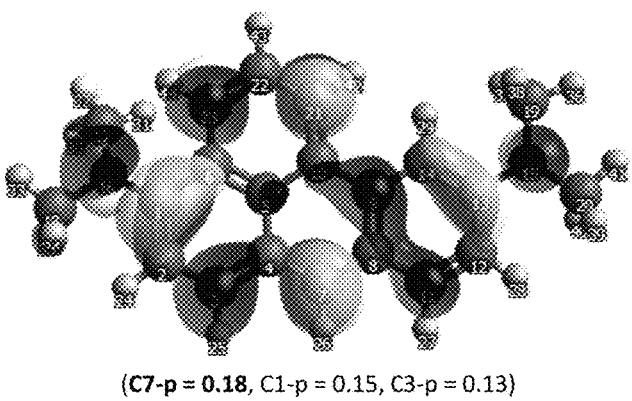
Figure 3G:
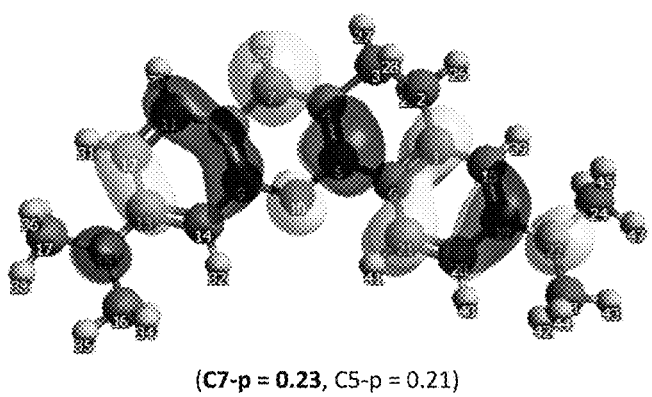
Figure 3H:
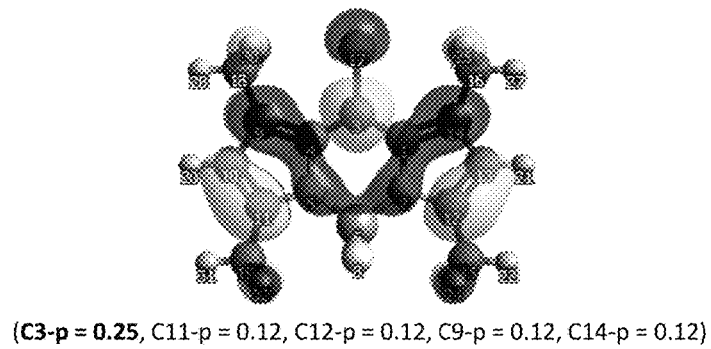
Figure 3I:
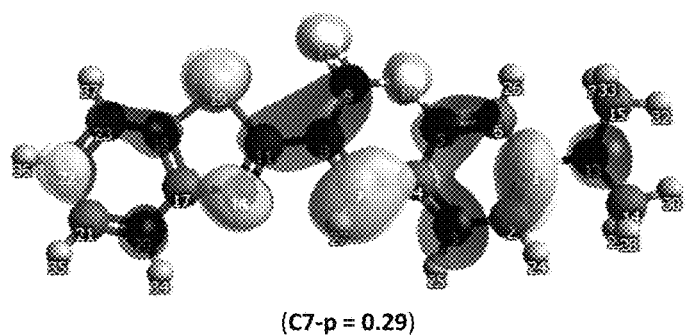

FIG. 2 shows confocal and STED images (raw data) of vimentin filaments in a living HeLa cell that expresses a vimentin-HaloTag fusion protein. The vimentin-HaloTag was labeled with 16-Halo (1 μM for 20 min at growth conditions, 10 min wash) and excited using a pulsed 594 nm laser. Fluorescence was detected in both available detection channels (605-625 nm, 655-715nm) and summed up for the final images. Scale bar: 4 μm; pixel dwell time: 10 μs; pixel size: 20 nm for both the STED and the confocal image. Each line was scanned four times, and the counts were accumulated.

The invention claimed is:

1. A compound which is a fluorescent dye and has the structural formula:

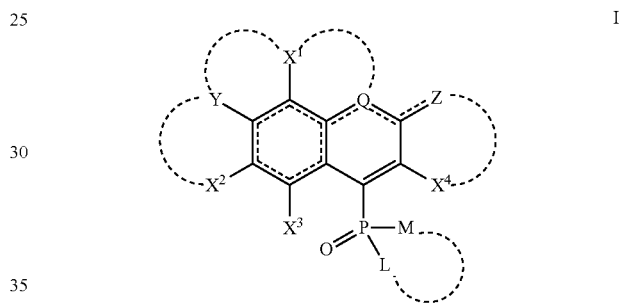

wherein:
each of $X^1$, $X^2$, $X^3$ and $X^4$ is a member independently selected from the group consisting of H, F, Cl, Br, I, CN, $NO_2$, $OR^1$, $SR^1$, $NR^1R^2$, $COR^1$, $COOR^1$, $CONR^1R^2$, $PO_3R^1R^2$, $SO_2R^1$, $SO_3R^1$ and $R^3$, where:
  $R^1$ and $R^2$ are independently selected from H, alkyl, aryl or heteroaryl, and $R^1$ and $R^2$ can optionally form together a substituted or unsubstituted 4-7 membered ring;
  $R^3$ is alkyl, alkenyl, alkynyl, aryl or cycloalkyl, optionally substituted with one or more heteroatoms independently selected from N, O, S, F, Cl, Br, I, $N_3$, amine, OH, $OR^1$, $OCOR^1$, aryl, $COOR^1$, $CONR^1R^2$, $PO_3H_2$ and $SO_3H$, where $R^1$ and $R^2$ are defined as above;
Y is selected from $OR^1$, $NR^1R^2$, or $NR^1R^3$, where $R^1$, $R^2$ and $R^3$ are defined as above;
Q is selected from O, S, $SO_2$, $NR^3$, $C(R^3)_2$, $Si(R^3)_2$, $Ge(R^3)_2$, $P(=O)R^3$, or $P(=O)OR^3$, where $R^3$ is defined as above, and wherein Q and $X^1$, taken together with the atoms to which they are bonded, can optionally form a substituted or unsubstituted 5-7 membered ring;
L and M are independently selected from $OR^1$, $SR^1$, $NR^1R^2$ or $R^3$, where $R^1$, $R^2$ and $R^3$ are defined as above, and wherein L and M, taken together with the atoms to which they are bonded, can optionally form a substituted or unsubstituted 5-7 membered ring; and
Z is selected from O, S, $NR^1$, $CR^1R^3$ or aryl, where $R^1$ and $R^3$ are defined as above, and wherein Z and $X^4$, taken with the atoms to which they are bonded, can optionally form a substituted or unsubstituted 5-7 membered ring.

2. The compound according to claim 1, wherein the amine is a member selected from the group consisting of $NH_2$, NH(alkyl), NH(aryl), N(alkyl)(aryl) and $N(alkyl)_2$.

3. The compound according to claim 1, where Z and $X^4$, taken with the atoms to which they are bonded, form a substituted or unsubstituted 5-7 membered ring, substituted with at least one additional heteroatom selected from the group consisting of N, O and S and/or at least one substituent selected from the group consisting of F, Cl, Br, I, CN, $N_3$, $B(OR^1)(OR^2)$, $OR^1$, $SR^1$, $NR^1R^2$, $COR^1$, $COOR^1$, $CONR^1R^2$, $PO_3R^1R^2$, $SO_2R^1$, $SO_3R^1$ and $R^3$, where $R^1$, $R^2$, $R^3$ are defined as in claim 1.

4. The compound according to claim 1, having one of the following formulae Ia-Is:

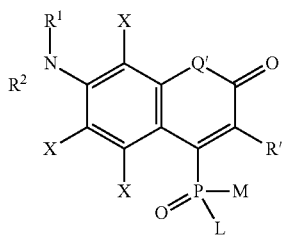

Ia wherein:

each substituent X is a member independently selected from the group consisting of: H, F, Cl, Br, I, CN, $NO_2$, $OR^1$, $SR^1$, $NR^1R^2$, $COR^1$, $COOR^1$, $CONR^1R^2$, $PO_3R^1R^2$, $SO_2R^1$, $SO_3R^1$ and $R^3$, where $R^1$, $R^2$, $R^3$ are defined as in claim 1;

the substituent R' is selected from H and $R^3$, where $R^3$ is defined as in claim 1;

Q' is selected from O, S, $SO_2$, $NR^3$, $C(R^3)_2$, $Si(R^3)_2$, $Ge(R^3)_2$, $P(=O)R^3$, and $P(=O)OR^3$, where $R^3$ is defined as in claim 1, L, M, $R^1$, $R^2$ are defined as in claim 1;

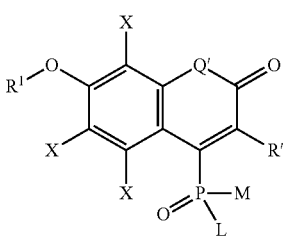

Ib wherein the substituents L, M, and $R^1$ are defined as in claim 1, the substituents Q', R' and X are defined as above;

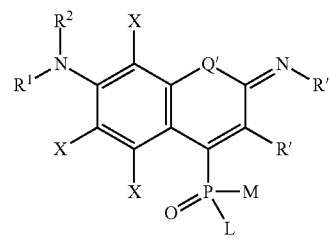

Ic wherein the substituents L, M, $R^1$ and $R^2$ are defined as in claim 1, the substituents Q', R' and X are defined as above;

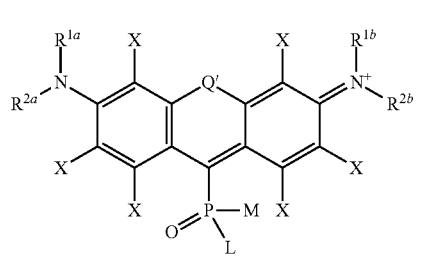

Id wherein:

$R^{1a}$ and $R^{2a}$ are independently selected from H, alkyl, aryl or heteroaryl, and wherein $R^{1a}$ and $R^{2a}$ can optionally form together a substituted or unsubstituted 4-7 membered ring;

$R^{1b}$ and $R^{2b}$ are independently selected from H, alkyl, aryl or heteroaryl, and wherein $R^{1b}$ and $R^{2b}$ can optionally form together a substituted or unsubstituted 4-7 membered ring;

L and M are defined as in claim 1,

Q' and X are defined as above, and a positive charge is delocalized among atoms of the conjugated system in alternating positions such that structure Id above represents only one possible mesomeric structure;

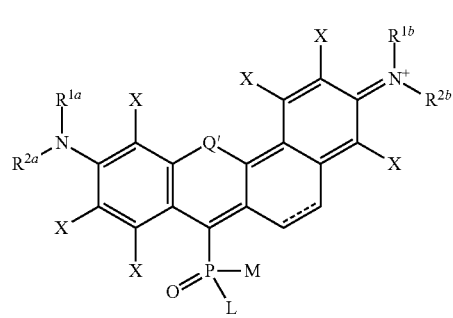

Ie wherein:

$R^{1a}$ and $R^{2a}$ are independently selected from H, alkyl, aryl or heteroaryl, and wherein $R^{1a}$ and $R^{2a}$ can optionally form together a substituted or unsubstituted 4-7 membered ring;

$R^{1b}$ and $R^{2b}$ are independently selected from H, alkyl, aryl or heteroaryl, and wherein $R^{1b}$ and $R^{2b}$ can optionally form together a substituted or unsubstituted 4-7 membered ring;

L and M are defined as in claim 1,

Q' and X are defined as above, and a positive charge is delocalized among atoms of the conjugated system in alternating positions such that structure Ie above represents only one possible mesomeric structure;

If

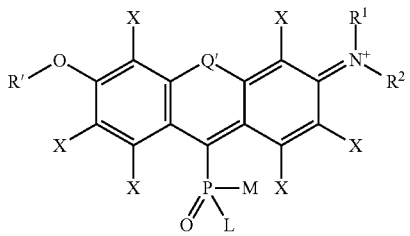

wherein the substituents L, M, $R^1$ and $R^2$ are defined as in claim 1,

Q', R' and X are defined as above, and a positive charge is delocalized among atoms of the conjugated system in alternating positions such that structure If above represents only one possible mesomeric structure;

Ig

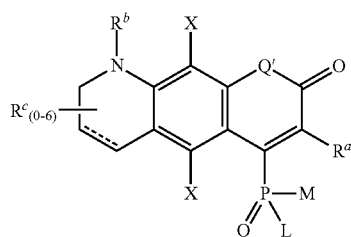

wherein the substituents L and M are defined as in claim 1,

Q' and X are defined as above, $R^a$, $R^b$ and $R^c$ are independently selected from H and $R^3$, where $R^3$ is defined as in claim 1;

Ih

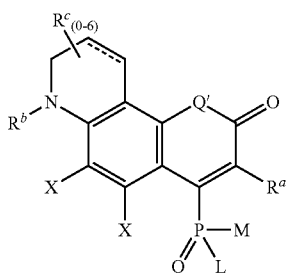

wherein the substituents L and M are defined as in claim 1,

Q' and X are defined as above, $R^a$, $R^b$ and $R^c$ are independently selected from H and $R^3$, where $R^3$ is defined as in claim 1;

Ii

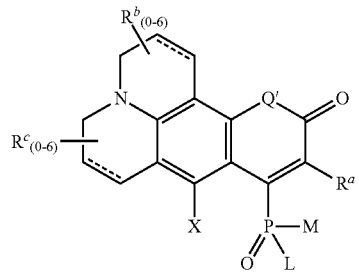

wherein the substituents L and M are defined as in claim 1,

Q' and X are defined as above, $R^a$, $R^b$ and $R^c$ are independently selected from H and $R^3$, where $R^3$ is defined as in claim 1;

Ij

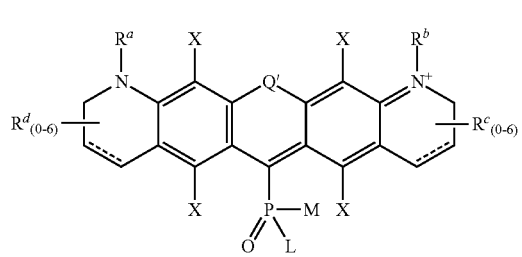

wherein the substituents L and M are defined as in claim 1,

Q' and X are defined as above, $R^a$, $R^b$, $R^c$ and $R^d$ are independently selected from H and $R^3$, where $R^3$ is defined as in claim 1, and a positive charge is delocalized among atoms of the conjugated system in alternating positions such that structure Ij above represents only one possible mesomeric structure;

Ik

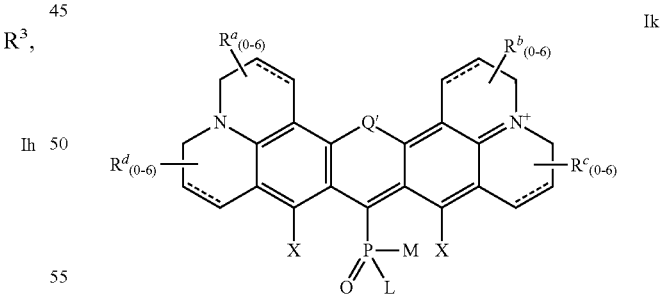

wherein the substituents L and M are defined as in claim 1,

Q' and X are defined as above, $R^a$, $R^b$, $R^c$ and $R^d$ are independently selected from H and $R^3$, where $R^3$ is defined as in claim 1, and a positive charge is delocalized among atoms of the conjugated system in alternating positions such that structure Ik above represents only one possible mesomeric structure;

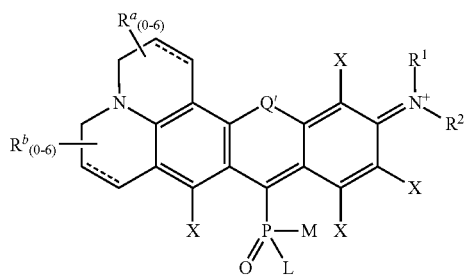

wherein the substituents L, M, $R^1$ and $R^2$ are defined as in claim 1,
Q' and X are defined as above,
$R^a$ and $R^b$ are independently selected from H and $R^3$, where $R^3$ is defined as in claim 1,
and a positive charge is delocalized among atoms of the conjugated system in alternating positions such that structure Il above represents only one possible mesomeric structure;

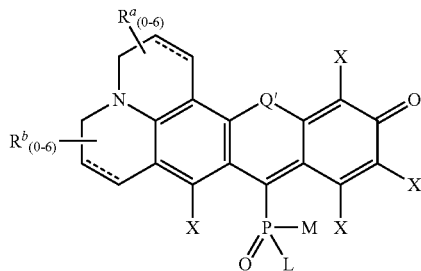

and a positive charge is delocalized among atoms of the conjugated system in alternating positions such that structure In above represents only one possible mesomeric structure;

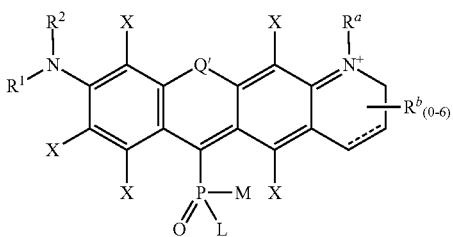

wherein the substituents L and M are defined as in claim 1,
Q' and X are defined as above,
$R^a$ and $R^b$ are independently selected from H and $R^3$, where $R^3$ is defined as in claim 1;

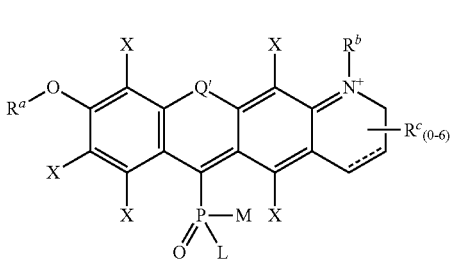

wherein the substituents L, M, $R^1$ and $R^2$ are defined as in claim 1,
Q' and X are defined as above,
$R^a$ and $R^b$ are independently selected from H and $R^3$, where $R^3$ is defined as in claim 1,
and a positive charge is delocalized among atoms of the conjugated system in alternating positions such that structure Im above represents only one possible mesomeric structure;

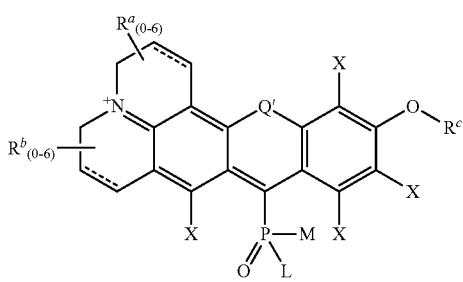

wherein the substituents L and M are defined as in claim 1,
Q' and X are defined as above,
$R^a$ and $R^b$ are independently selected from H and $R^3$, where $R^3$ is defined as in claim 1,
and a positive charge is delocalized among atoms of the conjugated system in alternating positions such that structure Ip above represents only one possible mesomeric structure;

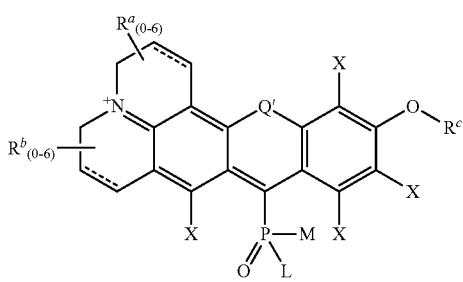

wherein the substituents L and M are defined as in claim 1,
Q' and X are defined as above,
$R^a$, $R^b$ and $R^c$ are independently selected from H and $R^3$, where $R^3$ is defined as in claim 1,
and a positive charge is delocalized among atoms of the conjugated system in alternating positions such that structure Iq above represents only one possible mesomeric structure;

wherein the substituents L and M are defined as in claim 1,
Q' and X are defined as above,
$R^a$, $R^b$ and $R^c$ are independently selected from H and $R^3$, where $R^3$ is defined as in claim 1, wherein the substituents L and M are defined as in claim 1, X is defined as above, R$^{1a}$ and R$^{2a}$ are independently selected from H, alkyl, aryl or heteroaryl, and wherein R$^{1a}$ and R$^{2a}$ can optionally form together a substituted or unsubstituted 4-7 membered ring, R$^{1b}$ and R$^{2b}$ are independently selected from H, alkyl, aryl or heteroaryl, and wherein R$^{1b}$ and R$^{2b}$ can optionally form together a substituted or unsubstituted 4-7 membered ring, and the positive charge is delocalized among the atoms of the conjugated system in alternating positions (only one mesomeric structure Ir is shown); and wherein the substituents L and M are defined as in claim 1, X is defined as above, R$^a$ and R$^b$ are independently selected from H and R$^3$, where R$^3$ is defined as in claim 1, R$^1$ and R$^2$ are independently selected from H, alkyl, aryl or heteroaryl, and wherein R$^1$ and R$^2$ can optionally form together a substituted or unsubstituted 4-7 membered ring, and the positive charge is delocalized among the atoms of the conjugated system in alternating positions (only one mesomeric structure Is is shown).

5. The compound according to claim 1, wherein R$^1$ of COOR$^1$ is N-succinimidyl, N-phthalimidyl, N-tetrachlorphthalimidyl, pentachlorophenyl, pentafluorophenyl, 2,3,5,6-tetrafluorophenyl, 4-(hydroxysulfonyl)-2,3,5,6-tetrafluorophenyl [p-(HOSO$_2$)C$_6$F$_4$], 1-benzotriazolyl or cyanomethyl.

6. The compound according to claim 1, wherein R$^1$ of OR$^1$ is N-succinimidyl, N-phthalimidyl, N-tetrachlorphthalimidyl, pentachlorophenyl, pentafluorophenyl, 2,3,5,6-tetrafluorophenyl, 4-(hydroxysulfonyl)-2,3,5,6-tetrafluorophenyl [p-(HOSO$_2$)C$_6$F$_4$], 1-benzotriazolyl or cyanomethyl.

7. The compound according to claim 4 having a structural formula selected from:

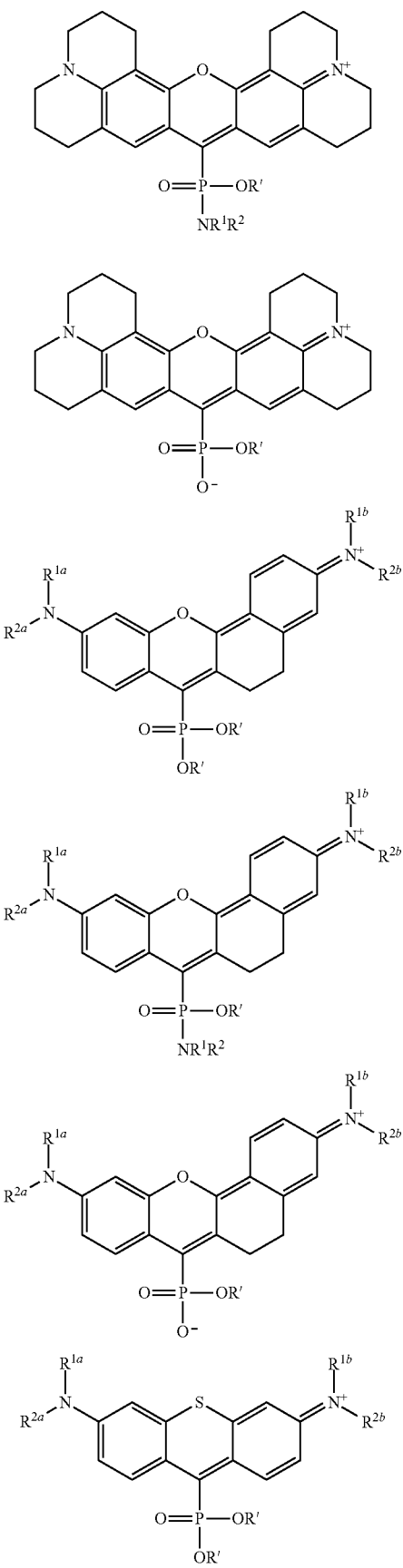
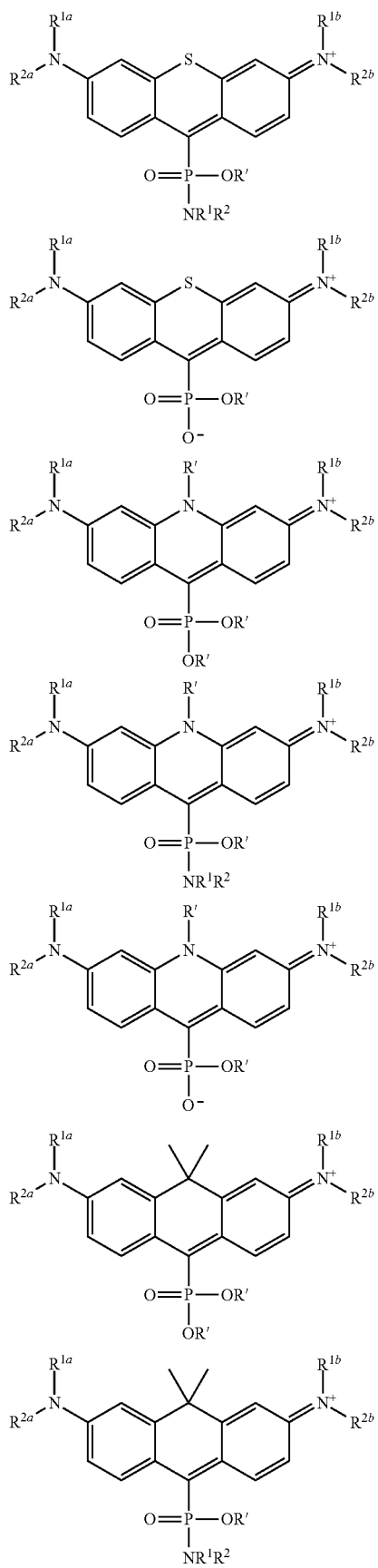

-continued
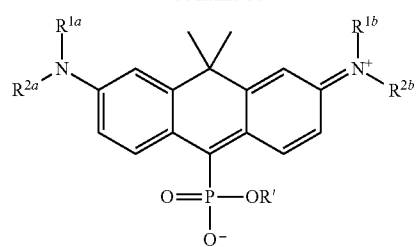
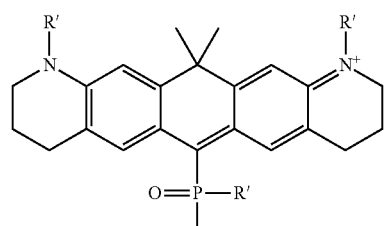
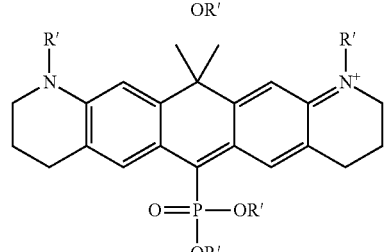
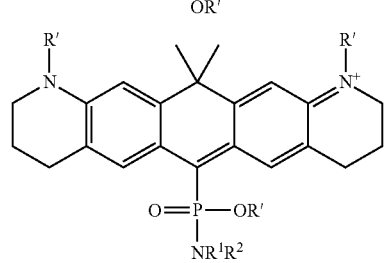
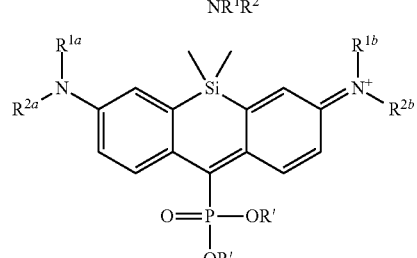
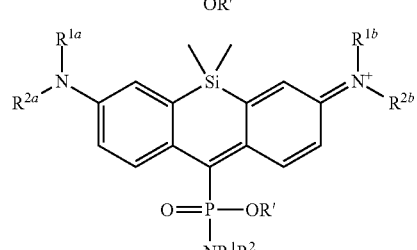
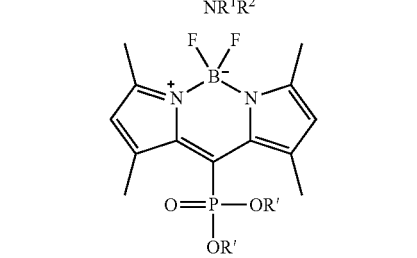
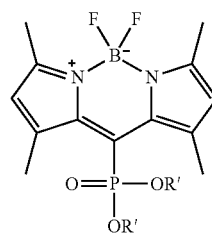
-continued
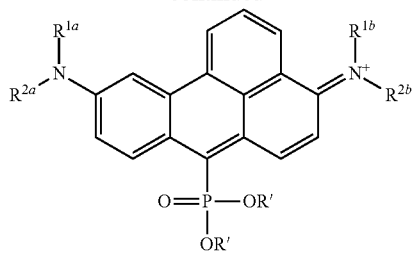
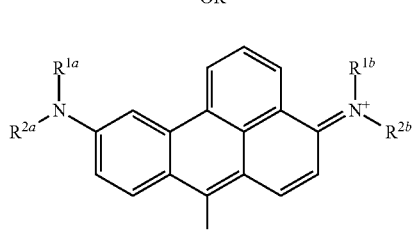
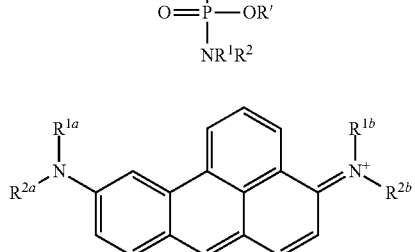
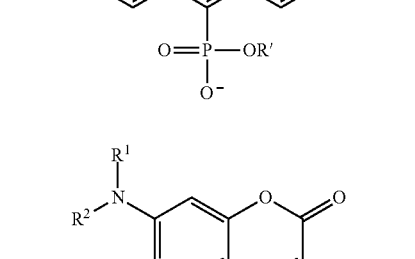
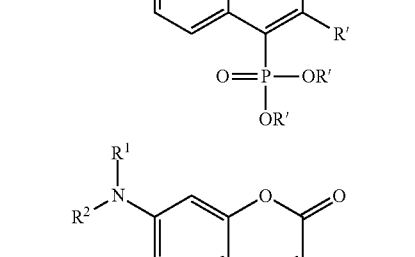
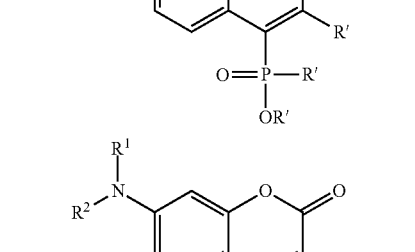
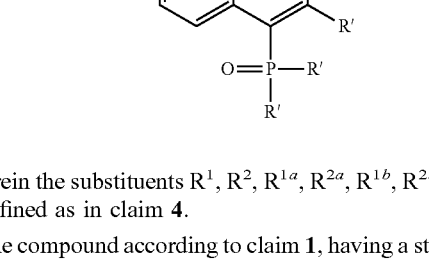
wherein the substituents $R^1$, $R^2$, $R^{1a}$, $R^{2a}$, $R^{1b}$, $R^{2b}$, R' are defined as in claim 4.
8. The compound according to claim 1, having a structural formula selected from:

115
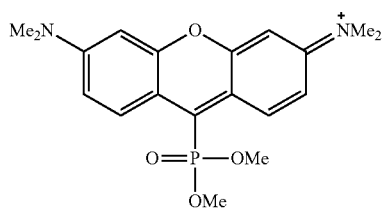
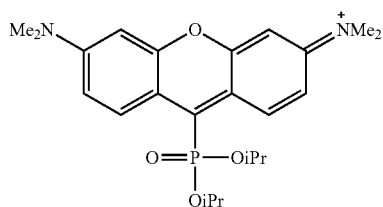
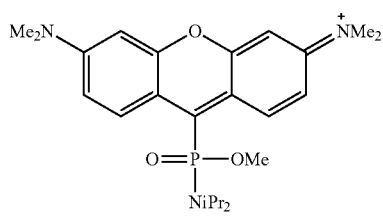
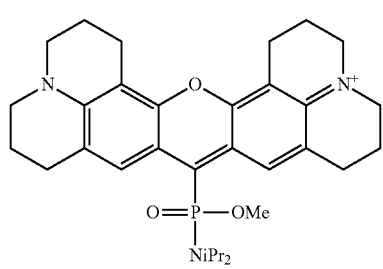
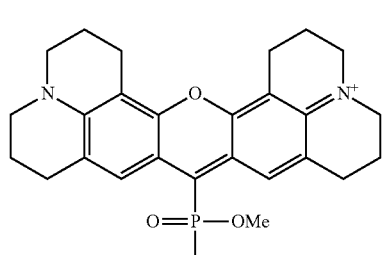
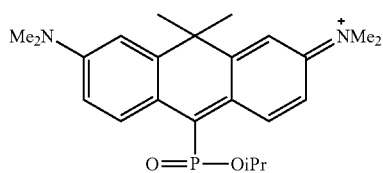
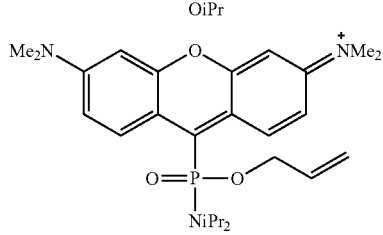
116
-continued
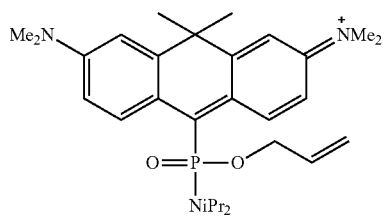
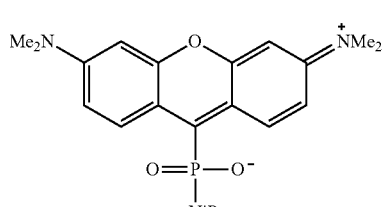
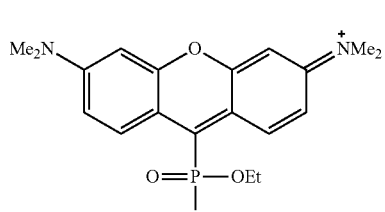
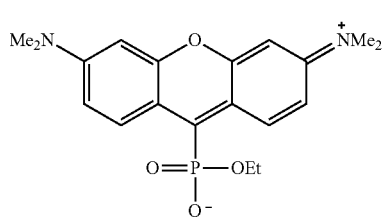
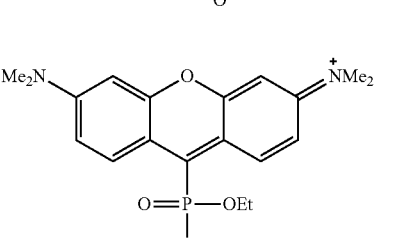
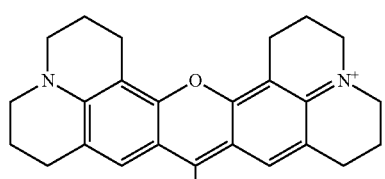
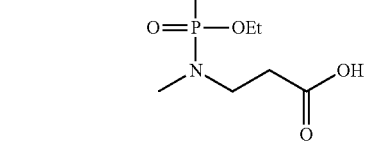

117
-continued
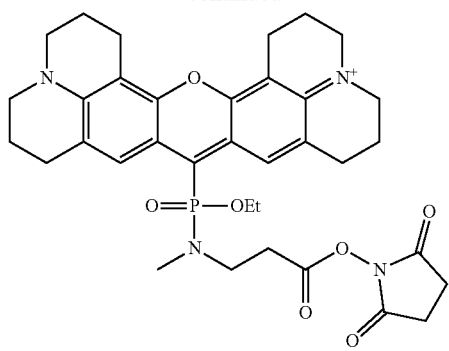
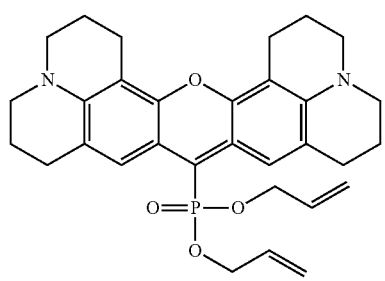
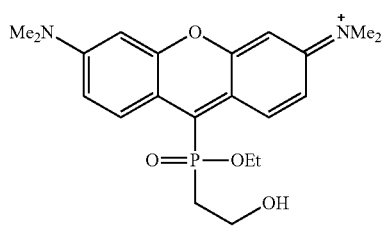
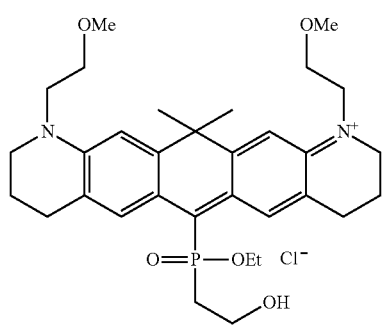
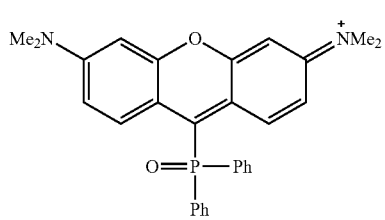
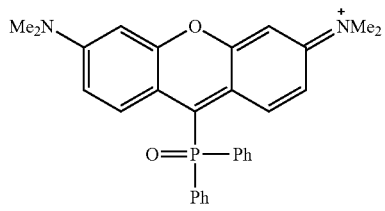
118
-continued
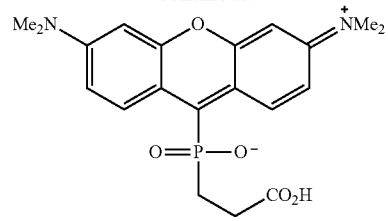
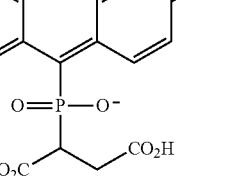
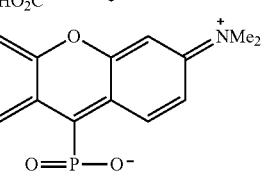
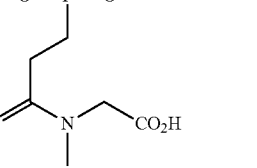
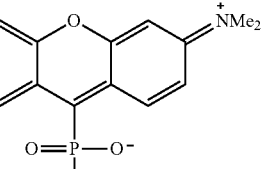
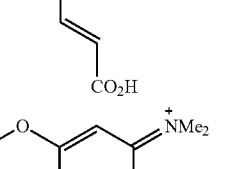
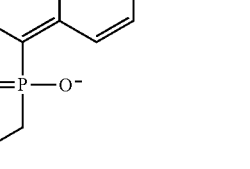
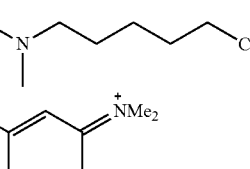
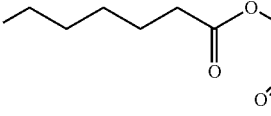

-continued

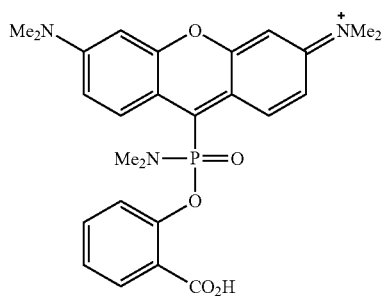
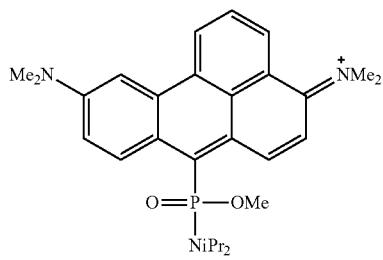
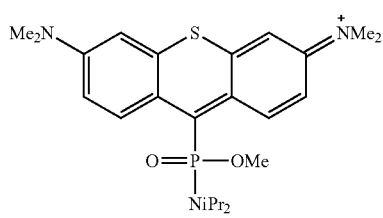
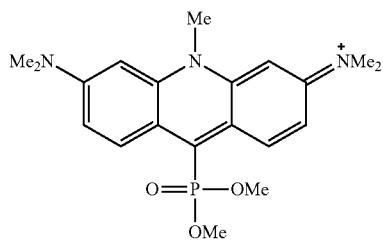
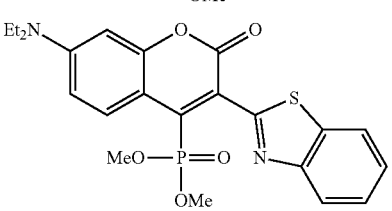
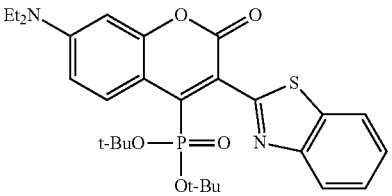
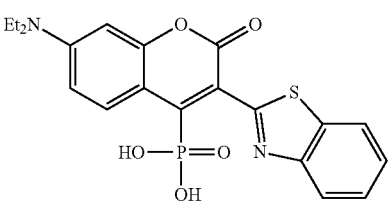

-continued

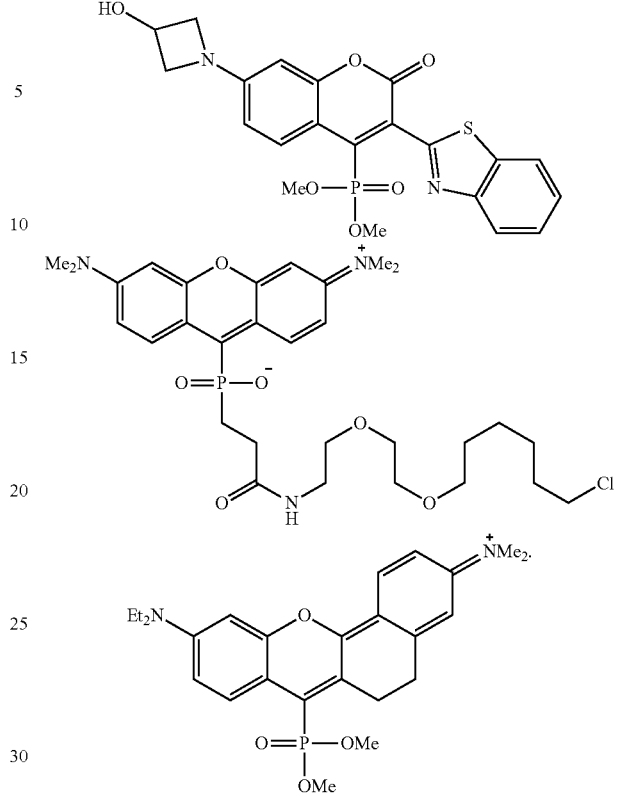

9. The compound according to claim 1 in a form of a salt with organic or inorganic counterion(s), its cocrystal with another organic or inorganic compound(s), or a composition containing any of the dyes of claim 1.

10. A conjugate or bioconjugate comprising a compound according to claim 1 coupled via at least one covalent chemical bond or at least one molecular complex to a chemical entity or substance.

11. A method for preparing the compound according to claim 1, comprising the following steps:
   a) Reacting of a precursor compound having the following structure III:

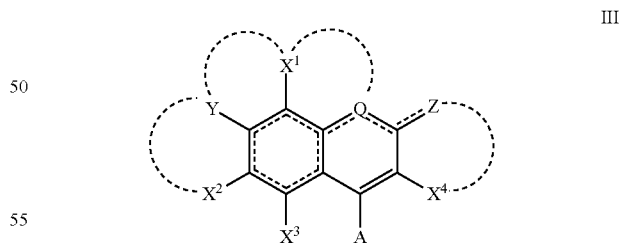

wherein Q, $X^1$, $X^2$, $X^3$, $X^4$, Y and Z are defined as in claim 1, and A is either a hydrogen atom or a reacting group selected from the group consisting of CN, Cl, Br, I, triflate (OTf), and nonaflate (ONf), with phosphinic (hypophosphorous) acid $H_3PO_2$, phosphinites [$R^aO$-$PR^bR^c$], phosphonites [$(R^aO)(R^bO)PR^c$], phosphites $R^cOP(OR^a)(OR^b)$, phosphoramidites $R^cR^dNP(OR^a)$ $(OR^b)$, where $R^{a-d}$ are H, alkyl or aryl, or salts of the corresponding esters, where at least one of $R^{a-d}$ is a metal; the reacting providing either directly a compound of claim 1, or an intermediate compound, which can be isolated or used as crude material for the following step;
b) Optional alkylation of an intermediate phosphinic ester leuco derivative with an alkyl halide, alkyl sulfonate or a Michael acceptor, if step a) was performed with phosphinic (hypophosphorous) acid or its esters;
c) Oxidizing of the leuco intermediate into a dye of the formula of claim 1 by oxidation with an organic or inorganic oxidant, or with an inorganic oxidant in the presence of catalytic amounts of an organic oxidant(s), or electrochemically, with or without subsequent acidic or basic hydrolysis; and
d) Optionally performing post-synthetic modifications.

12. The method of claim 11, wherein step a) is catalyzed by a nucleophilic catalyst.

13. The method according to claim 11, wherein the organic oxidant is selected from 2,3-dichloro-5,6-dicyano-1,4-benzoquinone (DDQ), 2,3,5,6-tetrachloro-1,4-benzoquinone (p-chloranil), 3,4,5,6-tetrachloro-1,2-benzoquinone (o-chloranil), or other quinones, and/or the inorganic oxidant is selected from oxygen, hydrogen peroxide, iodine, periodate salts, $Mn(OAc)_3$, $Pb(OAc)_4$, $PbO_2$, or $K_3[Fe(CN)_6]$.

14. The method according to claim 11, wherein step c) is performed in vitro or in vivo resulting in a detectable response.

15. The compound according to claim 1, which is a fluorescent label, probe, tracer or marker, as well as quencher in fluorescence energy transfer (FRET) experiments, imaging and optical microscopy.

16. The compound according to claim 15, which is effective for tracking and monitoring dynamic processes in a sample or in an object.

17. The compound according to claim 1, which is a fluorescent tag, analytical reagent or label suitable for use in optical microscopy, imaging techniques, protein tracking, nucleic acid labeling and flow cytometry.

18. The compound according to claim 17, wherein the optical microscopy and imaging methods comprise stimulated emission depiction microscopy, minimal photon fluxes techniques, single molecule switching techniques, single molecule localization microscopy, photoactivation localization microscopy, stochastic optical reconstruction microscopy, direct STORM; fluorescence correlation spectroscopy, fluorescence recovery after photobleaching, fluorescence lifetime imaging, ground state depletion with individual molecular return and fluorescence resonant energy transfer.

19. The compound according to claim 4, having formula Ifa and/or Ifb:

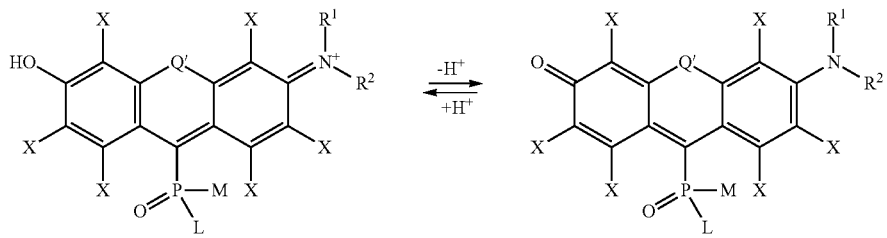

wherein a positive charge is delocalized among atoms of the conjugated system in alternating positions such that structure Ifa above represents only one possible mesomeric structure.

20. The compound according to claim 4, having the following formula

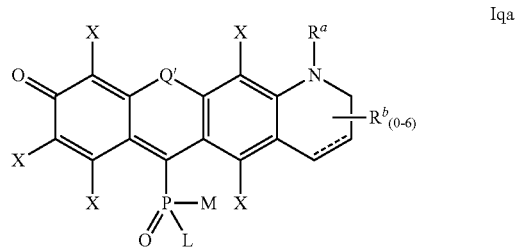

wherein $R^a$ and $R^b$ are independently selected from H and $R^3$.

21. A compound which is a fluorescent dye and has a structural formula selected from the group consisting of:

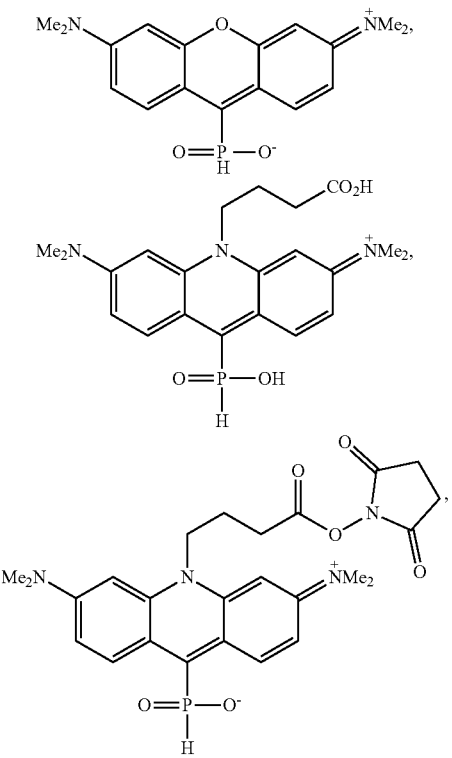

-continued
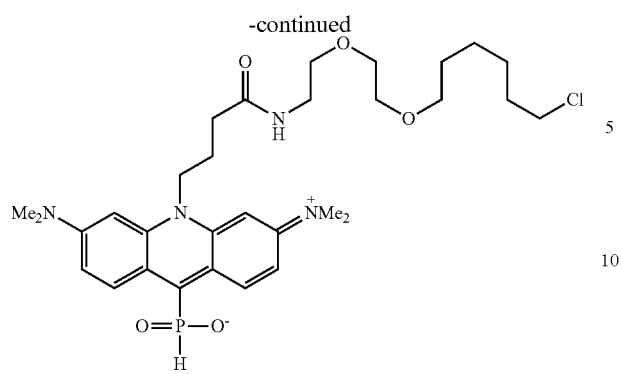
and
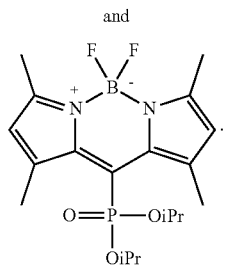
* * * * *